United States Patent
Crunick et al.

(10) Patent No.: US 9,782,324 B2
(45) Date of Patent: Oct. 10, 2017

(54) SYSTEM AND METHOD FOR TREATING SKIN AND UNDERLYING TISSUES FOR IMPROVED HEALTH, FUNCTION AND/OR APPEARANCE

(71) Applicant: Sigma Instruments Holdings, LLC, Cranberry Township, PA (US)

(72) Inventors: John Crunick, Cranberry Township, PA (US); Tamas Becse, Wexford, PA (US); Louis L. Laskey, Jr., Prospect, PA (US)

(73) Assignee: Sigma Instruments Holdings, LLC, Cranberry Twp., PA (US)

( * ) Notice: Subject to any disclaimer, the term of this patent is extended or adjusted under 35 U.S.C. 154(b) by 773 days.

(21) Appl. No.: 14/205,105

(22) Filed: Mar. 11, 2014

(65) Prior Publication Data

US 2014/0194790 A1 Jul. 10, 2014

Related U.S. Application Data

(63) Continuation-in-part of application No. PCT/US2012/055551, filed on Sep. 14, 2012.
(Continued)

(51) Int. Cl.
*A61H 23/02* (2006.01)
*A61N 1/32* (2006.01)
(Continued)

(52) U.S. Cl.
CPC .............. *A61H 23/02* (2013.01); *A61B 5/05* (2013.01); *A61B 5/053* (2013.01); *A61B 5/0531* (2013.01);
(Continued)

(58) Field of Classification Search
CPC .... A61H 23/00; A61H 23/006; A61H 23/008; A61H 23/02; A61H 23/0218;
(Continued)

(56) References Cited

U.S. PATENT DOCUMENTS

| | | |
|---|---|---|
| 3,499,437 A | 3/1970 | Balamuth |
| 4,530,360 A | 7/1985 | Durate |

(Continued)

FOREIGN PATENT DOCUMENTS

| | | |
|---|---|---|
| DE | 10306795 A1 | 9/2004 |
| KR | 10-0400870 B | 10/2003 |

(Continued)

OTHER PUBLICATIONS

U.S. Appl. No. 14/344,313, filed Mar. 11, 2014, Crunick et al.
(Continued)

*Primary Examiner* — Justine Yu
*Assistant Examiner* — Colin W Stuart
(74) *Attorney, Agent, or Firm* — Polsinelli PC

(57) ABSTRACT

Systems and methods for treating facial soft tissues of a patient in a healthcare or cosmetic treatment environment such as, for example, a spa, clinic, or a medical practitioner's office are presented herein. The facial treatment system includes a facial stimulator instrument and/or an acoustic oscillator to deliver therapeutic stimulation to the facial tissues of a patient including percussive massage, electrical stimulation, and acoustic stimulation. A facial treatment application executing on a processor of a computing device identifies a treatment protocol and operates the facial stimulator instrument and/or acoustic oscillator to implement the facial tissue treatment.

17 Claims, 41 Drawing Sheets

Related U.S. Application Data

(60) Provisional application No. 61/616,967, filed on Mar. 28, 2012, provisional application No. 61/535,225, filed on Sep. 15, 2011, provisional application No. 61/791,203, filed on Mar. 15, 2013.

(51) Int. Cl.
   *A61B 5/053* (2006.01)
   *A61B 5/05* (2006.01)
   *A61H 23/00* (2006.01)
   *A61B 5/0488* (2006.01)

(52) U.S. Cl.
   CPC ....... *A61H 23/006* (2013.01); *A61H 23/0218* (2013.01); *A61H 23/0236* (2013.01); *A61H 23/0245* (2013.01); *A61N 1/328* (2013.01); *A61B 5/0488* (2013.01); *A61H 2201/10* (2013.01); *A61H 2201/165* (2013.01); *A61H 2201/5015* (2013.01); *A61H 2201/5035* (2013.01); *A61H 2201/5038* (2013.01); *A61H 2201/5043* (2013.01); *A61H 2201/5046* (2013.01); *A61H 2201/5061* (2013.01); *A61H 2201/5071* (2013.01); *A61H 2201/5084* (2013.01); *A61H 2205/022* (2013.01); *A61H 2230/605* (2013.01)

(58) Field of Classification Search
   CPC ............ A61H 23/0236; A61H 23/0245; A61H 2023/0227; A61H 1/008; A61N 1/328; A61N 1/18; A61B 5/05; A61B 5/053; A61B 5/0531
   USPC ............ 601/18, 15, 21, 46, 47, 48; 600/306, 600/372, 546, 547, 548, 587, 10, 11
   See application file for complete search history.

(56) References Cited

U.S. PATENT DOCUMENTS

| | | | |
|---|---|---|---|
| 4,946,692 | A | 8/1990 | Bernhardt et al. |
| 4,984,127 | A | 1/1991 | Evans |
| 5,209,221 | A | 5/1993 | Riedlinger |
| 5,300,095 | A | 4/1994 | Salazar |
| 5,413,550 | A | 5/1995 | Castel |
| 5,586,067 | A | 12/1996 | Gross |
| 5,601,526 | A | 2/1997 | Chapelon et al. |
| 6,321,119 | B1 | 11/2001 | Kronberg |
| 6,413,230 | B1 | 7/2002 | Haupt et al. |
| 6,419,648 | B1 | 7/2002 | Vitek et al. |
| 6,514,220 | B2 | 2/2003 | Melton, Sr. et al. |
| 6,539,328 | B1 | 3/2003 | Cremonese et al. |
| 6,540,700 | B1 | 4/2003 | Fujimoto et al. |
| 6,565,520 | B1 | 5/2003 | Young |
| 6,645,162 | B2 | 11/2003 | Friedman et al. |
| 7,123,967 | B2 | 10/2006 | Weinberg |
| 7,144,417 | B2 | 12/2006 | Colloca et al. |
| 7,435,232 | B2 | 10/2008 | Liebschner |
| 7,519,427 | B2 | 4/2009 | Sakagami et al. |
| 7,894,907 | B2 | 2/2011 | Cowan et al. |
| 7,899,542 | B2 | 3/2011 | Cowan et al. |
| 8,048,006 | B2 | 11/2011 | Harris |
| D711,900 | S | 8/2014 | Crunick et al. |
| 2003/0125649 | A1 | 7/2003 | McIntosh et al. |
| 2004/0015106 | A1* | 1/2004 | Coleman ............ A61H 23/0236 601/3 |
| 2004/0171970 | A1 | 9/2004 | Schleuniger et al. |
| 2005/0043659 | A1 | 2/2005 | Challis et al. |
| 2005/0222524 | A1 | 10/2005 | Fielding et al. |
| 2006/0009810 | A1 | 1/2006 | Mann et al. |
| 2006/0122579 | A1 | 6/2006 | Pisciottano |
| 2006/0160158 | A1 | 7/2006 | Ebright |
| 2006/0184075 | A1 | 8/2006 | Restle et al. |
| 2007/0073361 | A1 | 3/2007 | Goren et al. |
| 2007/0091091 | A1 | 4/2007 | Gardiner et al. |
| 2007/0173903 | A1 | 7/2007 | Goren et al. |
| 2007/0203533 | A1 | 8/2007 | Goren et al. |
| 2008/0021353 | A1 | 1/2008 | Menzi et al. |
| 2008/0077434 | A1 | 3/2008 | Man et al. |
| 2008/0183164 | A1 | 7/2008 | Elkins |
| 2009/0018404 | A1 | 1/2009 | Fendelander et al. |
| 2009/0043293 | A1 | 2/2009 | Pankratov |
| 2009/0149782 | A1 | 6/2009 | Cohen |
| 2009/0178626 | A1 | 7/2009 | Greeson |
| 2009/0326607 | A1 | 12/2009 | Castel et al. |
| 2010/0094187 | A1 | 4/2010 | Murinson |
| 2010/0105933 | A1 | 4/2010 | Chen et al. |
| 2010/0131025 | A1 | 5/2010 | Henry |
| 2011/0112405 | A1* | 5/2011 | Barthe ................. A45D 44/005 600/459 |
| 2011/0118810 | A1 | 5/2011 | Cowan et al. |
| 2011/0166621 | A1 | 7/2011 | Cowan et al. |
| 2011/0171325 | A1 | 7/2011 | Lozano |
| 2011/0196438 | A1* | 8/2011 | Mnozil .................. A61B 18/14 607/3 |
| 2011/0213253 | A1 | 9/2011 | Kruglick |
| 2012/0271206 | A1* | 10/2012 | Shalev ................. A61H 9/0057 601/15 |
| 2014/0031866 | A1 | 1/2014 | Fuhr |
| 2016/0113840 | A1 | 4/2016 | Crunick et al. |
| 2016/0151238 | A1 | 6/2016 | Crunick et al. |

FOREIGN PATENT DOCUMENTS

| | | |
|---|---|---|
| KR | 10-2010-0082140 A | 7/2010 |
| WO | WO 99-34724 A2 | 7/1999 |
| WO | WO 02-098318 A2 | 12/2002 |
| WO | WO 2010/009141 A1 | 1/2010 |
| WO | WO 2011-080191 A1 | 7/2011 |
| WO | WO 2013/040451 A2 | 3/2013 |

OTHER PUBLICATIONS

U.S. Appl. No. 14/344,311, filed Mar. 11, 2014, Crunick et al.
U.S. Appl. No. 14/372,989, filed Jul. 17, 2014, Becse et al.
European Search Report, EP12832599.0, dated Apr. 2, 2015.
International Search Report and Written Opinion, PCT/US2014/040953, dated Oct. 6, 2014.
Chinese Office Action (English), 201480039884.X, dated Aug. 10, 2016.
Extended European Search Report, EP14807934.6, dated Feb. 1, 2017.
Final Office Action, U.S. Appl. No. 14/372,989, dated May 2, 2016.
Final Office Action, U.S. Appl. No. 14/895,843, dated Oct. 17, 2016.
Non-Final Office Action, U.S. Appl. No. 14/895,843, dated Apr. 22, 2016.
Notice of Allowance, U.S. Appl. No. 14/372,989, dated Aug. 10, 2016.
Response to Final Office Action, U.S. Appl. No. 14/372,989, dated Jul. 29, 2016.
Response to Non-Final Office Action, U.S. Appl. No. 14/895,843, dated Sep. 22, 2016.
International Search Report and Written Opinion, PCT/US2012/055538, dated Jan. 30, 2013, 11 pages.
International Search Report and Written Opinion, PCT/US2012/055564, dated Feb. 28, 2013, 10 pages.
International Search Report and Written Opinion, PCT/US2013/021973, dated May 15, 2013, 15 pages.
International Search Report and Written Opinion, PCT/US2012/055551, dated Feb. 26, 2013, 12 pages.

* cited by examiner

SYSTEM AND METHOD FOR TREATING SKIN AND UNDERLYING TISSUES FOR IMPROVED HEALTH, FUNCTION AND/OR APPEARANCE

CROSS-REFERENCE TO RELATED CASES

The present application is a continuation-in-part of International Application No. PCT/US2012/055551, which is entitled Systems and Methods for Treating Skin and Underlying Tissues for Improved Health, Function and/or Appearance, with an international filing date of Sep. 14, 2012. The PCT application claims priority to U.S. Provisional Patent Application No. 61/616,967, filed Mar. 28, 2012, and entitled System and Method for Treating Skin and Underlying Tissues for Improved Health, Function and/or Appearance; and also claims priority to U.S. Provisional Patent Application No. 61/535,225, which is entitled Systems and Methods for Preventing and/or Treating Peripheral Neuropathy and Peripheral Vascular Disease, and was filed Sep. 15, 2011.

This application also claims priority to U.S. Provisional Patent Application No. 61/791,203, which is entitled System and Method for Treating Skin and Underlying Tissues for Improved Health, Function and/or Appearance, and was filed Mar. 15, 2013.

The contents of all of the above-mentioned patent applications are hereby incorporated by reference in their entireties.

FIELD OF THE INVENTION

Aspects of the present invention relate to systems and methods related to skin health and beauty. More specifically, the present invention relates to medical systems and methods for treating facial soft tissues of a patient in a healthcare or cosmetic treatment environment such as, for example, a spa, clinic, or a medical practitioner's office.

BACKGROUND OF THE INVENTION

The prevention or amelioration of the effects of aging on facial skin is a major focus of the health and beauty industry. In addition to the ubiquitous beauty creams and other topical skin treatment compounds, a number of other treatments attempt to address underlying causes of wrinkling and loss of skin tone such as abnormal facial muscle tone, facial nerve anomalies, and disrupted circulation in the facial circulatory vessels. Less invasive treatments to address these underlying causes include cosmetic acupuncture and facial toning treatments such as active exercising of the facial muscles or passive exercise of the facial muscles using electrostimulation of the facial muscles. However, due to the lack of standardization of the administration of these less invasive treatments, and the limited ability to assess the efficacy of these treatments, patients may opt for more invasive treatments that yield more dramatic and immediate results.

Invasive cosmetic procedures such as the injection of *botulinum* toxin (BOTOX®) into facial muscles as well as surgical procedures such as brow lifts, eyelid lifts, face lifts, and collagen injections, are accompanied by a significant risk inherent in any surgical procedure or injection of a foreign substance. In addition, the effects of these invasive cosmetic procedures, for better or worse, are typically not easily reversed, may be temporary, and may lead to long-term degradation of the facial tissues.

A need exists for a system and method of non-invasively treating facial tissues such as muscular, nervous, and circulatory tissues in a standardized manner using standardized diagnostic criteria. In addition, a need exists for a system and method of assessing the efficacy of a facial tissue treatment in a standardized and non-biased manner. Such a system and method would overcome many of the current limitations of non-invasive facial treatment methods such as facial toning, and make possible a safe and effective alternative to the invasive cosmetic surgery methods commonly used to ameliorate the effects of aging on the facial tissues.

BRIEF SUMMARY OF THE INVENTION

Disclosed herein is a system for treating a facial tissue of a patient. In one embodiment, the system includes a display and input device, at least one camera, and at least one instrument chosen from a facial stimulator instrument and an acoustic oscillator. The facial stimulator is configured to apply a percussive massage comprising one or more force impulses and/or an electrical stimulation comprising one or more electrical pulses to the facial tissue. The facial stimulator is further configured to measure a response of the facial tissue to one of the applied force impulses or to one of the applied electrical pulses to assess a condition of the facial tissue. The acoustic oscillator is configured to apply an acoustic stimulation comprising one or more acoustic pulses to the facial tissue of the patient.

In this embodiment, the system also includes at least one processor and a database. The database may include at least one stored treatment protocol, stored patient data, and at least one measurement-correlated instrument control setting. The stored patient data may include at least one stored facial image; and at least one patient-specific treatment protocol.

The system in this embodiment further includes a facial treatment application executed by the processor to obtain at least one facial image using the at least one camera, to assess the symmetry of one or more facial landmarks from the at least one facial image, and to select a treatment protocol. The treatment protocol may include one or more instrument control settings, and one or more facial landmarks to be treated.

The facial treatment application may further implement one or more treatments to the facial tissue according to one or more selected treatment protocols by operating one of the instruments using a graphical display to guide an operator of the system through the treatment of the one or more facial landmarks. The one or more treatments are chosen from a neural treatment, a muscular treatment, and a circulatory treatment. The neural treatment includes applying one or more percussive massages and/or one or more electrical stimulations to one or more facial landmarks associated with facial nerves. The muscular treatment includes applying one or more percussive massages and/or one or more electrical stimulations to one or more facial landmarks associated with facial muscles. The circulatory treatment includes applying one or more acoustic stimulations to one or more facial landmarks associated with facial circulatory vessels.

Also disclosed herein is a method of treating a facial tissue of a patient. In one embodiment, the method includes obtaining at least one facial image using at least one camera, assessing the symmetry of one or more facial landmarks from the at least one facial image, and selecting a treatment protocol that includes one or more instrument control settings as well as one or more facial landmarks to be treated.

The method in this embodiment further includes implementing one or more treatments to the facial tissue according to one or more selected treatment protocols by operating at least one instrument by using a graphical display to guide an operator through the treatment of the one or more facial landmarks. The at least one instrument may be chosen from a facial stimulator instrument and an acoustic oscillator.

The one or more treatments implemented by the method in this embodiment include a neural treatment, a muscular treatment, and a circulatory treatment. The neural treatment includes administering one or more percussive massages and/or one or more electrical stimulations to one or more facial landmarks associated with facial nerves. The muscular treatment includes administering one or more percussive massages and/or one or more electrical stimulations to one or more facial landmarks associated with facial muscles. The circulatory treatment includes administering one or more acoustic stimulations to one or more facial landmarks associated with facial circulatory vessels.

Further disclosed herein is a second embodiment of a system for treating a facial tissue of a patient, including memory, at least one camera, at least one instrument, and a plurality of modules executing on at least one processor. The memory includes at least one stored treatment protocol, stored patient data, and at least one measurement-correlated instrument control setting. The stored patient data includes at least one stored facial image and at least one patient-specific treatment protocol.

The at least one instrument may include a facial stimulator instrument to apply a percussive massage comprising one or more force impulses and/or an electrical stimulation comprising one or more electrical pulses to the facial tissue. The facial stimulator instrument also measures a response of the facial tissue to one of the applied force impulses or to one of the applied electrical pulses to assess a condition of the facial tissue. The at least one instrument may also include an acoustic oscillator to apply an acoustic stimulation comprising one or more acoustic pulses to the facial tissue.

The plurality of modules includes a treatment protocol selection module, a neural treatment module, a muscular treatment module, and a circulatory treatment module. The treatment protocol selection module selects one or more treatment protocols based on at least one of: the stored patient data, an analysis of the condition of the facial tissues, one or more of the stored treatment protocols, one or more of the stored patient-specific treatment protocols, and a treatment protocol specified by the operator. The neural treatment module implements a neural treatment comprising one or more percussive massages and/or one or more electrical stimulations to one or more facial landmarks associated with facial nerves. The muscular treatment module implements a muscular treatment comprising one or more percussive massages and/or one or more electrical stimulations to one or more facial landmarks associated with facial muscles. The circulatory treatment module implements a circulatory treatment comprising one or more acoustic stimulations to one or more facial landmarks associated with facial circulatory vessels.

Disclosed herein is a system for cosmetically treating tissue of a patient for at least one of improving skin appearance, reducing skin wrinkles, improving skin tone, or improving tissue function. In one embodiment the system includes a display, an input, a CPU, a memory, a first RF head, a RF receiver antenna, a plurality of second RF heads, and an EMG sensor. The display includes a LCD or other type of screen and is configured to display information associated with the treatment of the tissue. The input is in electrical communication with the display and includes a key board, touch screen, or other type of input mechanism. The input is configured to receive information associated with the treatment of the tissue. The CPU is in electrical communication with the input. The memory is in electrical communication with the CPU and includes treatment parameters associated with the treatment of the tissue. The first RF head is capable of being placed in electrical communication with the CPU and includes an array of piezoelectric transducers. The array is configured to generate RF over a range of frequencies not possible via a single piezoelectric transducer. The RF receiver antenna is capable of being placed in electrical communication with the CPU and is configured to detect RF energy transmitted through the tissue from the first RF head. For the plurality of second RF heads, each second RF head has a piezoelectric transducer tuned to a unique frequency and is capable of being placed in electrical communication with the CPU. The EMG sensor is capable of being placed in electrical communication with the CPU and is configured to detect electromyogram in the tissue. When the first RF head and RF receiver antenna are applied to the tissue, the system is configured to: a) cause the first RF head to administer RF energy to the tissue over a range of RF frequencies; b) cause the RF receiver antenna to sense the administered RF energy transmitted through the tissue; c) identify which RF frequency of the range of RF frequencies administered to the tissue has the most transmissibility through the tissue; and d) recommend a second RF head of the plurality of RF heads that is capable of providing the identified RF frequency. When the recommended second RF head and EMG sensor are applied to the tissue, the system is configured to: a) cause the recommended second RF head to administer RF energy at the identified RF frequency to the tissue over a range of pulse frequencies; b) cause the EMG sensor to detect electromyogram in the tissue arising due to the RF energy administered to the tissue over the range of pulse frequencies; c) identify which pulse frequency of the range of pulse frequencies administered to the tissue causes the highest electromyogram readings in the tissue; and d) treat the tissue with the recommended second RF head at the identified RF frequency at the identified pulse frequency.

Depending on the version of the embodiment of the system, the array is configured to generate RF over a range of between approximately 500 KHz and approximately 1.5 MHz at, for example, steps of between approximately 50 KHz and approximately 200 KHz.

In one version of the embodiment of the system, the piezoelectric transducers of the array include a first piezoelectric transducer, a second piezoelectric transducer, and a third piezoelectric transducer, wherein each of the first, second and third piezoelectric transducers generate RF at distinct frequencies from each other. In one version of the embodiment of the system, the plurality of second RF heads includes individual second RF heads each tuned to a unique frequency from each other and each unique frequency is between approximately 500 KHz and approximately 1.5 MHz.

In one version of the embodiment of the system, when the recommended second RF head is caused to administer RF energy at the identified RF frequency to the patient over a range of pulse frequencies, the range of pulse frequencies is between approximately 1 Hz and approximately 300 Hz. In one version of the embodiment of the system, the recommended second RF head is caused to administer RF energy at the identified RF frequency to the patient over the pulse frequency range of between approximately 500 KHz and approximately 1.5 MHz at steps programmatically controlled and optimized for tissue type via stored protocols.

In one version of the embodiment of the system, the system further includes an impulse head capable of being placed in electrical communication with the CPU and including a solenoid driven anvil configured to deliver mechanical impulse energy to the tissue. The impulse head further includes a transducer sensor for detecting a wave generated in the tissue via the administration of the mechanical impulse energy to the tissue.

In one version of the embodiment of the system, the system further includes an electrode capable of being placed in electrical communication with the CPU and configured to administer electrical stimulation to the tissue and read electrical characteristics of the tissue in response to the electrical stimulation. The electrode may be supported on the impulse head.

In one version of the embodiment of the system, the system further includes a camera capable of being placed in electrical communication with the CPU and configured to take images of the tissue. The system is configured to compare images of the tissue taken pre and post treatment via the system.

Also disclosed herein is a method for cosmetically treating tissue of a patient for at least one of improving skin appearance, reducing skin wrinkles, improving skin tone, or improving tissue function. In one embodiment, the method includes: administering RF energy to the tissue over a range of RF frequencies; detecting the administered RF energy; identifying which RF frequency of the range of RF frequencies has the greatest transmissibility through the tissue; recommending the identified RF frequency for use in further RF energy treatment to the tissue; administering the RF energy at the identified RF frequency to the tissue over a range of pulse frequencies; identifying which pulse frequency of the range of pulse frequencies results in the highest electromyogram readings in the tissue; recommending the identified pulse frequency for use in further RF energy treatment to the tissue; and administering the RF energy at the identified RF frequency and identified pulse frequency to the tissue.

In one version of the embodiment of the method, the administration of the RF energy to the tissue over the range of frequencies is accomplished via a RF head having an array of piezoelectric transducers each tuned to an individual unique frequency, the array being configured to generate RF over a range of between approximately 500 KHz and approximately 1.5 MHz.

In one version of the embodiment of the method, the administration of the RF energy to the tissue over the range of frequencies is over a range of between approximately 500 KHz and approximately 1.5 MHz at steps of between approximately 50 KHz and approximately 200 KHz.

In one version of the embodiment of the method, the recommending the identified RF frequency for use in further RF energy treatment to the tissue includes identifying a specific RF head from a plurality of RF heads that is configured to provide the recommended RF frequency.

In one version of the embodiment of the method, the administering the RF energy at the identified RF frequency to the tissue over a range of pulse frequencies occurs over a pulse frequencies ranging between approximately 1 Hz and approximately 300 Hz programmatically controlled and optimized for tissue type via stored protocols.

In one version of the embodiment of the method, the administering the RF energy at the identified RF frequency to the patient over a range of pulse frequencies occurs over a pulse frequencies ranging between approximately 1 Hz and approximately 30 Hz.

While multiple embodiments are disclosed, still other embodiments of the present disclosure will become apparent to those skilled in the art from the following detailed description, which shows and describes illustrative embodiments of the disclosure. As will be realized, the invention is capable of modifications in various aspects, all without departing from the spirit and scope of the present disclosure. Accordingly, the drawings and detailed description are to be regarded as illustrative in nature and not restrictive.

BRIEF DESCRIPTION OF THE DRAWINGS

Corresponding reference characters and labels indicate corresponding elements among the views of the drawings. The headings used in the figures should not be interpreted to limit the scope of the claims.

DETAILED DESCRIPTION

Figure 1:
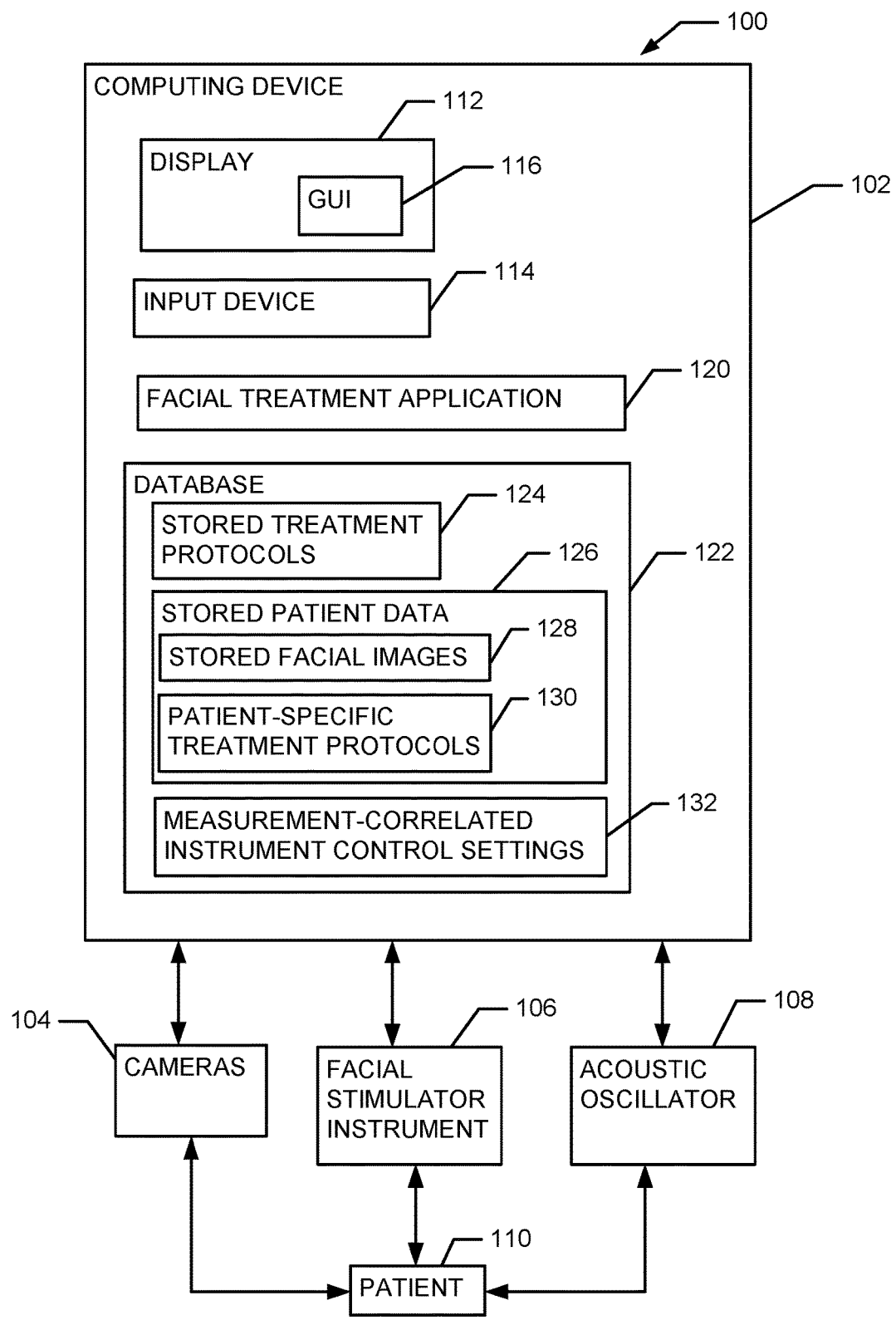
FIG. 1 is a block diagram of a facial treatment system.

Disclosed herein is a system and method for assessing and treating the facial tissues of a patient including, but not limited to: facial nerves, muscles, connective tissues, and circulatory vessels. In an aspect, the system is configured to provide one or more treatments to the facial tissues of the patient in the form of: percussive massage, electrical stimulation, acoustic stimulation, and any combination thereof. In other aspects, the system may be further configured to obtain one or more assessments of the condition of the facial tissues before and/or after one or more treatments, and to store these assessments in a database. These stored assessments may be used in an aspect to assess the efficacy of one or more treatments, to monitor changes in the facial tissues over time, and to inform the selection of subsequent treatments. In various embodiments of the system, a treatment may be selected using one or more methods including, but not limited to: selecting a treatment from a predefined menu of treatment protocols, determining a treatment based on an analysis of the condition of the facial tissues of the patient, selecting a treatment from a predefined menu of patient-specific treatment protocols, or specifying a user-defined protocol for a treatment.

In one aspect, the facial treatment system may be used to maintain and/or enhance the health and appearance of facial tissues. Non-limiting examples of aspects of the health and appearance of facial tissues that may be treated using the facial treatment system include: changes in appearance related to aging and erosion of subdermal fat including thinning of the skin, loss of elasticity and tone of skin, drooping of mouth corners, and formation of jowls; wrinkles including horizontal forehead lines, glabellar frown lines, crow's feet, perioral lines, marionette folds, and platysma bands; and changes or irregularities in skin coloration due to cutaneous conditions such as rosacea or dermatitis. In other aspects, the facial treatment system may be used to treat a variety of disorders afflicting one or more of the facial tissues. Non-limiting examples of disorders that may be treated using the facial treatment system include: strabismus, blepharospasm, hemifacial spasm and other facial muscle spasms, facial muscle weakness, loss of reciprocal inhibition of facial muscles, decreased movement control, facial muscle hypertonicity, hyperhidrosis, chronic migraines, TMJ pain disorders, trigeminal neuralgia, postherpetic neuralgia, facial nerve injuries including neuropraxia, neurotmesis, and axonotmesis; Bell's palsy, facial nerve paralysis; facial tissue abnormalities associated with systemic disorders such as muscular dystrophy, cerebral palsy, and Ramsay Hunt syndrome (RHS) type 2, sensory anomalies associated with facial nerve dysfunction such as tinnitus or taste disorders; central facial palsy, dysarthria, facial synkinesis, hyperlacrimation, orofacial myological disorders such as tongue thrust, oropharyngeal dysphagia, speech disorders associated with abnormal facial muscle tone, atypical facial pain (AFP), facial tics, and herpes zoster oticus.

Aspects of the facial treatment system described herein provide standardized and repeatable treatment protocols for the facial tissues of a patient, and further provide the ability to obtain and store information related to the condition of the facial tissues before, during, and after a treatment. This information allows the operator to monitor the efficacy of the treatment both immediately after the treatment, as well as after the passage of time between treatments; this information may further inform the selection of a treatment protocol and/or dynamically adjust the protocol during the administration of a treatment.

Detailed descriptions of embodiments of the facial treatment system, devices included in the facial treatment system, and methods of using the facial treatment system are provided herein below.

I. Facial Treatment System

The elements of a facial treatment system 100 are depicted in FIG. 1. The system 100 includes a computing device 102, one or more cameras 104, a facial stimulator instrument 106, and an acoustic (RF) oscillator 108. Non-limiting examples of a suitable computing device include a laptop computer, a personal digital assistant, a tablet computer, a standard personal computer, or any other known processing device. The computing device 102 includes one or more processors and memory configured to send, receive, and process data and/or communications from an operator of the system 100, the one or more cameras 104, the facial stimulator instrument 106, and the acoustic oscillator 108 in order to assess the condition of the facial tissues of a patient 110, select a treatment protocol, and implement a treatment of the facial tissues of the patient 110.

The one or more cameras 104 are configured to obtain facial images of the patient 110 that may be used to assess the condition of the facial tissues before, during, and/or after a treatment. The facial stimulator instrument 106 is configured to deliver a plurality of percussive shock waves and/or a plurality of electrical pulses to the facial tissues of the patient 110 during the course of a treatment. The facial stimulator instrument 106 is further configured to measure characteristics of the facial tissue of the patient 110, such as tissue reactive force during the application of a percussive shock wave, or tissue galvanic response during the application of an electrical pulse. The acoustic oscillator 108 is configured to deliver acoustic pulses to the facial tissues of a patient during the course of a treatment. The one or more cameras 104, the facial stimulator instrument 106, and the acoustic oscillator 108 are further configured to receive data and/or communications from the computing device 102 in order to operate the devices in a coordinated manner during the implementation of a treatment by the system 100.

The computing device 102 includes a display 112 configured to display data and/or graphical user interfaces (GUIs) 116 to the operator. Non-limiting examples of devices suitable for use as a display 112 include a computer monitor and a touch screen. The computing device 102 may further include an input device 114 including, but not limited to, a keyboard and/or a pointing device such as a mouse, a trackball, a pen, or a touch screen. The input device 114 is configured to enter data into or interact with the GUIs 116 used to implement the operation of the system 100. In an embodiment, the display 112 and input device 114 may be a single integrated device, such as a touch screen. The GUI 116 enables the operator of the system 100 to interact with menus and other data entry forms used to control the operation of the system 100.

The computing device 102 further includes a facial treatment application 120 configured to receive and process data and/or communications, as well as produce and send data and/or communications used to perform the functions of the system 100 described herein above, and in detail herein below. The data and/or communications produced by the facial treatment application 120 may be sent to the display 112 in order to guide the operator of the system 100 through the functions of the system 100. In addition, the data and/or communications may be sent to the one or more cameras 104, the facial stimulator instrument 106, and/or acoustic oscillator 108 in order to operate these devices in a coordinated manner during the operation of the system 100.

The computing device 102 further includes a database 122 configured to store a plurality of stored treatment protocols 124, stored patient data 126, and measurement-correlated instrument control settings 132. The stored treatment protocols 124 may include data utilized during the implementation of one or more treatments to the patient 110 using the system 100. For example, one of the stored treatment protocols 124 may include parameters used for the implementation of a treatment such as the location of the treatment on the facial tissues of the patient 110 and instrument operating parameters such as a power setting or a duration of instrument operation. The stored patient data 126 may include patient-specific information used to monitor the condition of the facial tissue of the patient 110 over time, to maintain a record of previous treatments performed by the system 100, to provide a schedule of future treatments, and to perform a customized treatment on a particular patient 110 using the system 100. The stored patient data 126 may include stored facial images 128 obtained by the system 100 using the one or more cameras 104. The stored patient data 126 may further include patient-specific treatment protocols 130 that may include parameters used for the implementation of a treatment that are customized for the treatment of a particular patient 110 based on a previous assessment of the condition of the facial tissues of the patient 110 and/or previous treatments performed on a particular patient 110 using the system 100.

II. Facial Treatment Application

Figure 2:
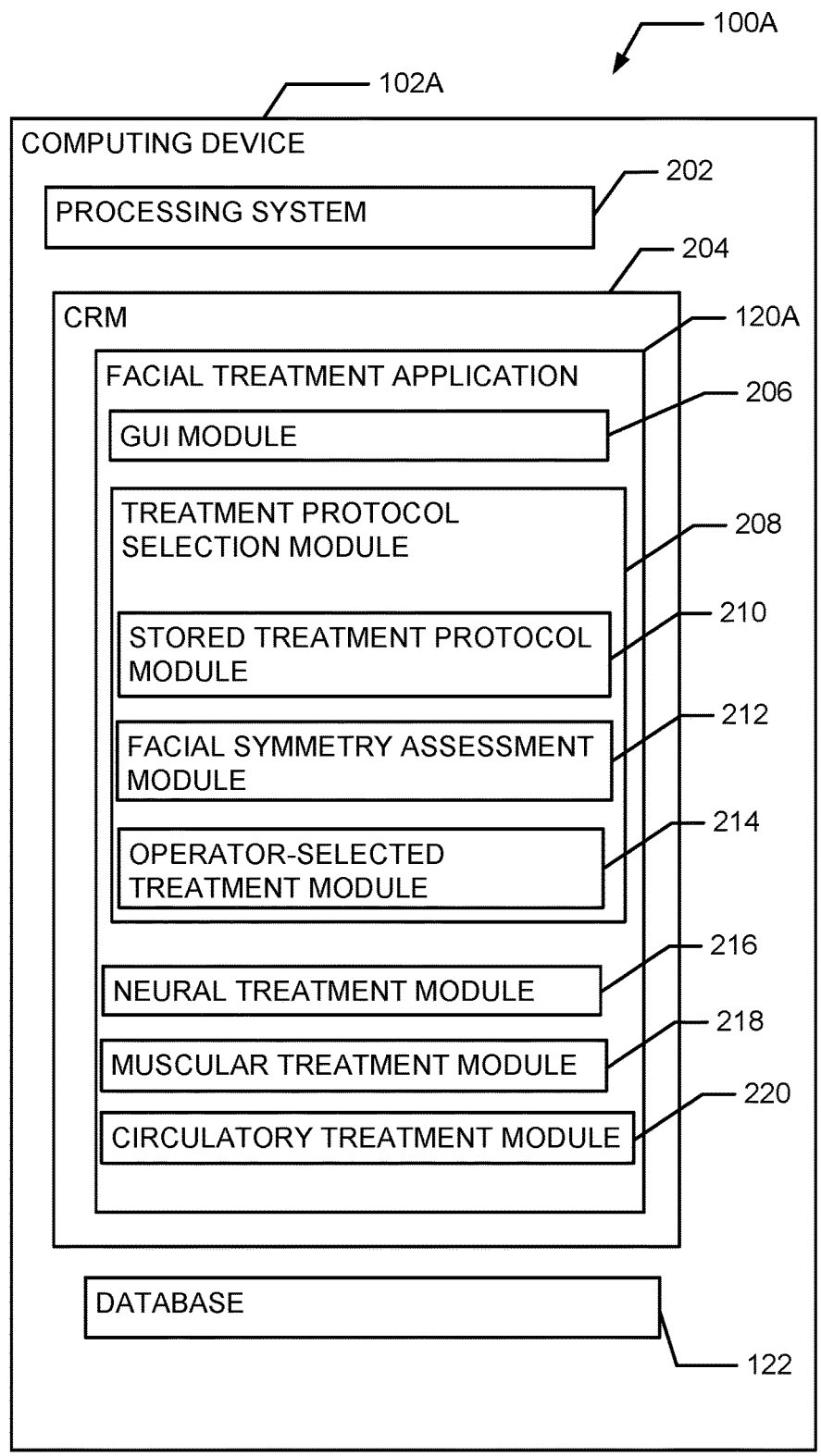
FIG. 2 is a block diagram of a facial treatment application configured to operate on a computing device.

FIG. 2 is a block diagram depicting a facial treatment application 120A executing on a computing device 102A. According to one aspect, the computing device 102A includes a processing system 202 that includes one or more processors or other processing devices. The processing system 202 executes the facial treatment application 120A to select and provide a treatment of the facial tissues of a patient 110 (not shown) using the facial stimulator instrument 106 (not shown) and/or acoustic oscillator 108 (not shown). The facial treatment application 120A may further obtain and analyze facial images of the patient 110 using one or more cameras 104 (not shown) to assess the condition of the patient's facial tissues. A database 122 may be accessed by the facial treatment application 120A during execution to provide information including, but not limited to: stored facial images and other stored patient information, stored treatment protocols, and stored instrument control settings.

In an aspect, the computing device 102A includes a computer readable medium ("CRM") 204 configured with the facial treatment application 120A. The facial treatment application 120A includes instructions or modules that are executable by the processing system 202 to enable a user to implement a treatment to the facial tissues of a patient 110.

The CRM 204 may include volatile media, nonvolatile media, removable media, non-removable media, and/or another available medium that can be accessed by the computing device 102A. By way of example and not limitation, computer readable medium 204 comprises computer storage media and communication media. Computer storage media includes nontransient memory, volatile media, nonvolatile media, removable media, and/or non-removable media implemented in a method or technology for storage of information, such as computer readable instructions, data structures, program modules, or other data. Communication media may embody computer readable instructions, data structures, program modules, or other data and include an information delivery media or system.

A GUI module 206 transmits one or more GUIs 116 (not shown) to the display 112 (not shown). As described above, the operator of the system 100 interacts with one or more GUIs received from the computing device 102A to review treatment protocols, enter data and make menu selections used to implement a treatment using the system 100. Examples of screen shots of the one or more GUIs 116 in various aspects are provided herein below.

In an aspect, the facial treatment application 120A includes a treatment protocol selection module 208 for selecting an appropriate treatment protocol based on stored patient data, analysis of the patient's facial tissues, selection from a stored menu of treatment protocols, and/or specification of a treatment protocol by the operator of the system 100. The facial treatment application 120A may further include modules to implement a particular treatment on the facial tissues of a patient, including a neural treatment module 216, a muscular treatment module 218, and a circulatory treatment module 220. Detailed descriptions of each of the modules of the facial treatment application 120A are provided herein below.

III. Treatment Protocol Selection Module

The treatment protocol selection module 208 selects one or more treatment protocols to be performed on the facial tissues of a patient 110. The one or more treatment protocols may be selected from a stored menu of treatment protocols, a treatment protocol may be determined based on an assessment of the condition of the patient's facial tissues, or a treatment protocol may be specified by the operator of the system 100A. The treatment protocol selection module 208 in an embodiment may include a stored treatment protocol module 210, a facial symmetry assessment module 212, and an operator-selected treatment module 214.

a. Stored Treatment Protocol Module

Figure 3:
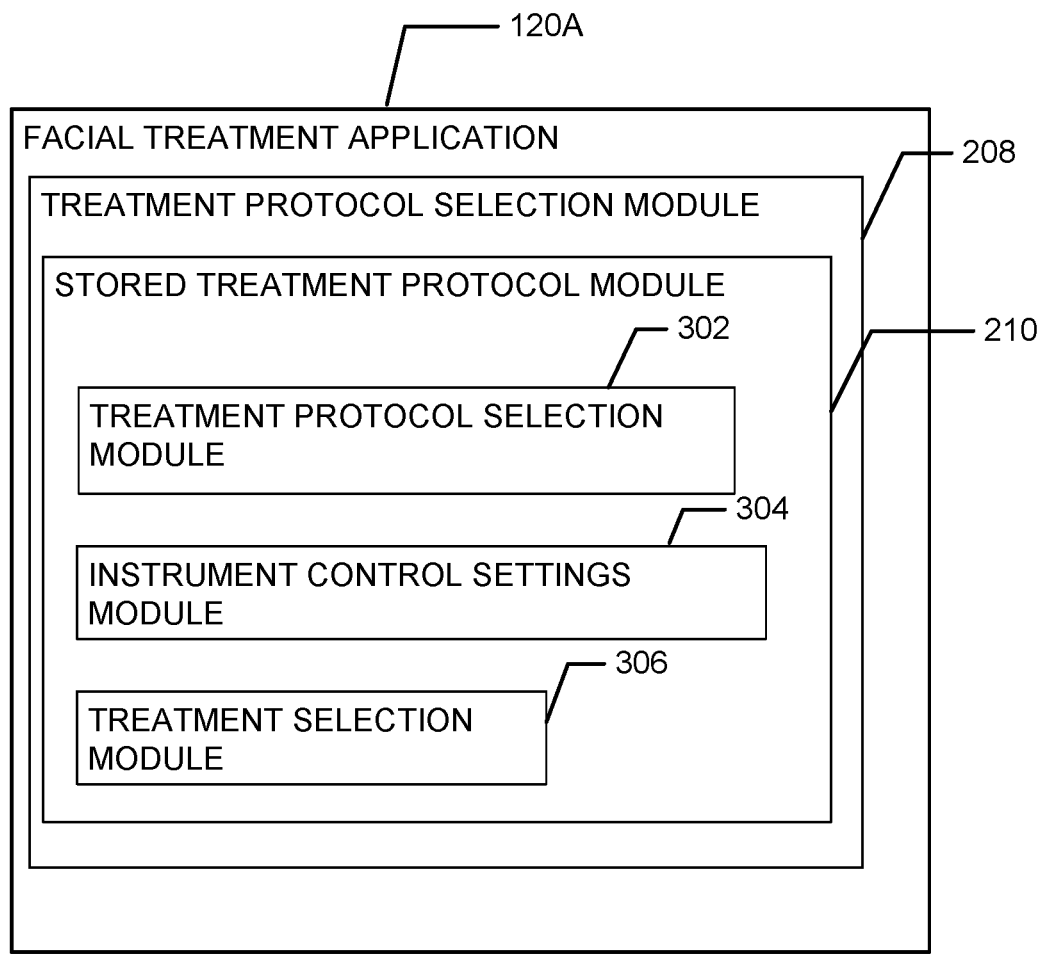
FIG. 3 is a block diagram of a stored treatment protocol selection module of a facial treatment application.

The stored treatment protocol module 210 is configured to generate a menu of treatment protocols from which the operator may select a treatment for the facial tissues of the patient, as well as to implement the treatment protocol selected from the menu by the operator. In an embodiment, illustrated in FIG. 3, the stored treatment protocol module 210 may include a treatment protocol selection module 302, an instrument control settings module 304, and a treatment selection module 306. The treatment protocol selection module 302 generates a menu of treatment protocols and displays this menu to the operator via the GUI 116 (not shown). The menu of treatment protocols may be a list of standard treatments arranged into one or more organizational schemes including, but not limited to: region of face, type of facial tissue, type of facial tissue disorder, treatments previously performed on the patient, desired results of a facial tissue treatment, and a schedule of planned treatments for a patient. In an embodiment, the stored treatment protocol module 210 may access stored patient information from the database 122 (not shown) in order to generate the menu of patient-specific treatment protocols. For example, the stored treatment protocol module 210 may retrieve one or more patient-specific treatment protocols 130 from the database 122, shown on FIG. 1, for use in the menu of treatment protocols.

Referring back to FIG. 3, the stored treatment protocol module 208 may further include an instrument control settings module 304 configured to determine the appropriate settings for one or more instruments used to implement a treatment protocol selected by the operator from the menu of treatment protocols using the treatment protocol selection module 302. As illustrated in FIG. 1, the system 100 may administer treatments with one or more instruments including, but not limited to, a facial stimulator instrument 106 and an acoustic oscillator 108. In an embodiment, the instrument control settings module 304 may determine one or control settings for the facial stimulator instrument 106 including, but not limited to: preload tissue compression force, magnitude and frequency of a percussive impact, as well as power and waveform of an electrical stimulation to be applied to the facial tissue. In another embodiment, the instrument control settings module 304 may determine one or more control settings for the acoustic oscillator 108 including, but not limited to: magnitude and frequency of an acoustic pulse to be applied to the facial tissue. A more detailed description of additional instrument control settings that may be determined by the instrument control settings module 304 are provided herein below.

The stored treatment protocol module 208 may further include a treatment selection module 306. Once the treatment protocol has been determined by the treatment protocol selection module 302 and the instrument control settings have been initialized by the instrument control settings module 304, the treatment selection module 306 may initiate the execution of one or more of the treatment modules used to implement a treatment on a muscular facial tissue, a facial nerve, and/or a facial circulatory vessel.

Figure 4:
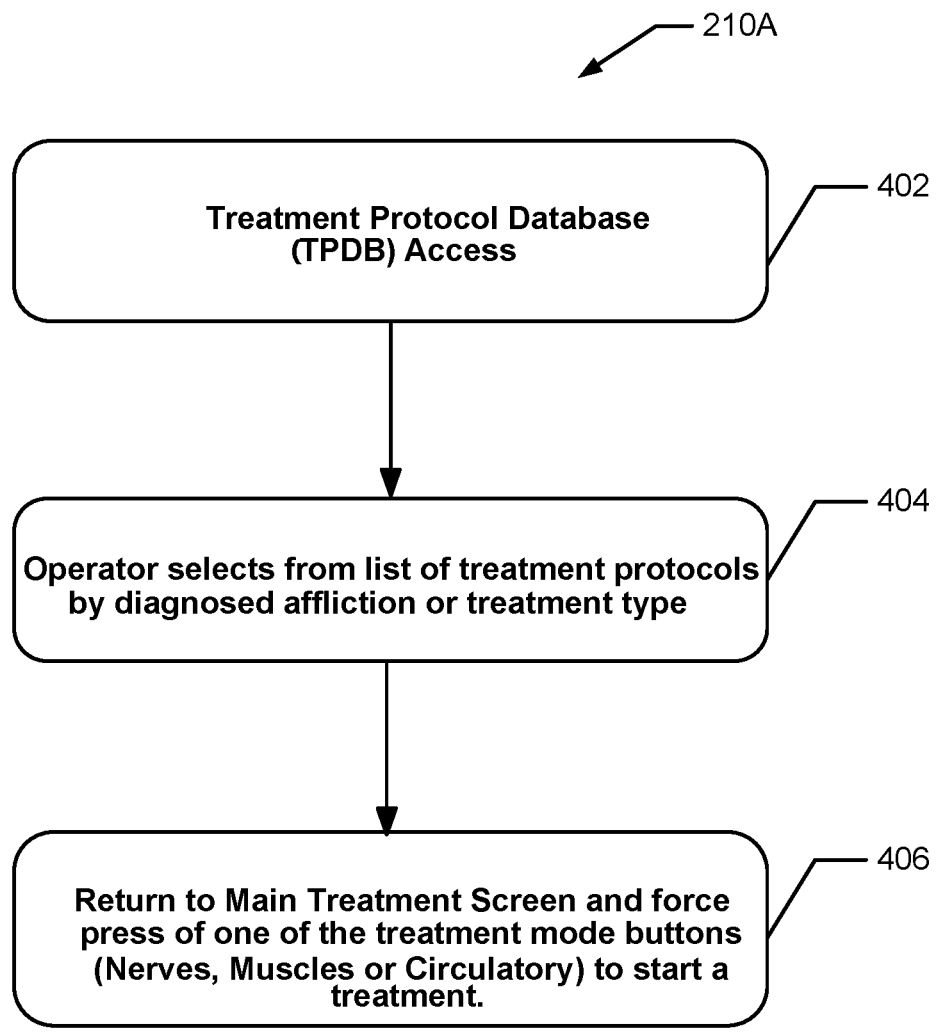
FIG. 4 is a flow chart illustrating an embodiment of a stored treatment protocol selection module.

FIG. 4 is a flow chart illustrating a series of actions taken by the operator of the system in an embodiment of the stored treatment protocol module 208. In this embodiment, the operator of the system makes a selection to access the stored treatment protocol database at step 402. The operator then selects a desired treatment protocol from the displayed list of stored treatment protocols at step 404. Once a treatment protocol has been selected, the operator then selects one of the treatment modules for execution at step 406. At step 406, the treatment modules available for execution are limited by the stored treatment protocol module 208 to include only those treatment modules that are appropriate for the selected treatment protocol.

b. Facial Symmetry Assessment Module

Referring back to FIG. 2, the facial treatment application 120 further includes a facial symmetry assessment module 212 configured to assess the condition of the facial tissues of the patient and determine a recommended treatment protocol based on the assessed condition of the facial tissues. The facial symmetry assessment module 212 may analyze one or more facial images obtained by a 2D or 3D camera (not shown) in order to assess the degree of symmetry between corresponding left and right facial features or facial landmarks. In this embodiment, if the analysis of the one or more facial landmarks indicates sufficient asymmetry between corresponding left and right facial landmarks, the facial treatment application 120 may recommend one or more treatment protocols involving facial tissues associated with the asymmetrical facial landmark.

Figure 5:
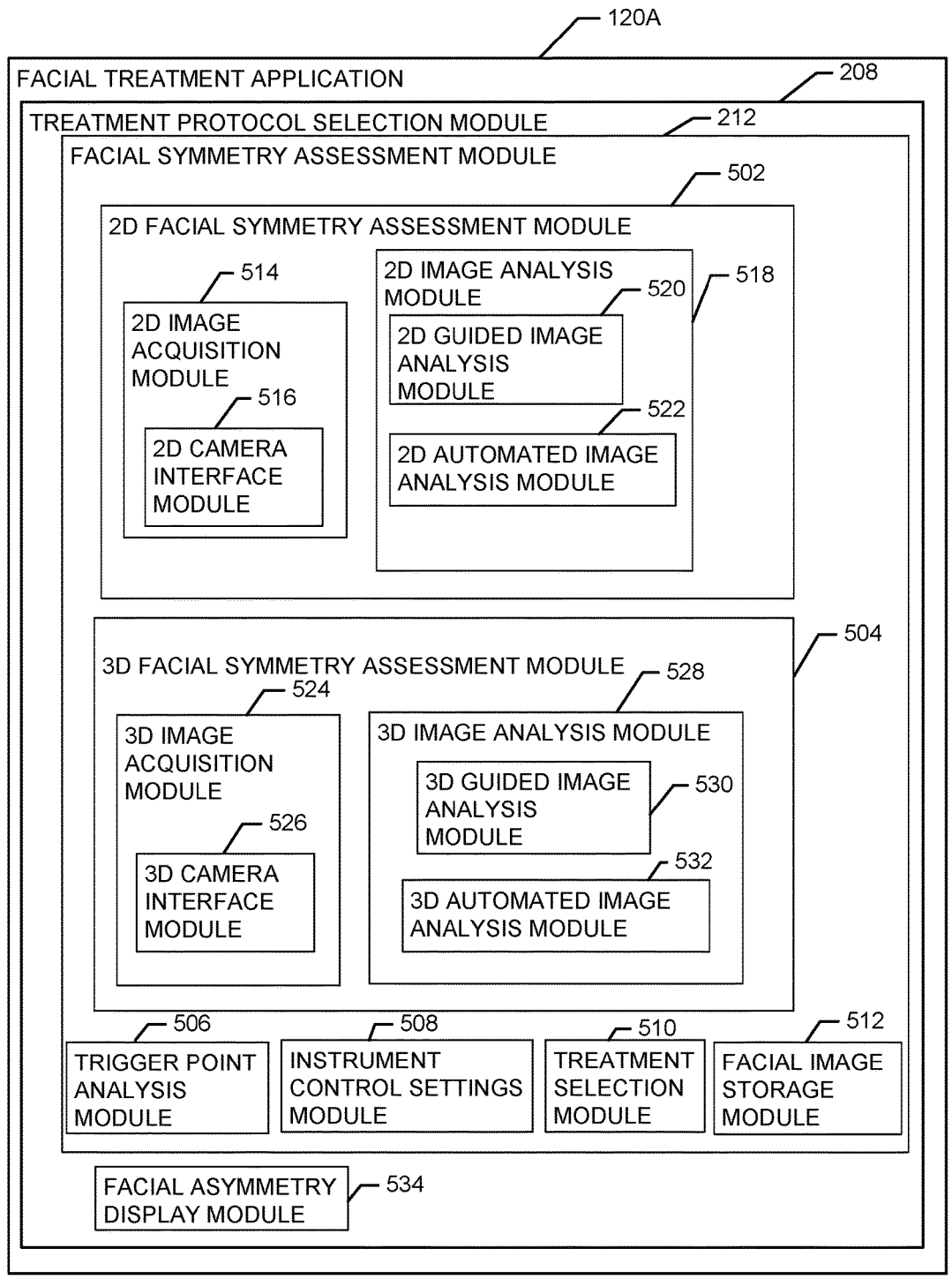
FIG. 5 is a block diagram of a facial symmetry assessment module of a facial treatment application.

FIG. 5 is a block diagram illustrating an embodiment of the facial symmetry assessment module 212. In this embodiment, the facial symmetry assessment module 212 may include a 2D facial symmetry assessment module 502 configured to obtain and analyze facial images using a 2D camera. The facial symmetry assessment module 212 may further include a 3D facial symmetry assessment module 504 configured to obtain and analyze facial images using a 3D camera. A trigger point analysis module 506 may implement further assessment of selected facial tissues identified by the 2D facial symmetry assessment module 502 or 3D facial symmetry assessment module 504 using other instruments (not shown) such as the facial stimulator instrument 106 and/or the acoustic oscillator 108. Once a recommended treatment protocol has been identified, the instrument control settings module 508 provides the appropriate instrument control settings and the treatment selection module 510 directs the initiation of one or more treatment protocols. The 2D and/or 3D facial images obtained before and/or after treatment, as well as any associated patient data and/or treatment protocol information may be stored in the database 206 (not shown) by the facial image storage module 512.

i. 2D Facial Symmetry Assessment Module

Figure 6:
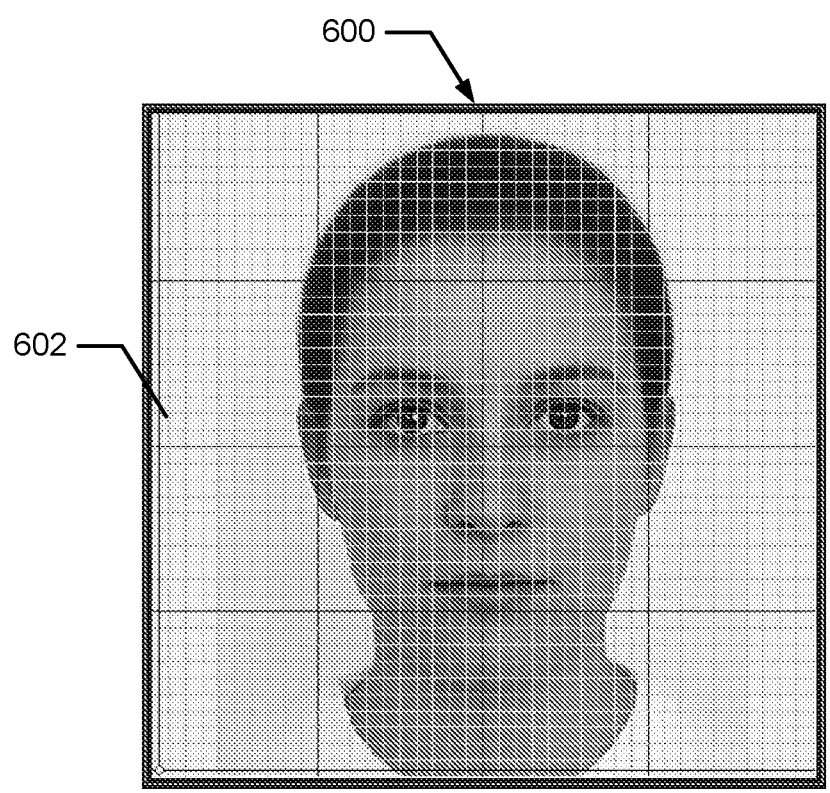
FIG. 6 is a 2D facial image including a superimposed grid.

The 2D facial symmetry assessment module 502 may include a 2D image acquisition module 514 configured to obtain a 2D facial image of the patient. A 2D camera interface module 516 may operate the camera via the input device 114 and display 112 to obtain the 2D facial image. The patient is placed in a fixed position and a 2D image may be obtained using inputs from the operator captured via a GUI or other interface on the input device 114. The positioning of the patient's face within the frame of the facial image, the degree of brightness and/or contrast, the resolution of the obtained image, and any other parameters relevant to the 2D facial image may be determined automatically by the 2D image acquisition module 514. Alternatively, the 2D image acquisition module 514 may generate a GUI 116 (not shown) configured to guide the operator through the acquisition of a 2D image of the patient's face. The 2D facial image 600 of the patient may include a superimposed grid 602, as illustrated in FIG. 6, to aid in the analysis of facial symmetry of the patient.

A standard 2D facial image may be obtained by placing the patient in a standard position using known methods such as immobilizing the patient's head in a standardized chair or rig. In a standard 2D facial image, the scaling of distances between facial landmarks in the facial image and the actual distances is a known standard scale; in addition, the horizontal and/or vertical orientation of the facial image may be obtained in a standardized and repeatable manner. Alternatively, a non-standard 2D facial image may be obtained without the use of standardized rigs. The non-standard 2D facial image may further contain scaling elements such as rulers or reference lines within the background of the 2D facial image. Known image processing techniques such as scaling and axis rotation may be used to convert a non-standard 2D facial image into a standard 2D facial image to facilitate subsequent analysis. In yet another embodiment, relative displacements of the facial landmarks may be used to assess facial symmetry, obviating the need to obtain a standardized 2D facial image. For example, the separation of the pupils of the eye as a fraction of the maximum head width may be used as a relative measurement.

The 2D facial symmetry assessment module 502 may further include a 2D image analysis module 518 configured to assess the symmetry of selected facial landmarks from the 2D facial image. A 2D guided image analysis module 520 may perform an analysis of the 2D facial image by guiding the operator through a series of image analysis steps via a GUI 116 (not shown). An automated assessment of the 2D facial image may also be performed using the 2D automated image analysis module 522. In various embodiments, a guided image analysis and/or an automated image analysis may be performed on the 2D facial image. In an aspect, the 2D automated image analysis module 522 may automatically identify and compare facial landmarks to determine asymmetries in a manner similar to the methods implemented by the analysis modules of the 2D guided image analysis module 520, described herein below. In another aspect, the 2D facial symmetry assessment module 502 may assess the symmetry of selected facial landmarks using a combination of a guided image analysis and an automated analysis.

Figure 7:
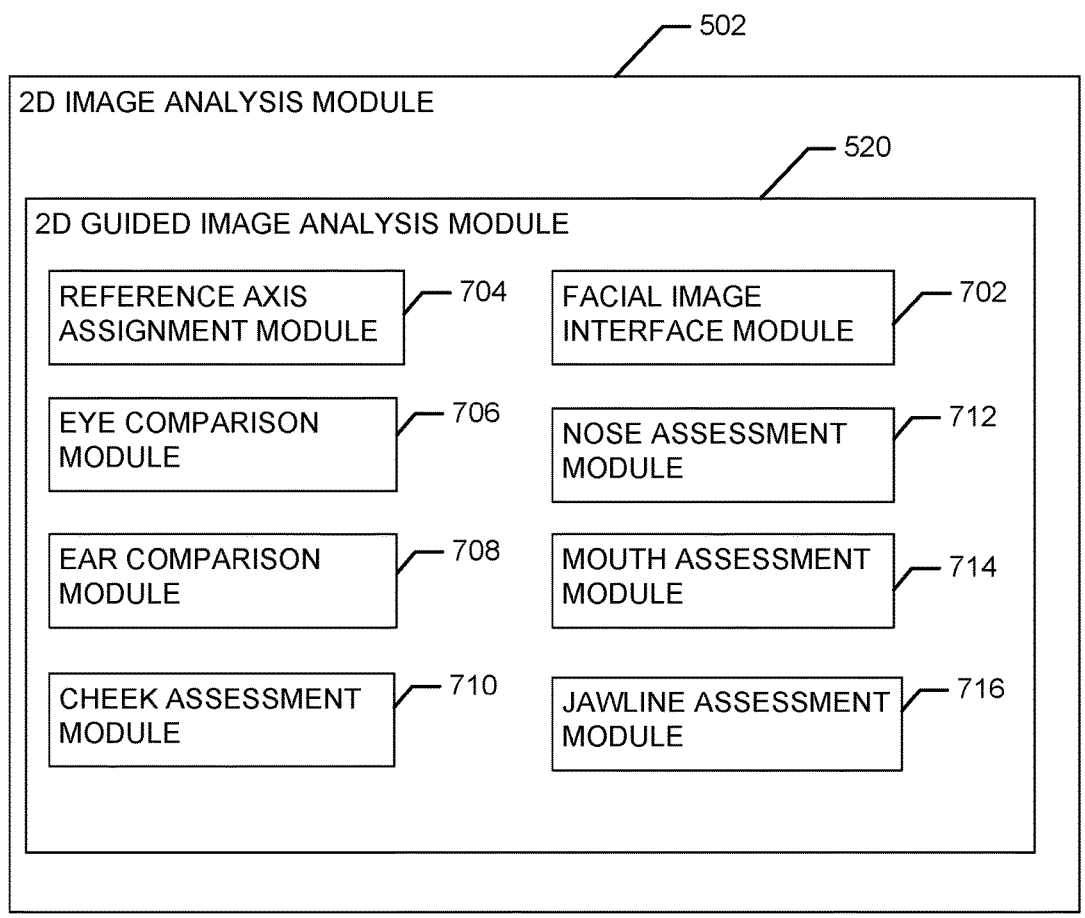
FIG. 7 is a block diagram of a 2D guided image analysis module.

FIG. 7 is a block diagram illustrating an embodiment of the 2D guided image analysis module 520. In this embodiment, the operator identifies at least one facial landmark on a 2D facial image displayed within an facial image analysis GUI 800 (not shown) generated by a facial image interface module 702. Facial landmarks, as defined herein, refer to facial features that are identifiable from a facial image that may be used in the assessment of facial symmetry. Non-limiting examples of facial landmarks include: an eye feature such as a pupil, an iris, a lateral corner, or a medial corner, an eyebrow; an ear feature such as an earlobe (lobule), a helix, or a tragus; a nose feature such as bridge of a nose, a nostril, or a tip of a nose; a chin or jaw feature such as chin cleft or a mandibular joint; a mouth feature such as a mouth corner; a forehead feature; a facial wrinkle; or any other facial feature that is readily located on a 2D or 3D facial image.

Figure 8:
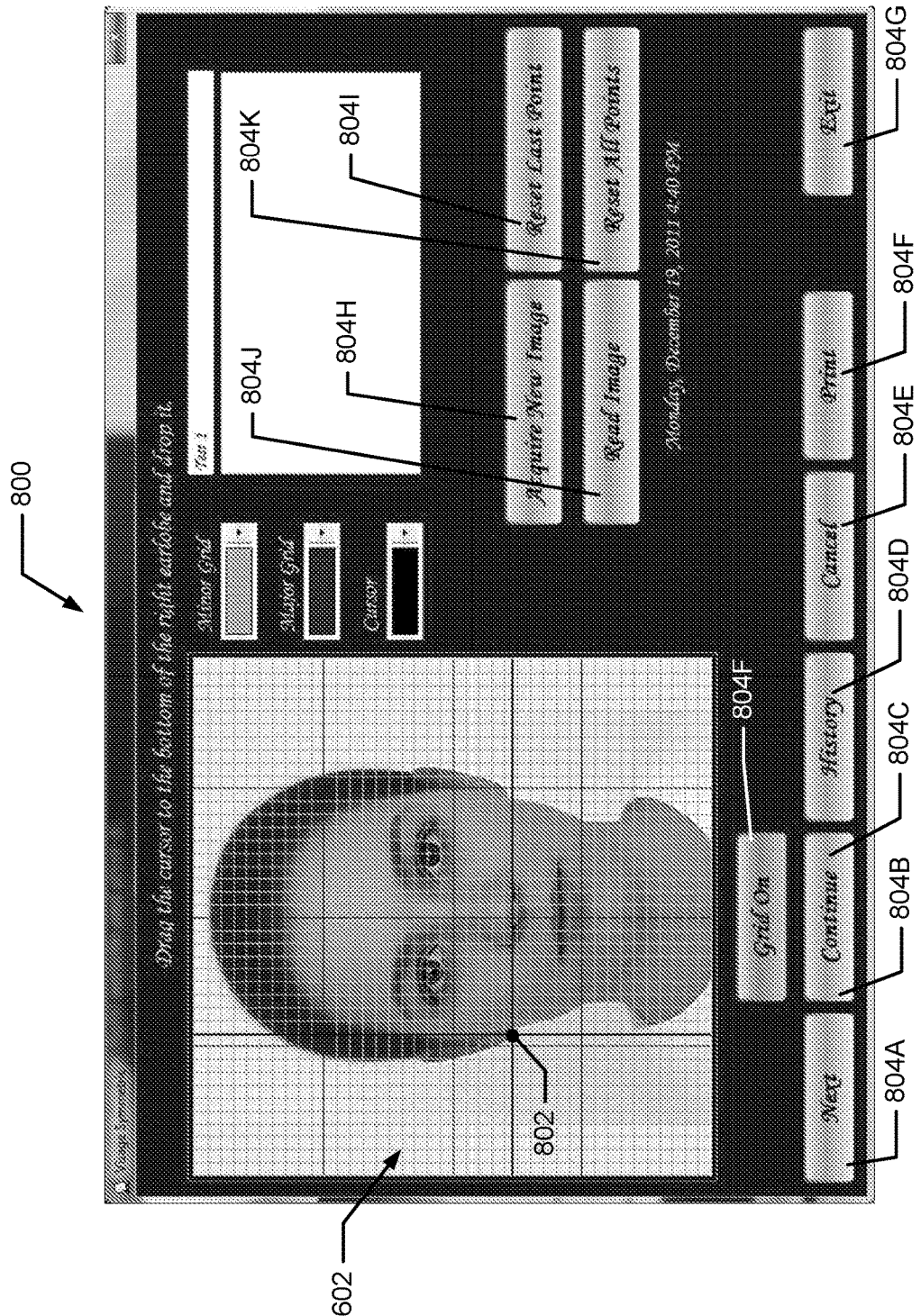
FIG. 8 is an embodiment of a facial image display.

An example of an image analysis GUI 800 generated by the facial image interface module 702 is illustrated in FIG. 8. In this example, the operator has identified a facial landmark 802 on the 2D facial image 600 corresponding to the bottom of the patient's right earlobe. The facial landmarks identified by the operator may be represented as a dot or other symbolic representation including, but not limited to, a square or other geometric shape, a cross-hair, or any other representation easily visible by the operator. The image analysis GUI 800 may also include one or more control buttons 804A-804K that may be activated to perform a desired action associated with the acquisition and analysis of a 2D image. The control buttons 804A-804K may be activated and/or deactivated using any known user input method including clicking on the control button using a mouse-type input device, and/or touching a control button 804 displayed on a touch screen input device.

As shown in FIG. 8, the control buttons 804A-804K may control a variety of functions associated with the guided 2D image analysis. A 2D image may be acquired using the 2D camera or a stored facial image may be retrieved from the database by activating control buttons 804H and 804K, respectively. The operator may sequentially identify additional facial landmarks by activating control button 804A. An operator-selected facial landmark, such as the bottom of the right earlobe 802, may be revised by activating control button 804I, or all operator-selected facial landmarks may be revised by activating control button 804K. A history of all operator-identified facial landmarks may be displayed by activating control button 804D and the current image analysis GUI 800 may be printed by activating control button 804E. The operator may continue on to the assessment of facial symmetry by activating control button 804C, cancel the execution of the 2D image analysis module by activating control button 804E, or exit from the facial treatment application 120 altogether by activating control button 804G.

Referring back to FIG. 7, the 2D guided image analysis module 520 further includes a number of analysis modules 704-718 configured to compare the facial landmarks identified by the operator using the facial image interface module 702 and assess the symmetry of corresponding left and right facial landmarks. For example, the facial landmark 802 associated with the bottom of the patient's left earlobe may be compared to the facial landmark associated with the bottom of the patient's right earlobe to assess the symmetry of the patient's earlobes.

A reference axis assignment module 704 may determine a location on the 2-D image corresponding to a reference axis. A reference axis may be used to provide a standard geometrical reference from which all distances such as height or lateral separation from a facial axis of symmetry may be determined. For example, the patient's nose centerline may be assigned to a reference vertical axis, and a line perpendicular to the patient's nose centerline may be assigned to a reference horizontal axis. Other facial landmarks of the patient including, but not limited to, eye pupils or any other operator-identified facial landmarks may be used to establish one or more reference axes. The reference axes may be assigned relative to the patient's face, as discussed herein above, or relative to an absolute horizontal and/or vertical axis. For example, the patient's facial image may include a reference scale, such as a ruler oriented horizontally and/or a ruler oriented vertically. In this example, the distances separating facial landmarks may be expressed in terms of absolute distances, and/or in terms of distances relative to other landmark features. For example, the location of the bottom of the right earlobe may be expressed as a horizontal and vertical distance in cm relative to an origin specified by the operator. Alternatively, the location of the bottom of the right earlobe may be expressed as a relative distance such as the % of the pupil separation distance. Any known reference axis system including, but not limited to, a Cartesian coordinate system, a polar coordinate system, and a conformal grid coordinate system may be used in the system 100.

An eye comparison module 706 compares the location of a facial landmark associated with the left eye and the location of a facial landmark associated with the right eye of the patient. For example, the eye comparison module 706 may compare the lateral distance of the right pupil and the left pupil relative to the bridge of the nose. In another example, the location of the corners of the left eye relative to the left eyebrow may be compared to the locations of the right eye corners relative to the right eyebrow. In yet another example, the location and extent of the skin flap above the left and right eyelids may be compared. In another additional example, the corneal reflectivity of the left and right eyes may be compared.

An ear comparison module 708 compares the location of a facial landmark associated with the left ear and the location of a facial landmark associated with the right ear of the patient. For example, the location of the left and right earlobe of the patient may be compared.

A cheek assessment module 710 compares the location of a facial landmark associated with the left cheek and the location of a facial landmark associated with the right cheek of the patient. For example, the location of the crease in the skin between the side of the nose and cheek on the left and right sides of the patient's face may be compared.

A nose assessment module 712 assesses the location of a facial landmarks associated with the nose and the location of other facial landmarks of the patient. For example, the location of the nose centerline may be compared to the forehead centerline or the center of the chin of the patient.

A mouth assessment module 714 compares the location of facial landmarks associated with the mouth and the location of other facial landmarks of the patient. For example, the location and angle of the left and right corners of the mouth of the patient may be compared. In another example, the shape, thickness, and/or length of the lips on the left and right sides of the center of the mouth may be compared.

A jawline assessment module 716 compares the location of facial landmarks associated with the jaw on the left and right sides of the face of the patient. For example, the location of the left and right corners of the chin of the patient, or angles of the left and right jawline margins of the patient may be compared.

Any differences between the left and right locations or angular orientations of any facial landmarks described herein above, as calculated by the comparison/assessment modules 706-716, may indicate an asymmetrical condition of a facial landmark. Referring to FIG. 5, a facial asymmetry display module 534 may display any asymmetries between the left and right facial landmarks to the operator using the display 112 (not shown) after the completion of the symmetry analysis of the 2D facial image.

ii. 3D Facial Symmetry Assessment Module

Referring back to FIG. 5, the facial asymmetry assessment module 212 may further include a 3D facial symmetry assessment module 504 configured to obtain and analyze a 3D facial image to determine asymmetries between selected facial landmarks using modules and methods similar to the corresponding modules and methods of the 2D facial symmetry assessment module 502. The 3D facial symmetry assessment module 504 includes a 3D image acquisition module 524 configured to obtain a 3D facial image using a 3D camera, stereoscopic camera, or any other 3D image recording device or scanner operated using a 3D camera interface module 526.

Figure 9:
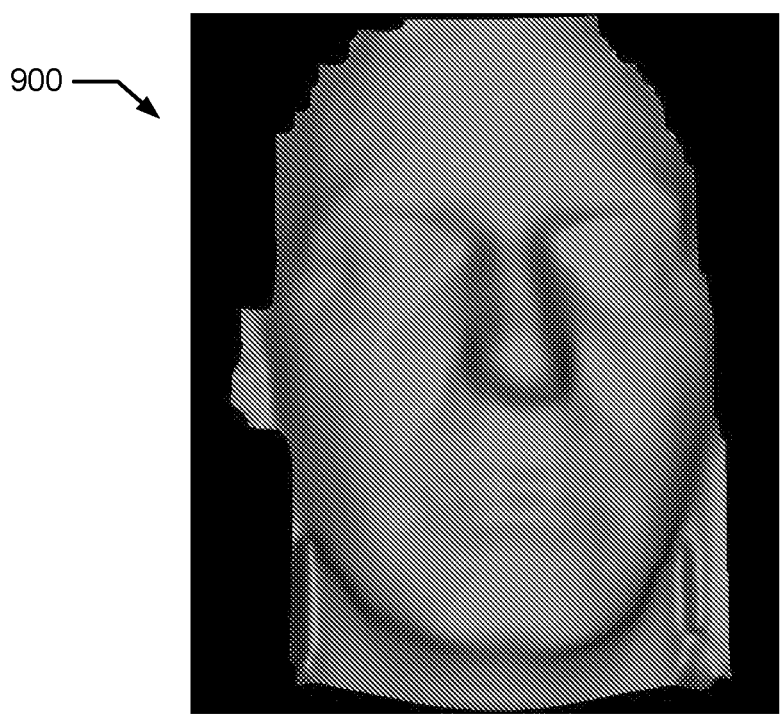
FIG. 9 is a 3D facial image.

An example of a 3D facial image 900 obtained using the 3D image acquisition module 524 is illustrated in FIG. 9. In an aspect, the 3D facial image 900 may be displayed in the form of a virtual 3D representation that may be rotated about any selected axis to facilitate the 3D image analysis. In another aspect, the 3D facial image 900 may be displayed in the form of a series of 2D representations corresponding to different views of the 3D images including, but not limited to front, side, back, perspective, top, and/or bottom views and/or any other 2D representation that may facilitate the 3D facial image analysis.

Referring back to FIG. 5, the 3D image analysis module 528 includes a 3D guided image analysis module 530 and a 3D automated image analysis module 532. The 3D guided image analysis module 530 performs a guided 3D image analysis on the 3D facial image 900 in which the operator is prompted by a GUI to identify a series of facial landmarks on the 3D facial image 900, which are subsequently analyzed to determine numerical degrees of asymmetry. The 3D image analysis may assess asymmetries of corresponding left/right facial landmarks with respect to a plane of symmetry. For example, the plane of symmetry may correspond to a midsagittal plane passing through the midline of the nose of the patient. The facial landmarks analyzed by the 3D guided image analysis module 530 are similar to those described herein above in connection with the facial landmarks analyzed by the 2D guided image analysis module 520. A similar 3D image analysis may be performed using automated facial landmark recognition and analysis methods using the 3D automated image analysis module 532.

The degree of asymmetry between corresponding left/right facial landmarks determined by the 3D facial asymmetry assessment module 504 may be quantified using similar methods to those described herein above in connection with the degree of asymmetry resulting from the 2D image analysis. In addition, the 3D degree of asymmetry for each facial landmark may be displayed using the facial asymmetry display module 534 using methods similar to those described herein above for the display of the 2D degrees of asymmetry.

Figure 10:
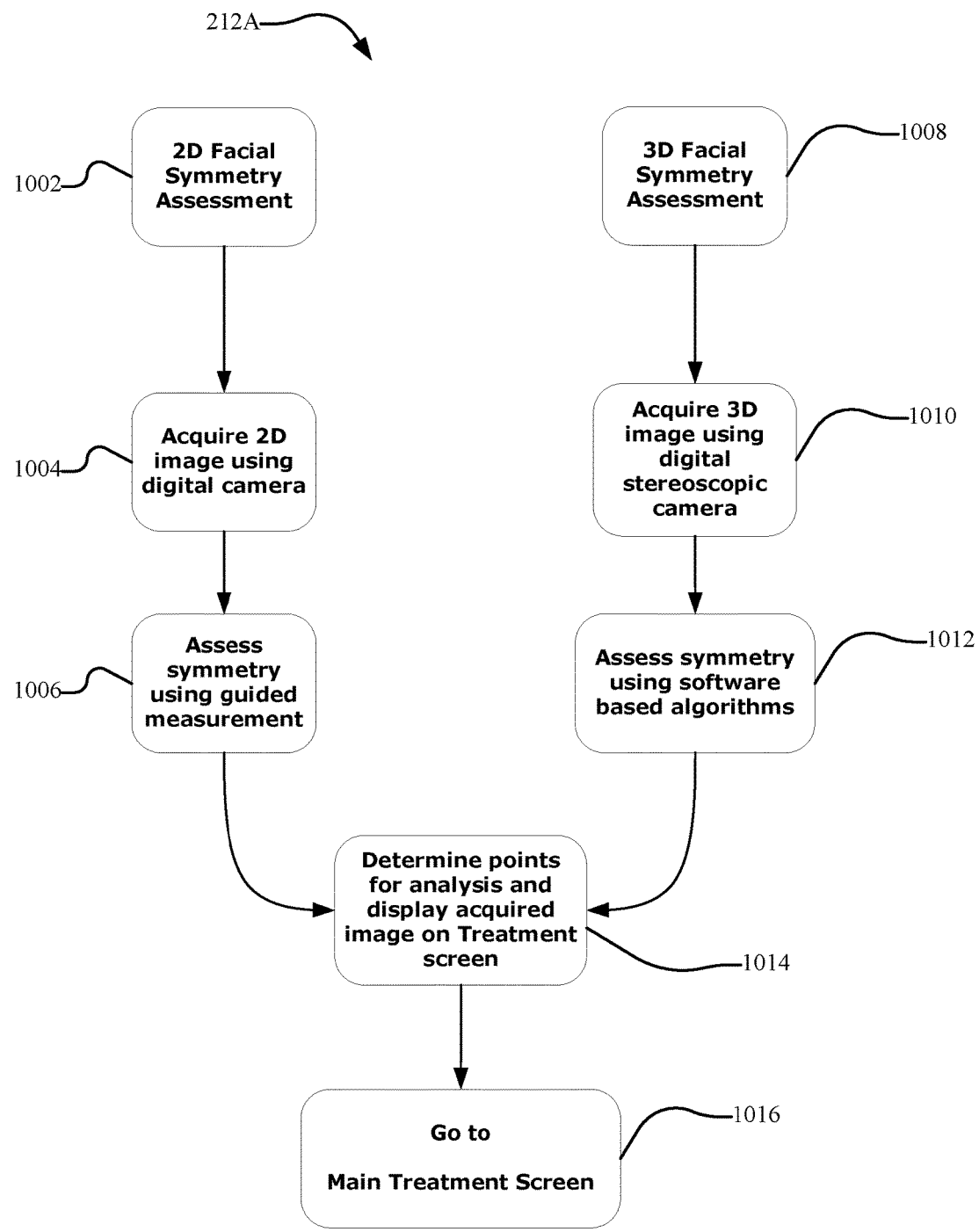
FIG. 10 is a flow chart illustrating an embodiment of a facial symmetry assessment module.

FIG. 10 is a flowchart illustrating an embodiment of a facial symmetry assessment module 212A. In this embodiment, the acquisition and analysis of a 2D facial image may be selected at step 1002. The 2D image may be obtained at step 1004 and a guided symmetry assessment of the 2D image may be performed at step 1006. Alternatively, or in addition to the 2D image analysis, the acquisition and analysis of a 3D facial image may be selected at step 1008. The 3D image may be obtained at step 1010 and an automated symmetry assessment of the 3D image may be performed at step 1012. Facial landmarks having a sufficiently high degree of asymmetry may be selected for display and further analysis at step 1014. The operator may end the facial symmetry analysis at step 1016 and return to a main treatment screen to select additional actions such as administering a treatment to the facial tissues of the patient.

iii. Trigger Point Analysis Module

Referring back to FIG. 5, the numerical asymmetries determined by the facial symmetry assessment module 502 may indicate a particular treatment protocol for one or more facial tissues. The numerical asymmetries may also identify facial landmarks that may be further analyzed using the trigger point analysis module 506. For example, if the left corner of a patient's mouth is vertically higher than the corresponding right corner, this asymmetry may indicate an asymmetry in the muscle tone, neural activation patterns, and/or vascularization associated with the positioning of the corners of the patient's mouth.

The trigger point analysis module 506 may further assess the condition of the facial tissues of the patient by measuring tissue characteristics including, but not limited to, the galvanic response of a facial tissue, the response of the tissue to an applied force impulse, or any other aspect of the facial tissue related to, or correlated with, the health and condition of the facial tissue. The trigger point analysis module 506 may use any known instrument to perform an additional assessment of the condition of the facial tissues including, but not limited to, a facial stimulator instrument as described herein below, an electromyographic electrode, or any other known measurement device appropriate for measurement of a facial tissue characteristic.

Figure 11:
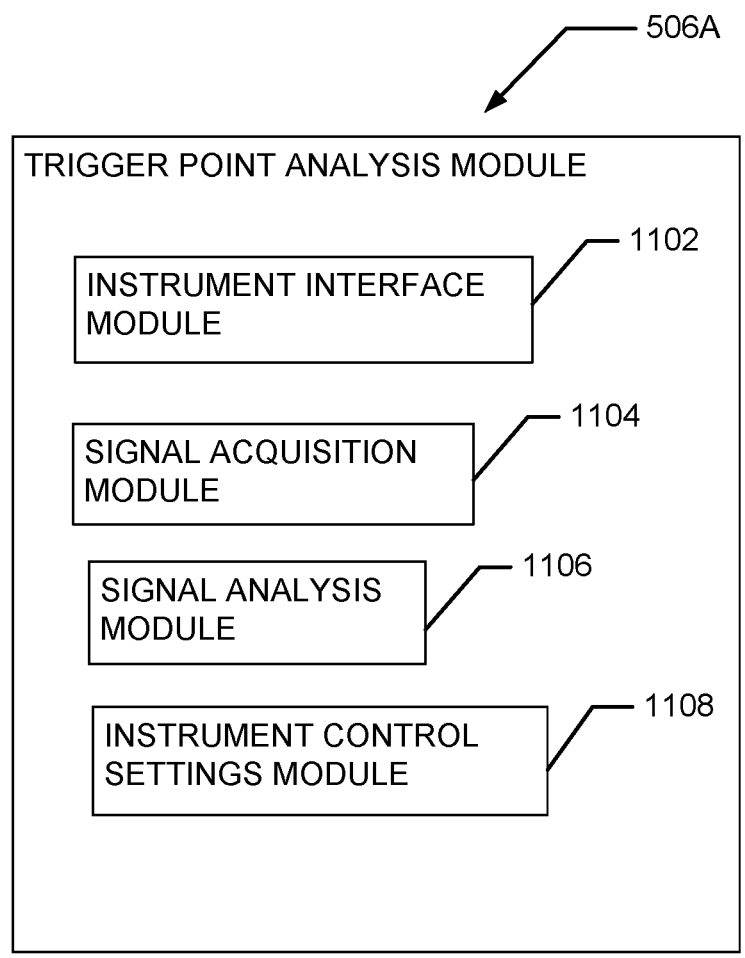
FIG. 11 is a block diagram of a trigger point analysis module.

FIG. 11 is a block diagram illustrating an embodiment of a trigger point analysis module 506A. The trigger point analysis module 506A includes an instrument interface module 1102 to provide a GUI or other interface used by the operator to conduct measurements using one or more devices, a signal acquisition module 1104 to record a measurement signal obtained by the one or more devices, a signal analysis module 1106 to process the signal from the device to determine the condition of the facial tissue, and an instrument control settings module 1108 to provide instrument control settings such as power settings, frequency of percussive impacts, voltage and/or waveform of an applied electrical pulse, frequency of applied acoustic pulses, and any other parameter associated with a selected treatment protocol.

The trigger point analysis module 506A may be configured to guide the operator through the steps of locating a facial landmark, initializing an instrument for measuring a characteristic of a facial tissue in the vicinity of the facial landmark, and obtaining one or more measurements using the instrument. The operator may be guided through measurements for one or more facial landmarks using the trigger point analysis module 506A. The trigger point analysis module 506A may process the measurements of the characteristics of each facial landmark in combination with that landmark's degree of asymmetry to determine a recommended treatment protocol.

Figure 12:
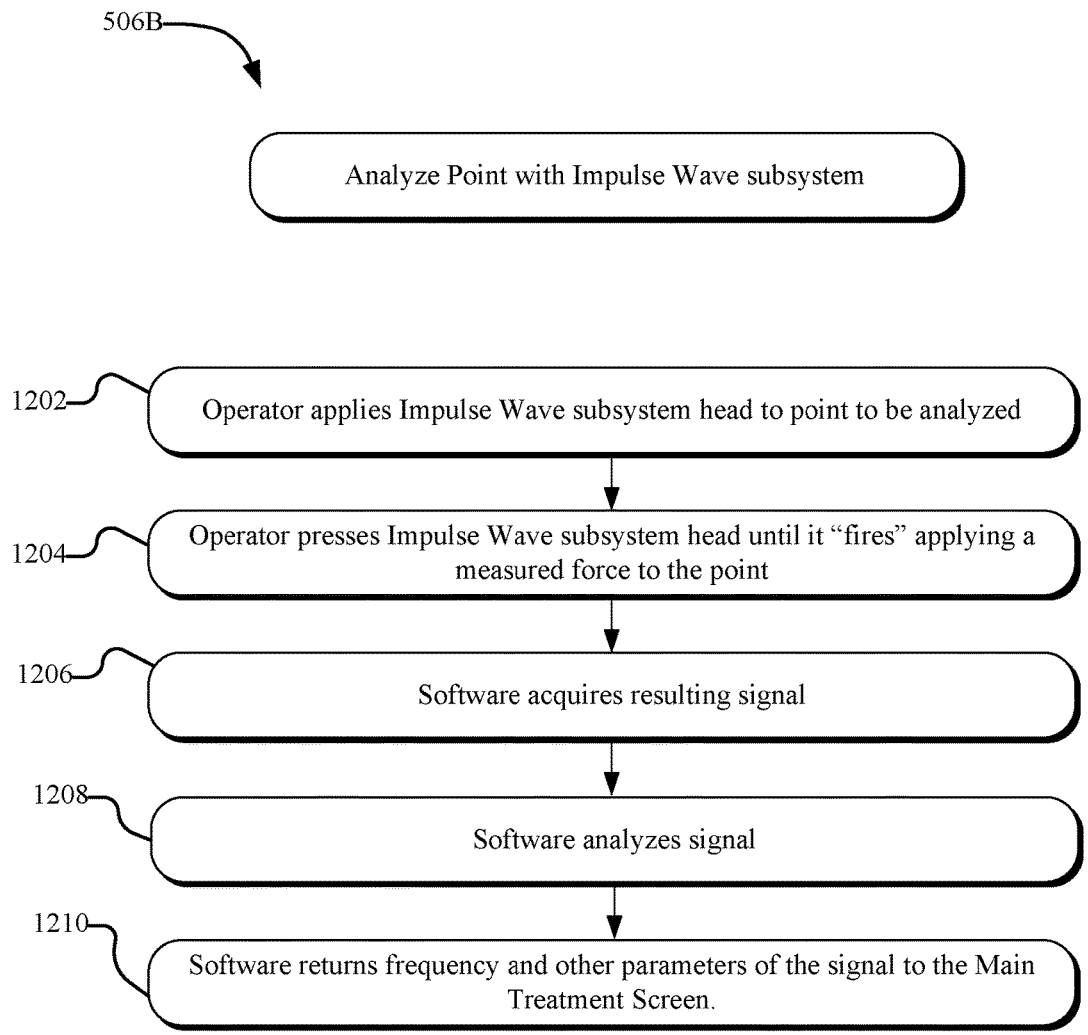
FIG. 12 is a flow chart illustrating an embodiment of a trigger point analysis module.

FIG. 12 is a flow chart illustrating an embodiment of a trigger point analysis module 506B. In this embodiment, a facial stimulator instrument 106, referred to as an Impulse Wave subsystem in FIG. 12, is used to measure the reaction of a tissue to an applied force impulse. The facial stimulator instrument 106 is situated at a specified facial landmark at step 1202. In an aspect, the specified facial landmark may be identified as a landmark associated with a relatively high degree of asymmetry by the facial symmetry assessment module 212. The facial landmark to be subjected to trigger point analysis may be displayed to the operator of the system 100 via the display 112. A force impulse is applied to the facial tissue at step 1204 and a signal encoding the reaction of the facial tissue to the applied force impulse is acquired by the signal acquisition module 1104 at step 1206. The signal analysis module 1106 analyzes the signal at step 1208, and the instrument control settings are determined by the instrument control settings module 1108 at step 1210. The instrument control settings are used by one or more treatment modules 216-220 to provide a treatment to a facial tissue of the patient.

In an aspect, the signal analysis module 1106 may analyze any one or more characteristics of the facial tissue in response to the force impulse applied by the facial treatment instrument 106 including, but not limited to, the waveform of the facial tissue response. Non-limiting aspects of the waveform of the facial tissue response that may be analyzed by the signal analysis module 1106 include the peak or maximum amplitude of the waveform, the peak time, the rise time, the fall time, the frequency, and the area under the wave. Peak time, as defined herein, refers to the time from the initiation of the waveform to the peak amplitude of the waveform. Rise time, as defined herein, refers to the time elapsed between a waveform amplitude of 10% and 90% of the peak amplitude as the amplitude is rising to the peak amplitude. Fall time, as defined herein, refers to the time elapsed between a waveform amplitude of 90% and 10% of the peak amplitude as the amplitude is falling from the peak amplitude.

Without being limited to any particular theory, there is complexity in the differing shapes of the waveforms associated with the response of the facial tissues to the force impulses. In an aspect, the signal analysis module 1106 may generate a mathematical representation of the waveform of a facial tissue response and may further manipulate and interpret the mathematical representation so as to define the amount of resistance, mobility, condition, and/or other characteristics of the facial tissue.

The signal analysis module 1106 is configured to analyze the relationship of all of the response factors associated with facial tissue treatment and measurement, namely the analysis of the waveforms as they relate to facial tissues in general. The relation to the stiffness characteristic (waveform peak), the hysteresis function (wave shape), and the frequency response provide valuable information regarding the state of the measured tissue.

In an aspect, the measured waveform may be sinusoidal and may be influenced by tissue properties including, but not limited, to tissue mobility or resistance to mobility, fascia tension, muscle tonicity, connective tissue resiliency or inertia, local edema and any combination thereof. Each such waveform may be characterized mathematically by determining the peak amplitude, peak time, rise time, fall time, and slew rate; these quantities may facilitate the calculation of frequency response and certain ratios used to mathematically define the waveform characteristics. By analyzing the mathematics of the waveform characteristics, the condition of the facial tissues may be assessed using previously determined relationships of waveform characteristics and tissue condition.

Figure 25:
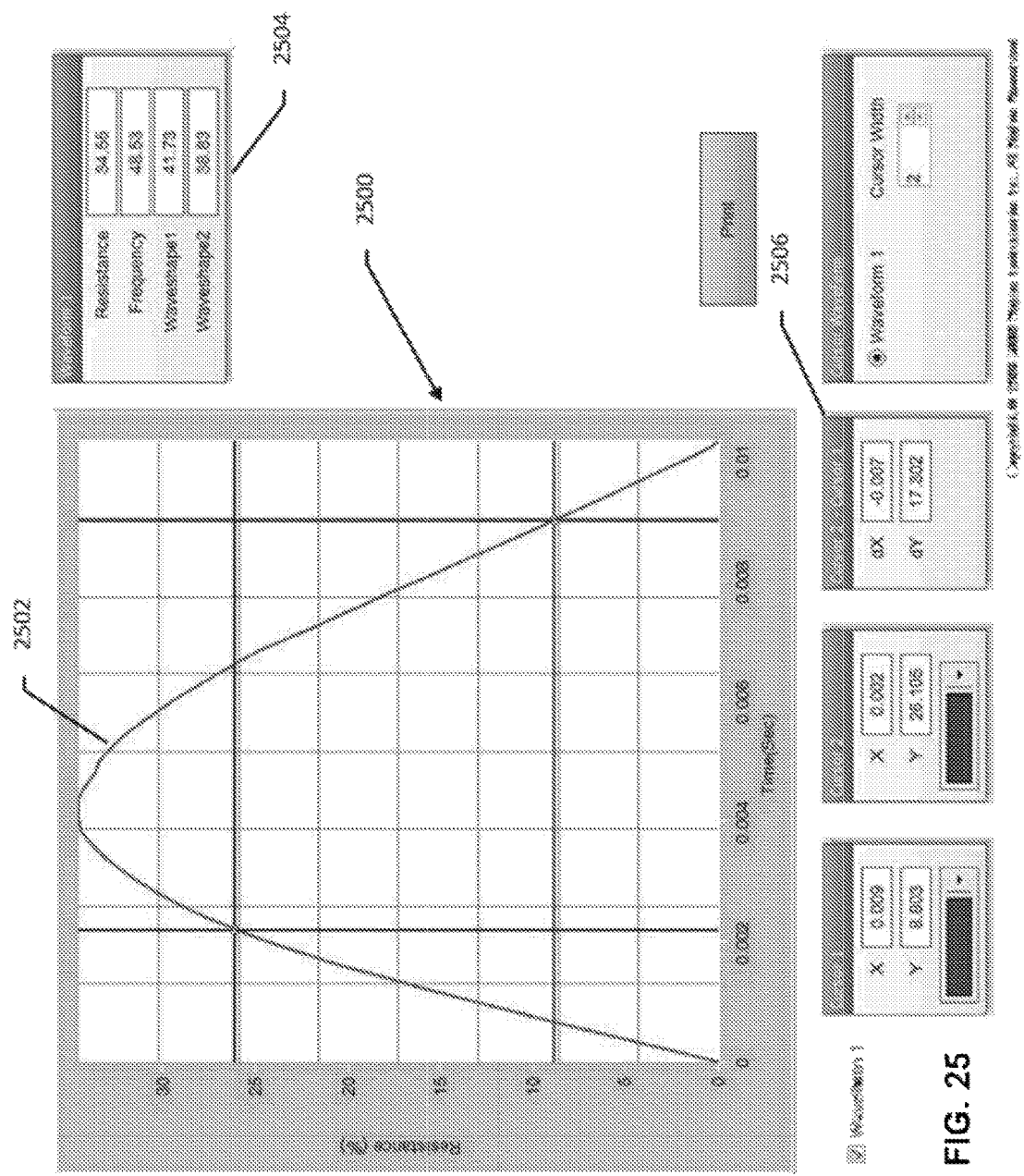
FIG. 25 shows a computer screen depicting a waveform and derived waveform data.

As the data are collected and logged and after all of the pertinent mathematic calculations are made, a summary display 2500 of the waveform and analysis may be presented on the display 112 as illustrated in FIG. 25. The summary display 2500 may include a graphic display of the waveform 2502, and the pertinent data 2504 and derived ratios 2506 may be displayed for assessment by the operator during a trigger point analysis. The data associated with the summary display 2500 may be stored in the database 122 for use by the facial treatment application 120 in determining the appropriate treatment protocol and associated instrument control settings. In addition, the stored data associated with a trigger point analysis may be incorporated into a more comprehensive database used to develop and refine predictive diagnoses using methods of analysis including, but not limited to, clinical assumptions and statistical models. Normal values associated with the waveform analysis of healthy facial tissues may be compiled, stored, and used to compare normal versus aberrant facial tissues. Stored data may also be used to compare pre-treatment and post-treatment facial tissues.

iv. Facial Asymmetry Display Module

Referring back to FIG. 5, the asymmetries of facial landmarks determined by the facial symmetry assessment module 212 may be processed for display to the operator using the facial asymmetry display module 534. The asymmetries of the facial landmarks may be expressed in any known numerical or graphical format. In one aspect, the asymmetry of each facial landmark may be expressed as a numerical degree of asymmetry, defined herein as a numerical difference between a lateral displacement or angular orientation of the left and the corresponding right facial landmark relative to a reference, such as an axis of symmetry or plane of symmetry described herein above.

The degree of asymmetry may be expressed in terms of the absolute difference between the left and right distances or angles of the corresponding facial landmarks. Alternatively, the numerical degree of asymmetry may be expressed as the difference between the left and right distances or angles of the corresponding facial landmarks as a percentage of a reference value such as the average of the left and right distances or angles or the overall maximum or minimum distance or angle. In yet another aspect, the numerical degree of asymmetry may be normalized by dividing each difference between the left and right distances or angles of the corresponding facial landmarks by a numerical constant such as the maximum or minimum difference between the corresponding left and right distances or angles amongst all facial landmarks analyzed.

In other aspects, a 2D facial image 600 and a 3D facial image 900 may be analyzed using the facial symmetry analysis module 502 and the results of the 2D and 3D symmetry analysis may be combined. For example, the degrees of asymmetry for each facial landmark resulting from the analyses of the 2D and 3D images may be averaged. Alternatively, the minimum or maximum degree of asymmetry may be selected at each facial landmark for display to the operator, or any other known method of combining data from different sources may be used.

The facial image display module 534 may generate a display of the asymmetry of the facial landmarks using any known format including, but not limited to, a list, a table, or a graph, or other image format. Non-limiting examples of suitable formats in which the asymmetry of the facial landmarks may be displayed include: a list of facial landmarks and each landmark's numerical degree of asymmetry, a table of facial landmarks including the numerical degree of asymmetry, a bar graph or other graph summarizing the numerical degree of asymmetry of each facial landmark, and a 2D facial image superimposed with markers at each facial landmark in which the degree of asymmetry of each landmark is encoded as a superimposed number, a color and/or a color intensity of the landmark's marker.

v. Instrument Control Settings Module

Referring to FIG. 5, the facial symmetry assessment module 212 may further include an instrument control settings module 508 configured to determine the control settings for the instruments to be used to administer a treatment to the facial tissues of the patient. The control settings may be determined based on the degree of asymmetry of each facial landmark, as well as any additional characteristics of the facial tissues determined by the trigger point analysis module 506. In an embodiment, the instrument control settings module 508 may determine one or more control settings for the facial stimulator instrument 106 including, but not limited to: preload tissue compression force, magnitude and frequency of a force impulse, as well as power and waveform of an electrical stimulation to be applied to the facial tissue. In another embodiment, the instrument control settings module 508 may determine one or control settings for the acoustic oscillator 108 including, but not limited to: magnitude and frequency of an acoustic pulse to be applied to the facial tissue.

vi. Treatment Selection Module

Referring to FIG. 5, the facial symmetry assessment module 212 may further include a treatment selection module 510 configured to select one or more treatment protocols based on the analysis of the degree of asymmetry of the facial tissues determined by the 2D facial asymmetry assessment module 502 and/or the 3D facial asymmetry assessment module 504, as well as other facial tissue characteristics determined by the trigger point analysis module 506. The recommended treatment protocols may be displayed to the operator as a list of treatment protocol options in an aspect. One or more treatment protocols may be selected from the displayed list by the operator in order to initiate one or more treatments to the facial tissues of the patient.

vii. Facial Image Storage Module

Referring back to FIG. 5, the facial symmetry assessment module 212 may further include a facial image storage module 512 configured to store one or more facial images and associated data in the database 122 (not shown). Non-limiting examples of facial images include 2D facial images 600 and 3D facial images 900 obtained before and/or after a treatment of a facial tissue. Non-limiting examples of data associated with the one or more facial images to be stored by the a facial image storage module 512 include: facial landmarks, degrees of asymmetry of each facial landmark, other characteristics of the facial tissues measured by the trigger point analysis module 506, instrument control settings, and a history of previous facial tissue treatments using the system 100. In one aspect, the information stored by the facial image storage module 512 may be used to compare the effects of a facial treatment on the degree of asymmetry or other characteristic of the treated facial tissue. In another aspect, the stored treatment protocol information associated with the one or more facial images may be used to specify a subsequent treatment of the facial tissues.

c. Operator-Selected Treatment Module

Referring back to FIG. 2, the treatment protocol selection module 208 includes an operator-selected treatment module 214 configured to develop and implement a treatment protocol specified by an operator via the input device 114. In an aspect, the operator-selected treatment module 214 may offer guidance to the operator in the form of menus or suggested ranges for applied voltages, stimulation frequencies, force impulse magnitudes, frequencies of impulse production, and any other parameter associated with the treatment protocol selected by the operator.

In an aspect, the operator may specify a particular treatment mode and facial landmarks to be treated. A facial image may be displayed within a GUI display in this aspect to show the selected facial landmarks to be treated. Upon selection of a particular facial landmark, the GUI may display the control settings of the instrument used to provide the treatment to the facial tissues of the patient to the operator. The operator may then specify the control settings of the instrument via the GUI. Alternatively, the GUI may guide the operator through a measurement of another characteristic of the facial tissue, and control settings of the instrument may be recommended to the operator based on the measured condition of the facial tissue. The instrument control settings are used to configure the instrument used to administer the treatment to the facial tissues of the patient.

IV. Treatment Modules

Referring back to FIG. 2, the treatment protocol selection module 208 selects a treatment protocol for a treatment of a facial tissue of a patient as discussed herein above. To implement the selected treatment protocol, the system 100A may make use of one or more treatment modules: a neural treatment module 216, a muscular treatment module 218, and a circulatory treatment module 220. In general, each of the treatment modules provides an interface with which the operator may configure the instrument to be used to treat the facial tissue of the patient according to the selected treatment protocol. In addition, each of the treatment modules may provide step-by-step guidance to the operator for placing the instrument on one or more selected facial landmarks of the patient and operating the instrument used to provide the treatment specified by the selected treatment protocol.

In an aspect, post-treatment 2D facial images 600 and/or 3D facial images 900 may be obtained following the completion of the treatment of the facial tissues to document any changes to the condition of the facial tissues resulting from the treatment. In another aspect, other measurements of the condition of the facial tissues including, but not limited to, the response of the facial tissue in reaction to applied force impulses or electrical pulses may be obtained. The post-treatment images and measurements may be stored in the database 122 in an embodiment.

Detailed descriptions of the neural treatment module 216, the muscular treatment module 218, and the circulatory treatment module 220 are provided herein below.

a. Neural Treatment Module

In an aspect, the neural treatment module 216 guides the operator through a treatment of a facial nerve tissue in accordance with a selected treatment protocol. In this aspect, the neural treatment module 216 may apply percussive impacts to facial nerves using the facial stimulator instrument 106. Other treatment protocols including, but not limited to, electrical stimulation and/or acoustic oscillations applied to facial nerve tissues may be implemented in other embodiments.

Without being limited to any particular theory, the treatment protocols implemented by the neural treatment module 216 may target Golgi tendon organs within the facial tissues of the patient. The Golgi tendon organs are encapsulated mechanoreceptors located at the myo-tendinous and myo-aponeurosis junctions. As muscle fibers shorten during a muscle contraction, the Golgi capsule containing the Golgi tendon organ becomes distorted and the contraction of the fibers forming the Golgi capsule exerts a strain on the encapsulated collagen bundle within the Golgi capsule causing a deformation of sensory terminals. The Golgi tendon organ has a very low activation threshold, and even a single muscle fiber twitch may elicit a discharge from this receptor. The discharge frequency of the Golgi tendon organ controls the proprioceptive response. Under prolonged muscle fiber contractions, such as may occur under static and prolonged muscle loading, the discharge frequency of the Golgi tendon organ diminishes, causing the proprioceptive response to be minimized or extinguished altogether. As a result of an attenuated proprioceptive response, agonist/antagonist muscle activity becomes spastic and static. In addition, a prolonged static loading condition may result in hyperactivity of the nociceptor response resulting in pain and additional muscle spasms.

Golgi tendon organs are known to fire harmonically with stimulating impulses up to 80 Hz and in a subharmonic manner (½ to ⅓) above 80 Hz. The Golgi tendon organ ($I_b$) afferents are also known to display an inverse pattern of activity relative to the firing of ($I_a$) afferents. As a result, the motor response may be inversely proportional to Golgi tendon organ firing; as the discharge frequency from Golgi tendon organs is depressed, the motor response becomes more active. Therefore the reduction in the frequency of Golgi tendon organ firing under prolonged static muscle contraction may induce a motor response hyperactivity akin to muscle hypertonia.

If a Golgi tendon organ is stimulated by applying low magnitude force oscillations within the known frequency response window of the Golgi capsule, the resulting Golgi tendon organ discharge frequency may respond harmonically to the induced oscillation frequency, inducing an appropriate proprioceptive response. In particular, the applied force oscillations may elicit a harmonic response of the Ib afferents of the Golgi tendon organ, resulting in diminished nociceptor signaling and the alleviation of pain, absent other factors such as chemical irritants, infection or inflammation within the afflicted facial tissue.

Figure 13:
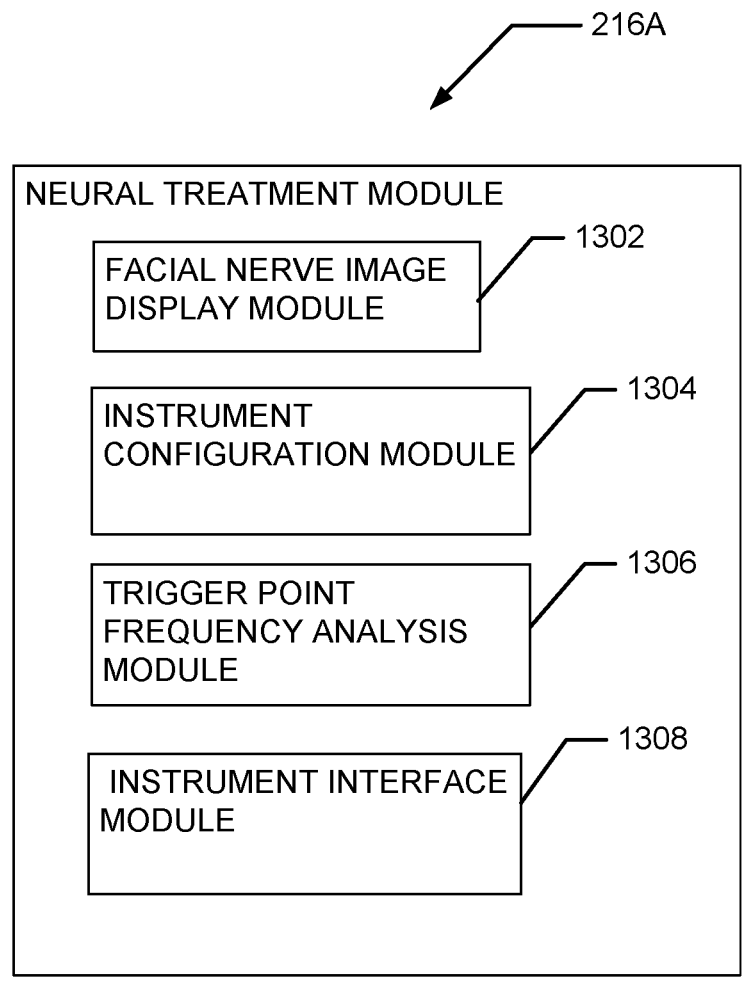
FIG. 13 is a block diagram of a neural treatment module.

FIG. 13 is a block diagram illustrating an embodiment of a neural treatment module 216A. The neural treatment module 216A may include a facial nerve image display module 1302 to produce a GUI used to guide the operator through a treatment of a facial nerve tissue. An instrument configuration module 1304 may be used to specify the control settings of the facial stimulator instrument used to implement a treatment of the facial nerve tissue including, but not limited to the magnitude and frequency of the applied percussive force, and the duration of the treatment. A trigger point frequency analysis module 1306 may guide the operator through an analysis in which the facial stimulator instrument is used to measure the response of the facial tissue through a range of frequencies of the applied percussive force and determine one or more instrument control settings based on an analysis of the measured tissue response. The instrument interface module 1308 provides a GUI or other interface used by the operator to operate the facial stimulator instrument while implementing a selected treatment protocol.

Figure 14:
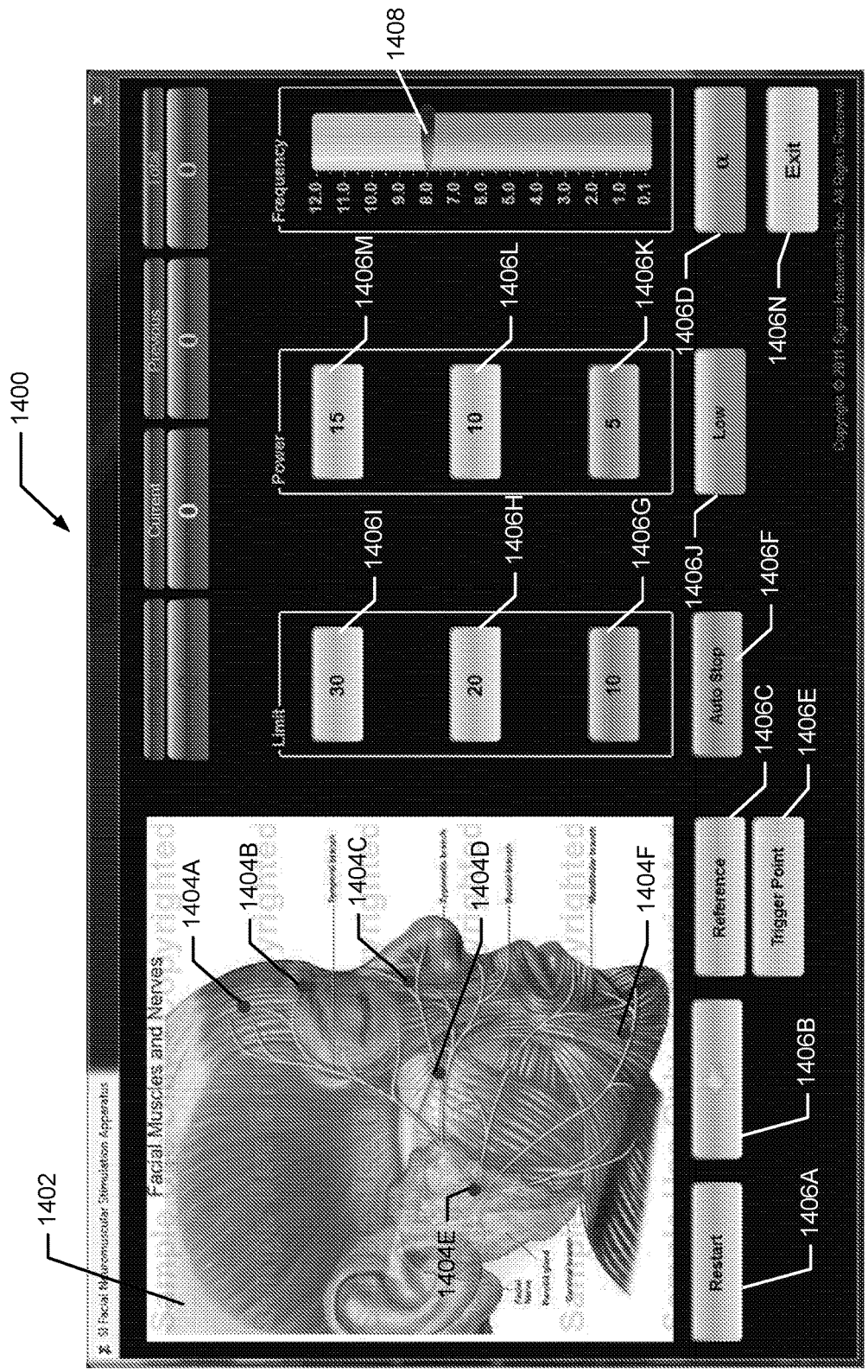
FIG. 14 is an embodiment of a neural treatment guidance display.

An example of a facial nerve display 1400 is illustrated in FIG. 14. The facial nerve display 1400 may include a nerve image 1402 illustrating the location of facial nerves to aid the operator in locating the appropriate region for treatment. In an aspect, the location of facial landmarks 1404A-1404F identified by the treatment protocol selection module 208 may be superimposed on the nerve image 1402. The frequency at which the force impulses are applied to the facial nerve tissues may be displayed and/or specified using a GUI control element such as the slider control 1408 illustrated in FIG. 14.

The facial nerve display 1400 may further include buttons 1406A-1406N used to control various other aspects of the treatment of the facial nerve tissue. The number of force impulses applied at each facial landmark may be specified by selecting one of buttons 1406F-1406I. The magnitude of the force impulses may be specified by selecting one of buttons 1406J-1406M. A trigger point analysis may be initiated by selecting button 1406E. Useful reference information may be accessed by the operator by selecting button

1406C. The operator may move between facial landmarks to be treated by selecting button 1406B, restart the treatment by selecting 1406A, or cease treatment of the facial nerve tissues by selecting button 1406N.

Figure 15:
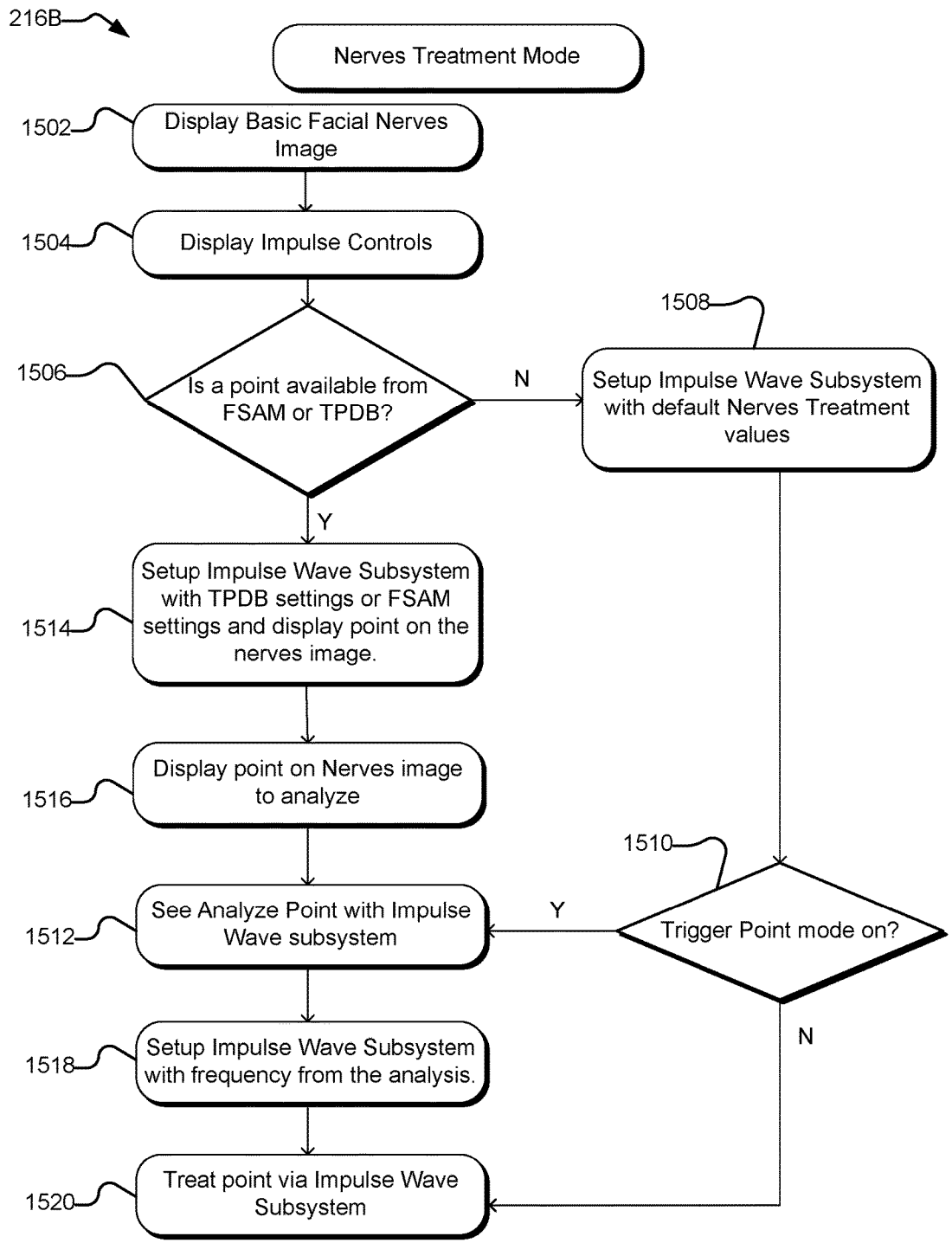
FIG. 15 is a flow chart illustrating an embodiment of a neural treatment module.

FIG. 15 is a flow chart illustrating an embodiment of the neural treatment module 216B. The nerve image 1402 and controls for the facial stimulator instrument 106 may be displayed in the facial nerve display 1400 at steps 1502 and 1504. The neural treatment module 216B determines whether instrument control settings have been specified using the stored treatment protocol module 210 or facial symmetry assessment module 212 at step 1506. If no instrument control setting has been specified, the instrument control settings are populated with default values at step 1508. Once the default values have been loaded, the neural treatment module 216B determines if a trigger point analysis is desired to refine the default settings at step 1510. If desired, a trigger point analysis is performed at the facial landmark at step 1512.

If instrument control settings were identified at step 1506, the settings are loaded into the facial nerve display 1400 at step 1514. A facial landmark to be treated is displayed on the facial nerve display 1400 at step 1516. If a trigger point analysis was conducted, the recommended instrument control settings are loaded in to the facial nerve display 1400 at step 1518, and the treatment is implemented at step 1520.

b. Muscular Treatment Module

Referring back to FIG. 2, the muscular treatment module 218 is configured to guide the operator through a treatment of one or more facial muscles associated with one or more facial landmarks in accordance with a selected treatment protocol. In this aspect, the muscular treatment module 218 may apply percussive impacts and/or electrical stimulation to facial muscles using the facial stimulator instrument 106. Other treatment protocols including, but not limited to, acoustic oscillations applied to facial muscles may be implemented in other embodiments. The acoustic (Audio) oscillations may be in the form of pulse modulated RF and/or Amplitude modulated RF in various embodiments including square or sine waves.

The treatment protocols implemented by the muscular treatment module 218 may promote the health of facial muscles by reducing fluid stasis, thereby relieving muscle inflammation resulting from an altered chemical environment of the tissues and improving tissue metabolism in an aspect. In other aspects, the muscular treatment module 218 may implement a tendon vibration treatment that may stimulate mechanoreceptors, inducing the relaxation of muscles.

The relaxation of facial muscles induced by the treatment protocols implemented by the muscular treatment module 218 may reduce the appearance of facial wrinkles associated with the prolonged contraction of one or more facial muscles. Non-limiting examples of types of facial wrinkles that may be reduced in appearance after treatments of the facial muscles include: horizontal forehead lines associated with contraction of the frontalis muscle; glabellar frown lines associated with the contraction of corrugator and procerus muscles; crow's feet associated with movement of the orbicularis oculi; perioral lines associated with the contraction of the orbicularis oris sphincter of the mouth; marionette folds associated with contraction of the depressor anguli oris muscle; platysma bands associated with contraction of the platysma muscles; and any combination thereof.

Figure 16:
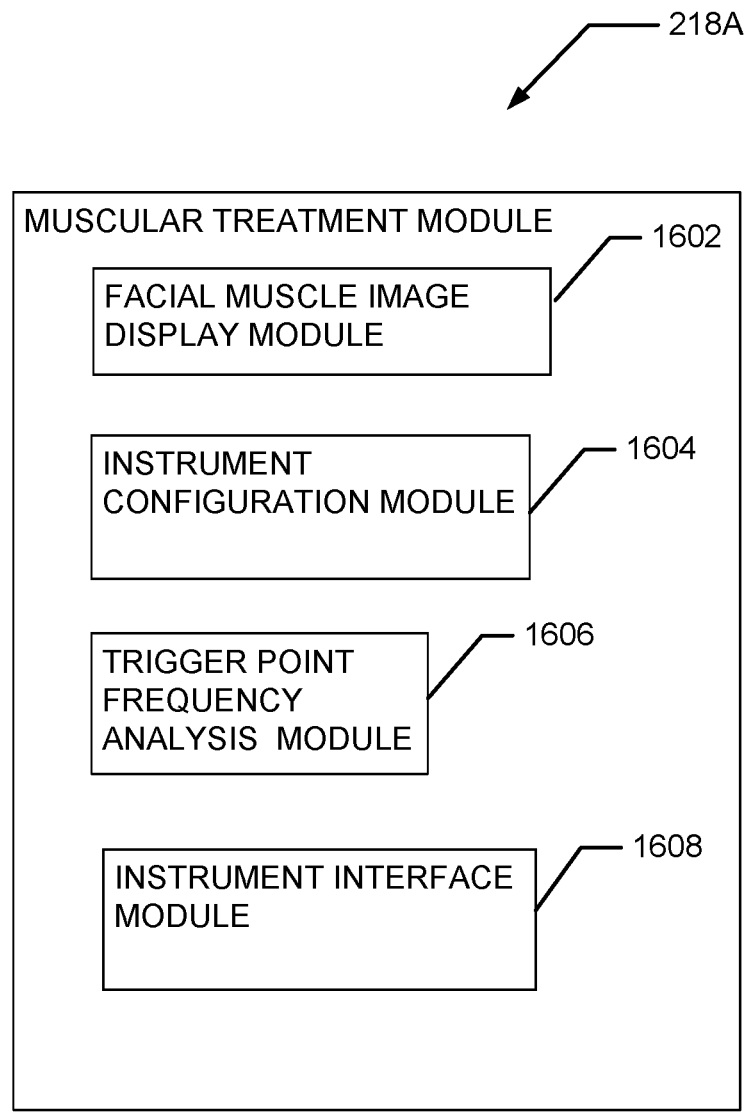
FIG. 16 is a block diagram of a muscular treatment module.

FIG. 16 is a block diagram illustrating an embodiment of a muscular treatment module 218A. The muscular treatment module 218A may include a facial muscle image display module 1602 to produce a GUI used to guide the operator through a treatment of a facial nerve tissue. An instrument configuration module 1604 may be used to specify the control settings of the facial stimulator instrument 106 used to implement a treatment of the facial muscle tissue including, but not limited to the magnitude and frequency of the applied force impulse, and the duration of the treatment. A trigger point frequency analysis module 1606 may guide the operator through an analysis in which the facial stimulator instrument is used to measure the response of the facial tissue through a range of frequencies of the applied force impulse and to determine one or more instrument control settings based on an analysis of the measured tissue response. The instrument interface module 1608 provides a GUI or other interface used by the operator to operate the facial stimulator instrument while implementing a selected treatment protocol.

Figure 17:
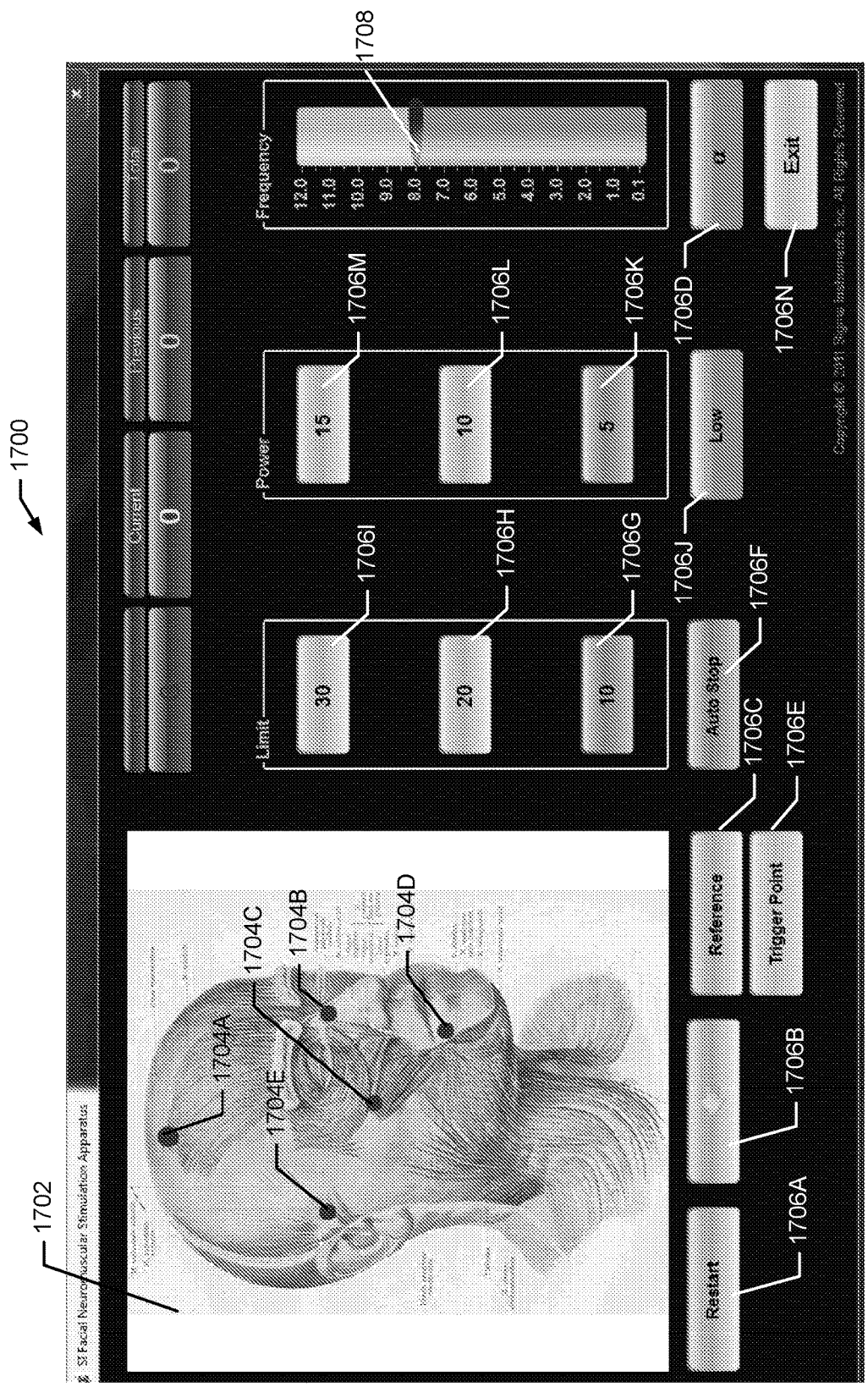
FIG. 17 is an embodiment of a muscular treatment guidance display.

An example of a facial muscle display 1700 is illustrated in FIG. 17. The facial muscle display 1700 may include a muscle image 1702 illustrating the location of facial muscle to aid the operator in locating the appropriate region for treatment. In an aspect, the location of facial landmarks 1704A-1704E identified by the treatment protocol selection module 208 may be superimposed on the muscle image 1702. The frequency at which the force impulses are applied to the facial muscle tissues may be displayed and/or specified using a GUI control element such as the slider control 1708 illustrated in FIG. 17.

The facial muscle display 1700 may further include buttons 1706A-1706N used to control various other aspects of the treatment of the facial muscle tissue. The number of force impulses applied at each facial landmark may be specified by selecting one of buttons 1706F-1706I. The magnitude of the force impulses may be specified by selecting one of buttons 1706J-1706M. A trigger point analysis may be initiated by selecting button 1706E. Useful reference information may be accessed by the operator by selecting button 1706C. The operator may move between facial landmarks to be treated by selecting button 1706B, restart the treatment by selecting 1706A, or cease treatment of the facial muscle tissues by selecting button 1706N.

Figure 18:
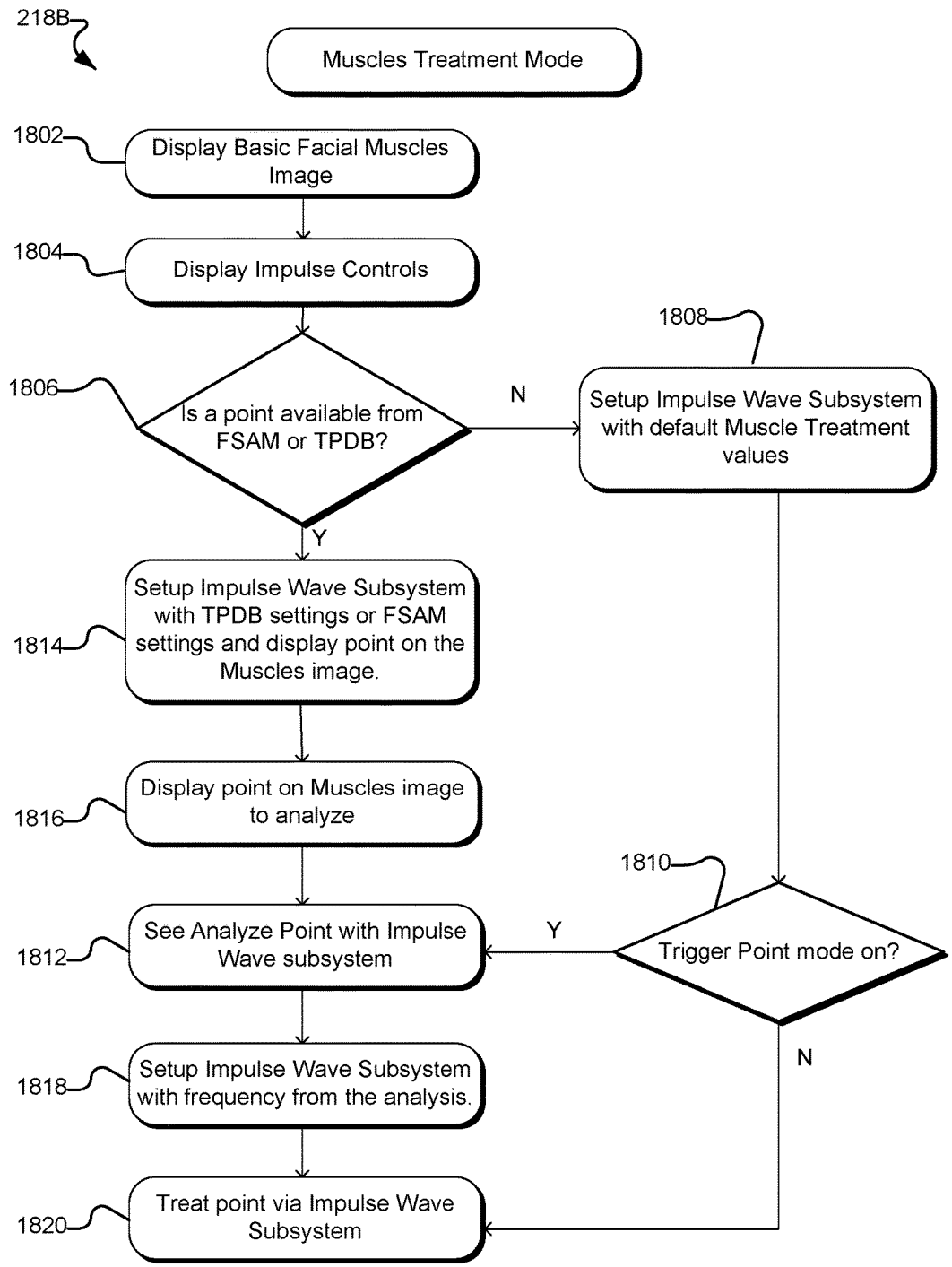
FIG. 18 is a flow chart illustrating an embodiment of a muscular treatment module.

FIG. 18 is a flow chart illustrating an embodiment of the muscular treatment module 218B. The muscle image 1702 and controls for the facial stimulator instrument 106 may be displayed in the facial muscle display 1700 at steps 1802 and 1804. The muscular treatment module 216B determines whether instrument control settings have been specified using the stored treatment protocol module 210 or facial symmetry assessment module 212 at step 1806. If no instrument control setting has been specified, the instrument control settings are populated with default values at step 1808. Once the default values have been loaded, the muscular treatment module 218B determines if a trigger point analysis is desired to refine the default settings at step 1810. If desired, a trigger point analysis is performed at the facial landmark at step 1812.

If instrument control settings were identified at step 1806, the settings are loaded into the facial muscle display 1700 at step 1814. A facial landmark to be treated is displayed on the facial muscle display 1700 at step 1816. If a trigger point analysis was conducted, the recommended instrument control settings are loaded into the facial muscle display 1700 at step 1818, and the treatment is implemented at step 1820.

c. Circulatory Treatment Module

Referring back to FIG. 2, the circulatory treatment module 220 is configured to guide the operator through a treatment of one or more facial circulatory vessels associated with one or more facial landmarks in accordance with a selected treatment protocol. In this aspect, the circulatory treatment module 220 may apply acoustic pulses to facial circulatory vessels using the acoustic oscillator 108. Other treatment protocols including, but not limited to, force impulses and/or electrical stimulation applied to facial circulatory vessels may be implemented in other embodiments.

The treatment protocols implemented by the circulatory treatment module 220 may stimulate enhanced blood flow to the facial tissues, thereby enhancing the health and appearance of facial tissues.

Figure 19:
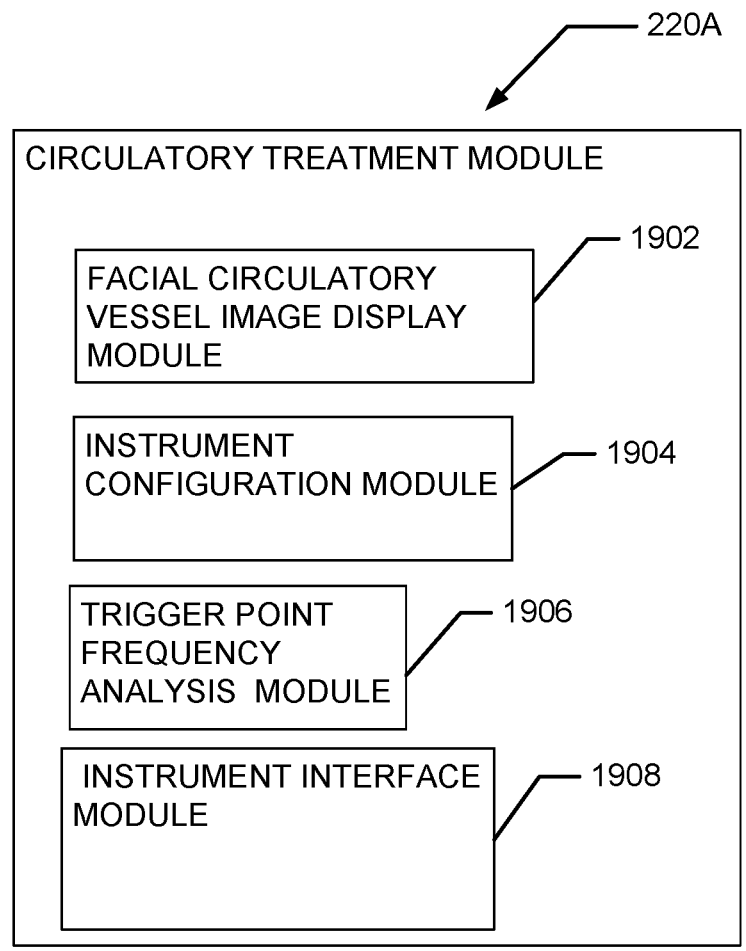
FIG. 19 is a block diagram of a circulatory treatment module.

FIG. 19 is a block diagram illustrating an embodiment of a circulatory treatment module 220A. The circulatory treatment module 220 may include a facial circulatory vessel image display module 1902 to produce a GUI used to guide the operator through a treatment of a facial circulatory vessel. An instrument configuration module 1904 may be used to specify the control settings of the acoustic oscillator used to implement a treatment of the facial circulatory vessel tissue including, but not limited to the magnitude and frequency of the applied acoustic pulses, and the duration of the treatment. The instrument interface module 1908 provides a GUI or other interface used by the operator to operate the acoustic oscillator while implementing a selected treatment protocol.

A trigger point frequency analysis module 1906 may guide the operator through an analysis in which the facial stimulator instrument 106 is used to measure the response of the facial tissue through a range of frequencies of applied percussive force at the various facial landmarks selected for treatment and to determine one or more instrument control settings based on an analysis of the measured tissue response. For example, the trigger point frequency analysis module 1906 may determine a resonant frequency for each of the facial landmarks using the tissue response measured by the facial stimulator instrument 106. These resonant frequencies may be used as a basis for a treatment frequency protocol at each of the facial landmarks that specifies the frequency of acoustic pulses to be applied at each facial landmark.

In an aspect, the treatment frequency protocol may be a sweep concentration frequency protocol, in which the acoustic pulses are provided in the form of a programmable duty cycle transmission wave. In this aspect, the acoustic pulses may have an oscillation frequency ranging between about 800 KHz and about 1 MHz delivered at a pulse rate ranging between about 3 Hz and about 300 Hz. In this aspect, the pulse rate may be concentrated within the harmonics and sub-harmonics of the resonant frequency determined by the trigger point frequency analysis module 1906. This pulse can be delivered as a burst or in an amplitude modulated form.

In another aspect, the treatment frequency protocol may be a harmonic sweep concentration protocol similar to the sweep concentration frequency protocol, except that the pulse rate may be initially set at the exact resonant frequency determined by the trigger point frequency analysis module 1906 and subsequently swept up and down the harmonic range.

In an additional aspect, the treatment frequency protocol may be a resonance concentration similar to the sweep concentration frequency protocol and harmonic sweep protocol, except that the pulse rate is initialized and maintained at the specific resonant frequency determined by the trigger point frequency analysis module 1906.

Figure 20:
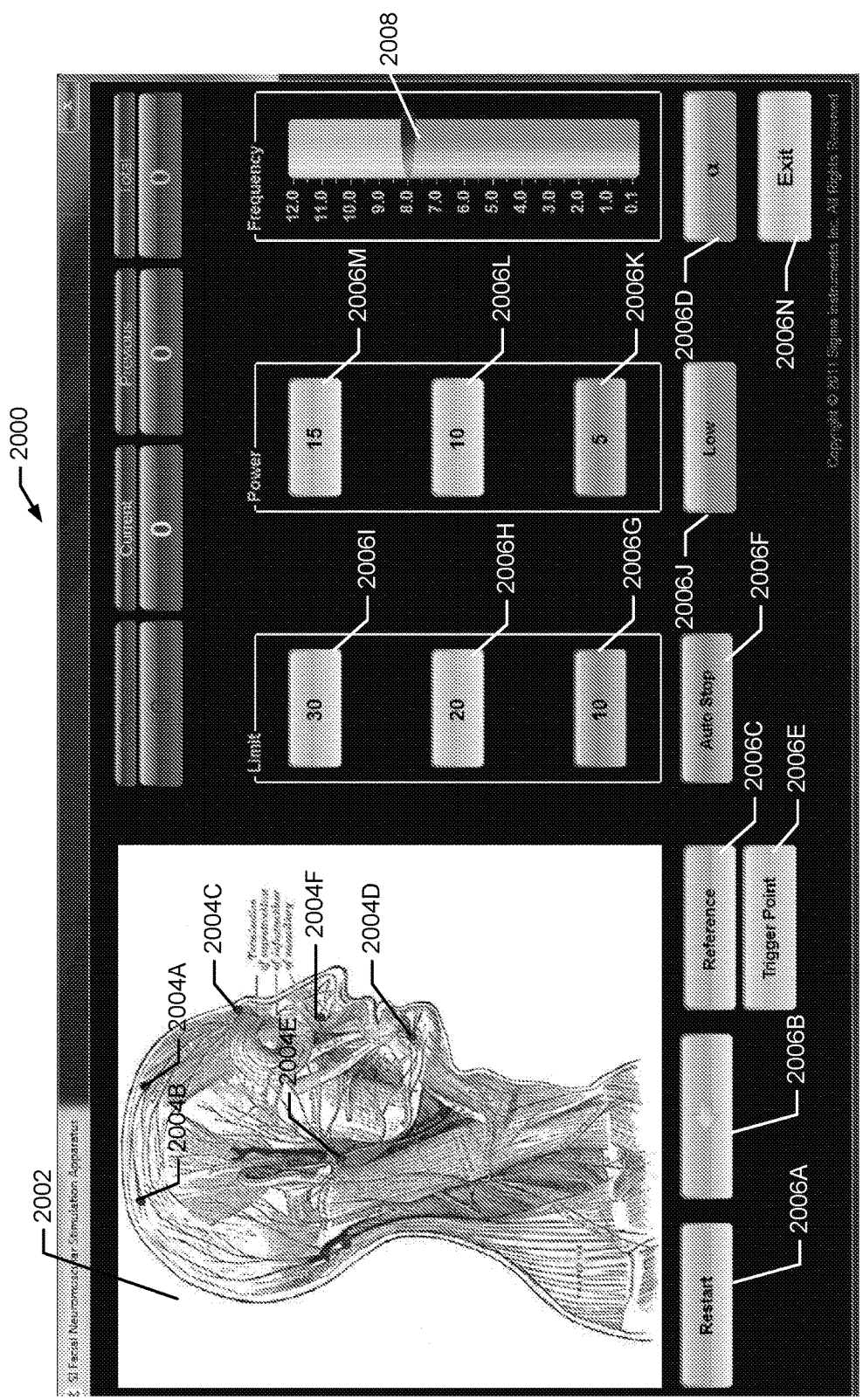
FIG. 20 is an embodiment of a circulatory treatment guidance display.

An example of a circulatory vessel display 2000 is illustrated in FIG. 20. The circulatory vessel display 2000 may include a circulatory vessel image 2002 illustrating the location of a circulatory vessel muscle to aid the operator in locating the appropriate region for treatment. In an aspect, the location of facial landmarks 2004A-2004G identified by the treatment protocol selection module 208 may be superimposed on the circulatory vessel image 2002. The frequency at which the acoustic pulses are applied to the facial circulatory tissues may be displayed and/or specified using a GUI control element such as the slider control 2008 illustrated in FIG. 20.

The facial circulatory vessel display 2000 may further include buttons 2006A-2006N used to control various other aspects of the treatment of the facial circulatory tissue. The duration of the acoustic pulses applied at each facial landmark may be specified by selecting one of buttons 2006F-2006I. The magnitude of the acoustic pulses may be specified by selecting one of buttons 2006J-2006M. A trigger point analysis may be initiated by selecting button 2006E. Useful reference information may be accessed by the operator by selecting button 2006C. The operator may move between facial landmarks to be treated by selecting button 2006B, restart the treatment by selecting 2006A, or cease treatment of the facial circulatory vessels by selecting button 2006N.

Figure 21:
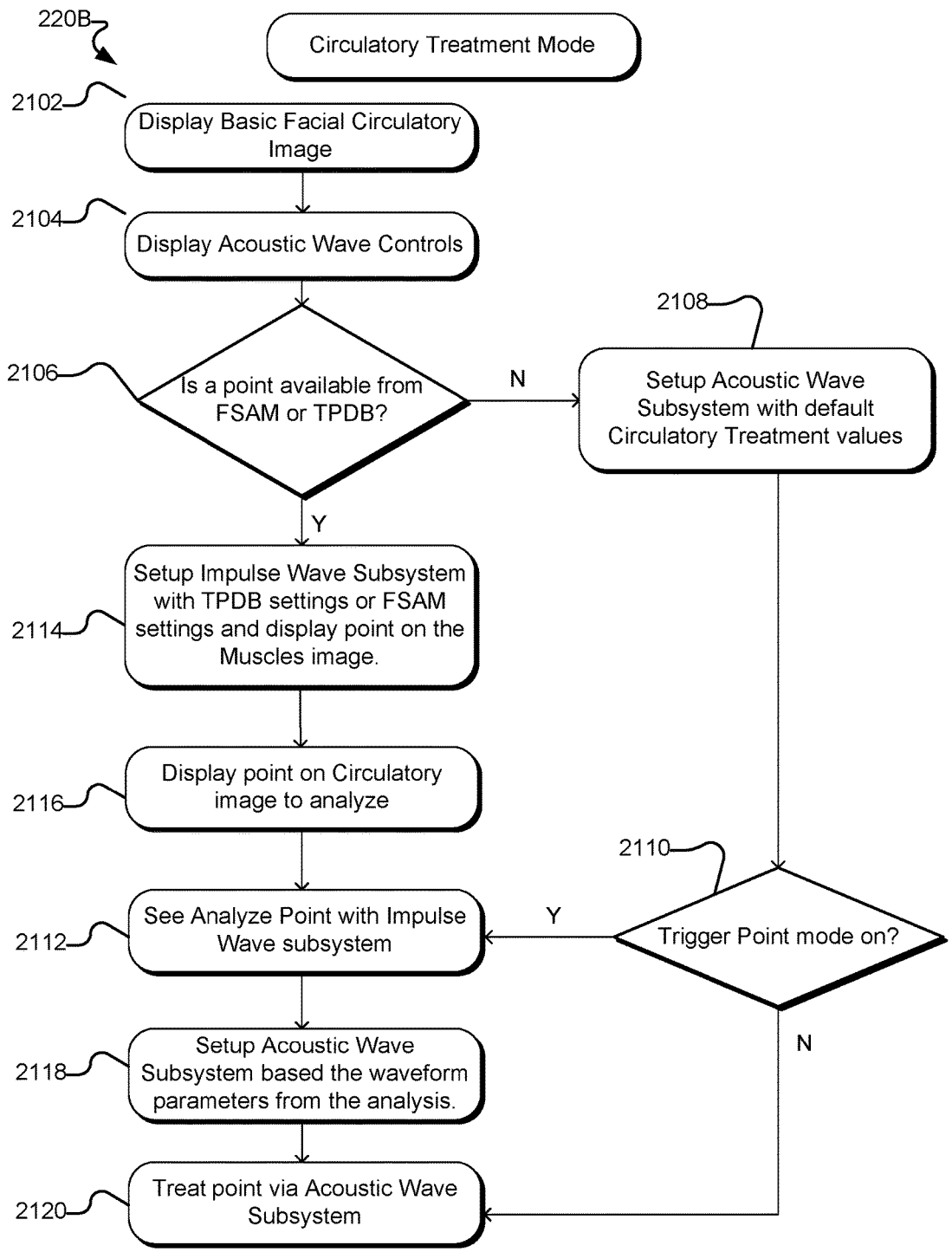
FIG. 21 is a flow chart illustrating an embodiment of a circulatory treatment module.

FIG. 21 is a flow chart illustrating an embodiment of the circulatory treatment module 220B. The circulatory vessel image 2002 and controls for the acoustic oscillator 108 may be displayed in the circulatory vessel display 2000 at steps 2102 and 2104. The circulatory treatment module 220B determines whether instrument control settings have been specified using the stored treatment protocol module 210 or facial symmetry assessment module 212 at step 2106. If no instrument control settings have been specified, the instrument control settings are populated with default values at step 2108. Once the default instrument controls settings have been loaded, the circulatory treatment module 220B determines if a trigger point analysis is desired to refine the default settings at step 2110. If desired, a trigger point analysis is performed at the facial landmark at step 2112.

If any instrument control settings were identified at step 2106, the settings are loaded into the circulatory vessel display 2000 at step 2114. A facial landmark to be treated is displayed on the facial circulatory vessel display 2000 at step 2116. If a trigger point analysis was conducted, the recommended instrument control settings are loaded into the facial circulatory vessel display 2000 at step 2118, and the treatment is implemented at step 2120.

V. Database

Referring back to FIG. 1, a database 122 may store a variety of data for use by the facial treatment system 100 to provide a treatment to the facial tissues of a patient. In an aspect, the database 122 may include the entries associated with stored treatment protocols 124, stored patient data 126, and measurement-correlated instrument control settings 132. In an aspect, the stored patient data 126 may include stored facial images 128 and patient-specific treatment protocols 130. The entries stored in the database 122 may be accessed by the modules of the facial treatment application 120 to aid in the analysis of the condition of a patient's facial tissues, the selection of a treatment protocol, and the specification of one or more instrument control settings associated with a selected treatment protocol and/or a measured characteristic of a facial tissue, and the implementation of the facial tissue treatment by the system 100.

a. Stored Treatment Protocols

Figure 23:
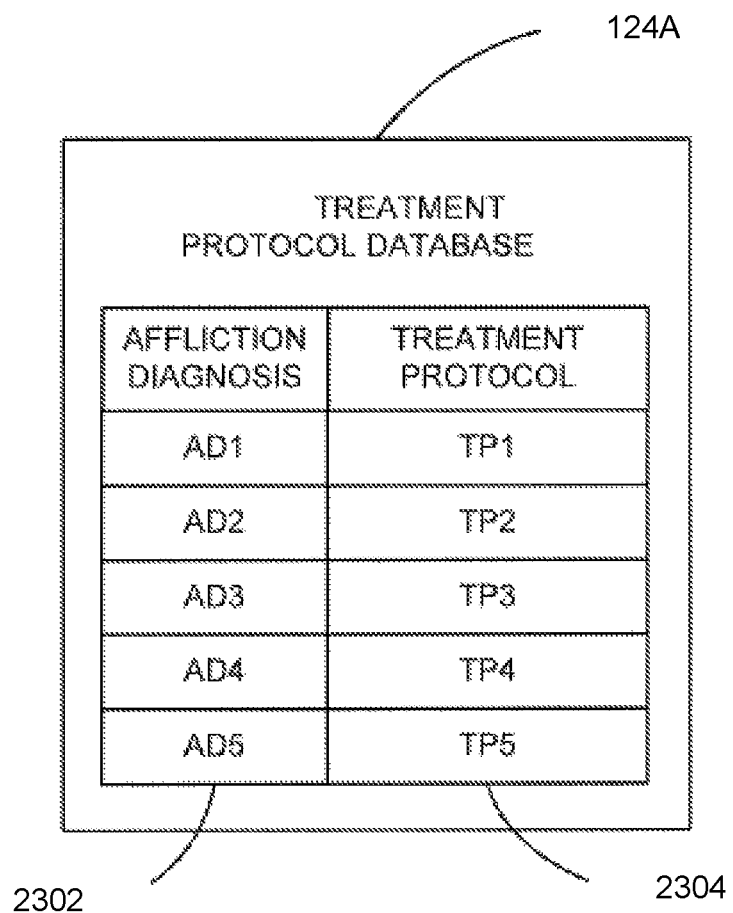
FIG. 23 is a diagrammatic depiction of a database for selecting a treatment protocol based on a diagnosis of a facial tissue disorder.

In an aspect, the stored treatment protocols 124 may provide the instrument control settings, facial landmarks, and/or any other information specifying a treatment protocol. FIG. 23 is a diagrammatic depiction of an embodiment of a stored treatment protocol 124A. In this aspect, the stored treatment protocol database 124A includes a list of affliction diagnosis entries 2302 and associated treatment protocols 2304. The affliction diagnosis entries 2302 may be any of the afflictions of the facial tissues described previously herein above. Non-limiting examples of affliction diagnosis entries 2302 include changes in appearance related to aging and erosion of subdermal fat, thinning of the skin, loss of elasticity and tone of skin, formation of wrinkles or jowls, changes or irregularities in skin coloration, and any of the disorders of the facial tissues including facial muscle spasms, decreased movement control, chronic migraines, facial neuralgia, facial paralysis, facial nerve injuries, and facial tissue abnormalities associated with systemic disorders such as muscular dystrophy.

b. Stored Patient Data

In another aspect, the database 122 may further include stored patient data 126 including, but limited to, information about the patient such as age, height, weight, and medical history, results of analyses of the patient's facial tissues, treatments performed on the patient's facial tissues, notes and comments by the operator, and a schedule of future treatments to be performed. The information contained within the stored patient data 126 provides information for use by the operator of the system 100 to select a treatment, assess the efficacy of an administered treatment, and/or select a future treatment protocol. The history of patient analysis and treatment may be compiled and used for discussion of patient's condition and progress as well as justification for continuing treatment and rehabilitation.

i. Stored Facial Images

In an additional aspect, facial images of the patient obtained before, during, and/or after a treatment may be stored in the stored facial images 128. The facial images may be 2D facial images and/or 3D facial images described herein above. The facial images may be stored for one or more treatments and may be used to assess the efficacy of the treatments over an extended time period. In another aspect, additional information such as facial landmarks, analysis results, calculated asymmetry data, and previously suggested treatments may be associated with the facial images and stored in the stored facial images 128.

ii. Patient-Specific Treatment Protocols

In another additional aspect, a set of treatment protocols customized for a particular patient may be stored in the stored patient data 126 as patient-specific treatment protocols 130. The entries within the patient-specific treatment protocols may include information including, but not limited to facial landmarks to be treated, the type of treatment to be applied, the instrument control settings associated with the treatment protocol, and any other information useful to defining a particular treatment protocol and implementing the treatment. In an aspect, the patient-specific treatment protocols 130 may be accessed by the operator and used to implement the treatment of a patient's facial tissues without need for a facial tissue symmetry assessment or other measurements of the condition of the patient's facial tissues. In another aspect, the patient-specific treatment protocols 130 may include the treatment protocols of treatments to be administered according to a schedule developed by the operator.

iii. Stored Instrument Control Settings

In another additional aspect, one or more tables containing entries used to determine one or more instrument control settings based on one or more measurements of the condition of a facial tissue may be stored in the measurement-correlated instrument control settings 132. These entries may be accessed by modules of the facial treatment application related to trigger point analysis, dynamic adjustment of control settings, implementation of treatment protocols, and the like. Any instrument control setting of any instrument described herein may be stored as a function of any measurement of the facial tissue in the measurement-correlated instrument control settings 132.

Figure 27:
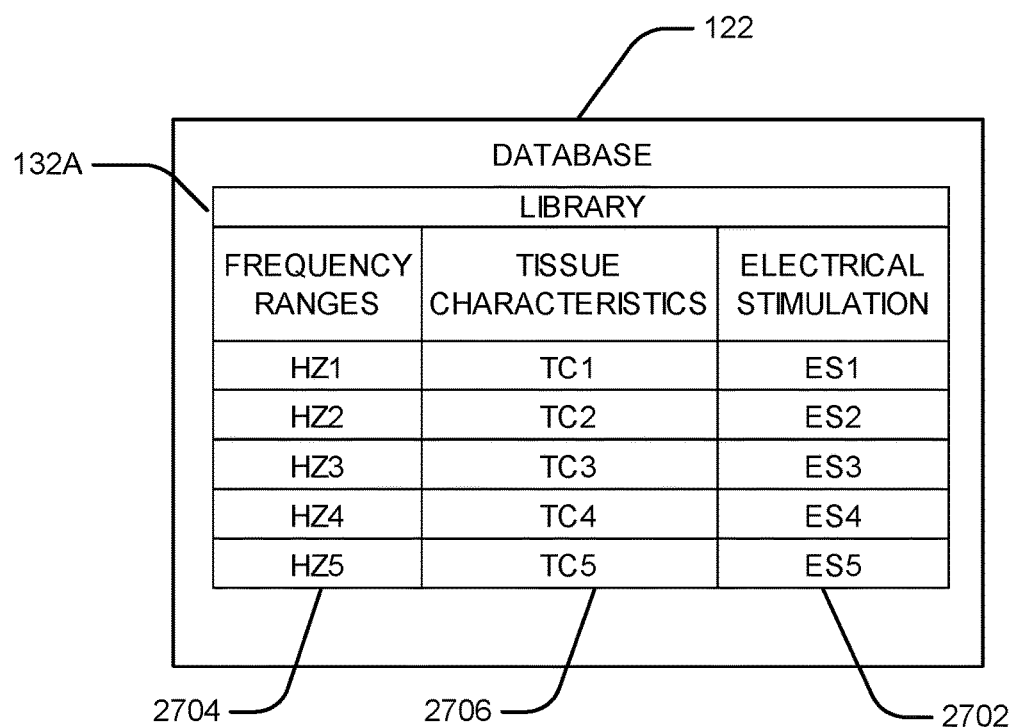
FIG. 27 is a diagrammatic depiction of a database containing stored instrument control settings associated with the implementation of an electrical stimulation as a function of the frequency response of a facial tissue to an applied force impulse.

An example of a table 132A is illustrated in FIG. 27. In this table 132A, the instrument control settings 2702 associated with an electrical stimulation are stored as a function of the measured frequency response 2704 of a facial tissue in response to a force impulse applied by the facial stimulator instrument 106. In addition, the instrument control settings 2702 may be stored as a function of another measured facial tissue characteristic 2706.

Figure 28:
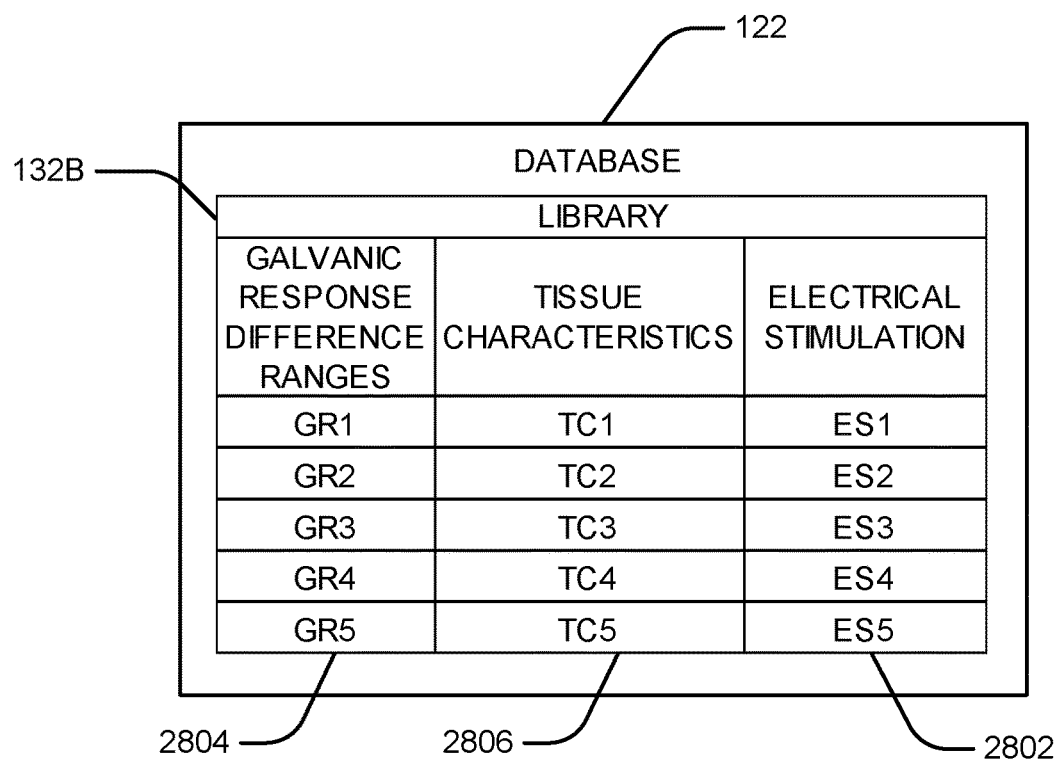
FIG. 28 is a diagrammatic depiction of a database containing stored instrument control settings associated with the implementation of an electrical stimulation as a function of the measured change in galvanic response in reaction to an applied electrical stimulus.

Another example of a table 132B is illustrated in FIG. 28. In this table 132B, the instrument control settings 2802 associated with an electrical stimulation are stored as a function of the measured change in galvanic response 2804 of a facial tissue in response to an electrical pulse applied by the facial stimulator instrument 106. In addition, the instrument control settings 2802 may be stored as a function of another measured facial tissue characteristic 2806.

VI. Cameras

Referring back to FIG. 1, the facial treatment system 100 may include one or more cameras to obtain facial images of the patient to be analyzed for symmetry of facial landmarks. These images may be taken before, during, and/or following a treatment of the facial tissues of a patient using the facial treatment system 100. The analysis of the facial images may be used to determine a recommended treatment protocol, to assess the effect of a treatment of the facial tissues by comparing a pre-treatment analysis to a post-treatment analysis, and/or to monitor the condition of the facial tissues by comparing two or more analyses over a period of time.

Any device capable of obtaining a digital image that is compatible with the computing device 102, and in particular with the facial treatment application 120 may be included in the system 100. In an aspect, the one or more cameras 104 are capable of being operated remotely using modules of the facial treatment application 120. Any known device capable of recording a facial image in digital format may be included in the system 100 including, but not limited to 2D cameras, 3D stereoscopic cameras, and 3D scanning devices. Non-limiting examples of 3D scanning devices include time-of-flight 3D laser scanners, triangulation 3D laser scanners, LIDAR scanners, structured-light 3D scanners, modulated light 3D scanners, CT scanners, MRI scanners and any other known 3D scanning device. In another aspect, other devices may be used to obtain additional types of facial images including, but not limited to, infrared imaging devices and ultrasound scanners.

VII. Facial Stimulator Instrument

Referring again to FIG. 1, the facial tissue treatments of a patient may be implemented using one or more instruments, including a facial stimulator instrument 106. The facial stimulator instrument 106 may be configured to deliver a mechanical force impulse and/or an electrical stimulation to the facial tissues. In addition, the facial stimulator instrument 106 may be configured for the measurement of facial tissue response arising from the application of a force impulse and/or electrical pulse to the facial tissue of a patient.

Figure 22:
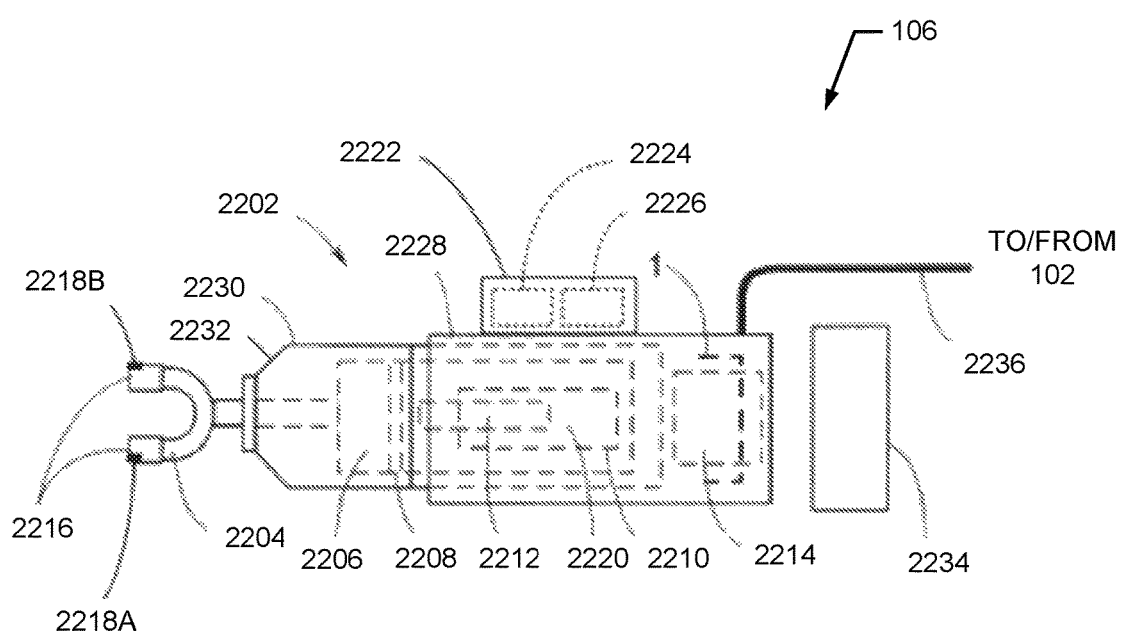
FIG. 22 is a cross-sectional side view of a facial stimulator instrument.

FIG. 22 is a side view of the facial stimulator instrument 106 in one aspect. The facial stimulator instrument 106 includes an impulse and sensing head 2202 that contacts the facial tissues of the patient to deliver the mechanical force impulses and/or electrical pulses. The impulse and sensing head 2202 includes a probe 2204 with one or more tips 2216 that contact the facial tissues of the patient. A piezoelectric sensor 2206 is firmly attached to the probe 2204, and an anvil 2208 is firmly attached to the piezoelectric sensor 2206. A solenoid assembly 2220 containing an armature 2212 inserted without attachment into an electromagnetic coil 2210 is also included in the impulse and sensing head 2202. A pressure sensor 2214 may be attached to the head 2202 and configured so that when the probe 2204 is pressed against the patient's facial tissue and reaches a predetermined pressure, the pressure sensor 2214 causes a release of a burst of current to energize the electromagnetic coil 2210. When the electromagnetic coil 2210 is energized, the armature 2212 is accelerated to impact the anvil 2208 and thereby produce a force impulse, which travels through the piezoelectric sensor 2206 and probe 2204, thereby transmitting the force impulse to the facial tissues of the patient in contact with the probe 2204.

Figure 24:
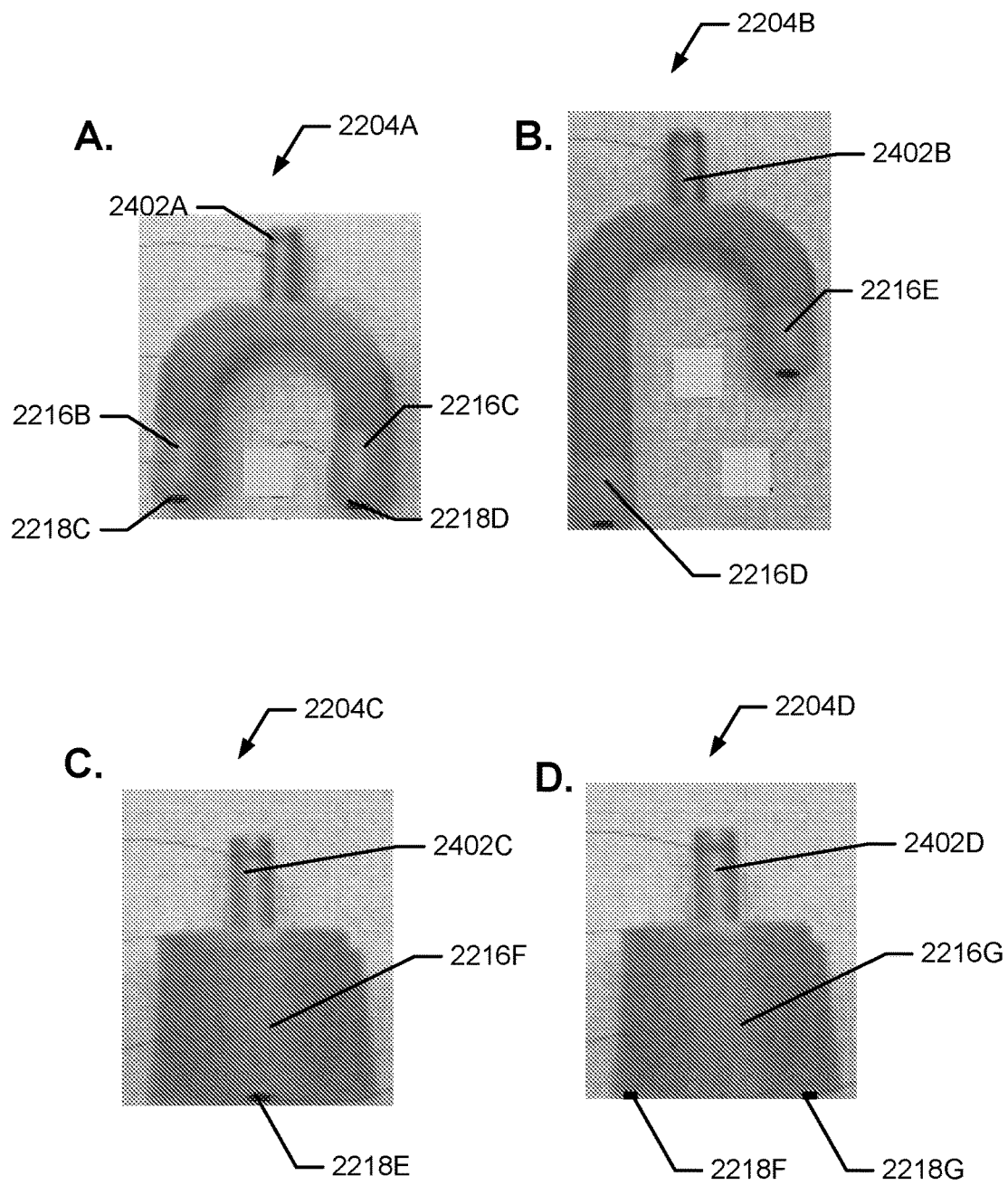
FIGS. 24A-24D are diagrams of embodiments of probes for a facial stimulator instrument.

As illustrated in FIGS. 24A-24D, a variety of different configurations of probes 2204 may be employed with the impulse and sensing head 2202. For example, as illustrated in FIG. 24A, the dual-tipped probe 2204A may have a generally horseshoe shape ending in two laterally separated tips 2216B and 2216C; the tips 2216B and 2216C may be constructed of a soft material. The tips 2216B and 2216C may attach to a stem 2402A. The end of the stem 2402A opposite to the tips 2216B and 2216C may be coupled to the piezoelectric sensor 2206 (not shown) during use. Each of the tips 2216B and 2216C may end in attached electrodes 2218C and 2218D. The tips 2216B and 2216C of the dual-tipped probe 2204A may extend generally an even distance from the body 2402A. As shown in FIG. 24B, an alternative embodiment of a dual-tipped probe 2204B may have tips 2216D and 2216E that do not extend an even distance away from the body 2402B.

In another embodiment, illustrated in FIG. 24C, a single-tipped probe 2204C may include a single tip 2216F extending from the body 2402C and ending in a single electrode 2218E. In this embodiment, a second electrode patch or other conductor may be attached to the skin of the patient in the vicinity of the facial landmark to which the single-tipped probe 2204C is pressed in order to administer an electrical stimulation. In an additional embodiment, a single-tipped probe 2204D may include a single tip 2216G to which a pair of electrodes 2218F and 2218G are attached opposite to the attachment of the tip 2216G to the body 2402D. In this embodiment, electrical stimulation may be administered by the single-tipped probe 2204D without need for additional electrode patches or other conductors.

In general, the specific shapes and dimensions of the probe 2204 may vary amongst the embodiments. In an aspect, the tips 2216B and 2216C of the dual-tipped probe 2204A may extend away from the body 2402A to a greater or lesser extent than shown in FIG. 24A, or may be laterally separated a greater or lesser distance than that shown on FIG. 24A. In another aspect, the difference in tip lengths 2216D and 2216E may be greater or lesser than that shown in FIG. 24B. In an additional aspect, the length, width, and cross-sectional shape of the tip 2216F of the single-tipped probe 2204C, as well as the location of the electrode 2218 may vary from the embodiment illustrated in FIG. 24C. In yet other aspects, the shape of the ends of the tips 2218 may generally vary amongst at least several shapes including a flat ended tip as illustrated in FIGS. 24C and 24D, a rounded or hemispherical tip as illustrated in FIGS. 24A and 24B, and any other known tip shape.

Referring back to FIG. 22, the impulse and sensing head 2202 may further include an elongated and generally cylindrical housing 2228 which has an insert 2230 that tapers to form a generally conical configuration at the forward end 2232. The other end of the housing 2228 is provided with a cylindrical closed end 2234. The housing 2228 and the closed end 2234 may be separately connected by a screw threaded connection to provide access into the interior of the housing 2228 and to separate the components of the facial stimulator instrument 106 for repair, replacement and the like. After the housing 2228 is unscrewed from closed end 2234, it may slide back and insert 2230 may also be unscrewed from the housing 2228.

The probe 2204 may further include one or more electrodes 2218A and 2218B attached to the one or more tips 2216 such that the electrodes 2218A and 2218B contact the skin of the patient in order to deliver an electrical stimulation to the facial tissues. An electrical stimulation unit 2222 may employ a high frequency oscillator 2224 and a power amplifier 2226 to generate a series of high frequency electrical pulses that are then delivered to the facial tissues of the patient via the electrodes 2218A and 2218B contacting the patient's skin.

The design of the facial stimulator instrument 106 also provides the ability to monitor the force impulses and electrical stimulation as they are applied to the facial tissues. The piezoelectric sensor 2206 may monitor the force impulses as they are applied to assess the response of the facial tissue of the patient to the application of the force impulses; the signals produced by the piezoelectric sensor 2206 may be output to the computing device 102 for processing by the facial treatment application 120. The pressure sensor 2214 may output data characteristic of the pressure of the probe 2204 in contact with the facial tissue of the patient to the computing device 102 for processing by the facial treatment application 120.

The facial stimulator instrument 106 may obtain power from the computing device 102 via an electrical cable 2236. Alternatively, electrical power may be supplied through an additional electrical cord (not shown) that may be electrically connected to an external power supply, suitable electrical outlet, or the like, which extends into the housing 2228.

In an aspect, the facial stimulator instrument 106 receives signals from the computing device 102 that control the production and delivery of force impulses and/or electrical stimulation in accordance with a treatment protocol selected and specified using the modules of the facial treatment application 120 as described herein previously. A more detailed description of the design of the facial stimulator instrument 106 in relation to the delivery of force impulses and electrical stimulation is provided herein below.

a. Force Impulse Production

In an aspect, the facial stimulator instrument 106 is configured to develop and deliver a series of force impulses to the facial tissues of a patient, resulting in a percussive massage therapy. The probe 2204 of the facial stimulator instrument 106 may oscillate by repetitively accelerating the armature 2212 to impact the anvil 2208 at a controlled frequency and a predetermined time period. Control signals received from the computing device 102 by the facial stimulator instrument 106 via an electrical cable 2236 or other signal communication method control one or more characteristics of the force impulses. Non-limiting examples of characteristics of the force impulses include the frequency of production of the force impulses, the peak force of each force impulses, the duration of the series of force impulses.

In another aspect, the frequency of production of the force impulses may range between about 0.1 Hz and approximately 12 Hz. In an additional aspect, the frequency of production of the force impulses may be varied according to a predefined schedule received from the facial treatment application 120. For example, the frequency of production of the force impulses may gradually increase from about 4 Hz to about 12 Hz in increments of about 0.1 Hz. In yet another aspect, the frequency of production of the force impulses may be continuously varied based on the analysis of measurements of facial tissue response to the force impulses performed by the facial treatment application.

In another aspect, the force impulses may be delivered by the facial stimulator instrument 106 in coordination with the delivery of the electrical stimulation. For example, an electrical stimulus such as an electrical pulse may be generated and delivered via electrodes 2218A and 2218B to the patient at the same instant that the armature 2212 is accelerated to generate a force impulse. The coordination of the delivery of force impulses and electrical stimulation may be controlled using signals received by the facial stimulator instrument 106 from the facial treatment application 120.

The force impulses are delivered to the facial tissues via the tips 2216 of the probe 2204 located at the forward end 2232 of the housing 2228. In an aspect, the tips 2216 may be cushioned for contacting the soft tissue to be treated. The probe 2204 may be constructed of a rigid material such as metal, plastic, or the like. The probe 2204 may screw into or frictionally insert into the piezoelectric sensor 2206. Different shaped probes 2204 may be used depending on the desired function of the facial stimulator instrument 106. For example, if the facial stimulator instrument 106 is measuring facial tissue response to force impulses, a different probe shape may be used compared to a probe 2204 used to implement a facial tissue treatment. Electrodes 2218A and 2218B may be supported on the probe tips 2216 in order to provide sufficient electrical contact with the skin 4 when the probe 2204 is applied to the patient.

The housing 2228 contains a solenoid assembly 2220. The assembly 2220 includes an electromagnetic coil 2210 and an armature 2212 longitudinally reciprocally mounted without attachment within the coil 2210. The armature 2212 is configured so that the end of the armature 2212 will impact against the anvil 2208 when the electromagnetic coil 2210 is energized. The anvil 2212 is affixed to one side of a piezoelectric sensor 2206. The impact produces a force impulse which travels through the piezoelectric sensor 2206 and causes the piezoelectric sensor 2206 to generate a waveform.

When any one of the various probes 2204 is placed against the facial tissue of a patient, the end of the probe 2204 opposite to the patient resides firmly against the piezoelectric sensor 2206 which in turn resides firmly against the anvil 2208. In an aspect, a pressure sensor 2214 situated within the housing 2228 and interposed between the closed end 2234 of the housing 2228 and the solenoid assembly 2220 may control the initiation of a force impulse. The pressure sensor 2214 works in concert with each of the other components so that upon reaching exceeding a predetermined threshold pressure against the facial tissue of the patient, the pressure sensor 2214 signals the release of a burst of current that energizes the electromagnetic coil 2210, inducing the acceleration of the armature 2212 within the electromagnetic coil 2210 until the armature 2212 impacts the anvil 2208.

The impact of the armature 2212 against the anvil 2208 produces a force impulse which travels through the piezoelectric sensor 2206 in a direction essentially aligned with the movement of the armature 2212 just prior to impact. In an aspect, the direction of travel of the force impulse may be influenced by the resistive force of the probe 2204 applied to the piezoelectric sensor 2206 opposite to the anvil 2208. The resistive force results from the contact force of the probe 2204 and the patient's skin.

The kinetic energy at the point of impact of the armature 2212 on the anvil 2208 causes the piezoelectric sensor 2206 to emit an electronic waveform which is characteristic of all of the force-producing Vectors of the electromechanical system situated on the anvil side of the piezoelectric sensor 2206 and opposed by the patient's facial tissues situated on the probe side of the piezoelectric sensor 2206. This electronic waveform may be received and processed by modules of the facial treatment application 120 and may further be stored within the database 122.

The mass of the armature 2212 may be substantially equal to the mass of the anvil 2208 so that when the armature 2212 strikes the anvil 2208, the reactive force induced by impact of the armature 2212 is transferred to the facial tissue of the patient through the anvil 2208, piezoelectric sensor 2206, and attached probe 2204. The initial separation distance of the armature 2212 and anvil 2208 may be fixed by design, such that the kinetic energy and resulting impact force may be varied only by varying the velocity of the armature 2212 at the point of impact with the anvil 2208. The velocity of the armature 2212 may be varied by varying the inductive force of the electromagnetic coil 2210 on the armature 2212 by varying the magnetization time (excitations time) to the electromagnetic coil with constant voltage and current. 2210.

In one aspect, the solenoid assembly 2220 may be actuated by processing measurements from a pressure sensor 2214 and actuating the solenoid assembly 2220 when the measured pressure meets or exceeds a threshold pressure as described herein above. The pressure sensor 2214 may be any known pressure-sensing device including, but not limited to, a load cell.

In another aspect, the trigger point at which the solenoid assembly 2220 may be actuated by the movement of the housing 2228 relative to the solenoid assembly 2220 produced by pressing the probe tip 2216 against the skin of the patient. This movement may be configured to complete an electrical circuit to the power supply of the solenoid assembly 2220 when a preset probe tip pressure is matched or exceeded. In an aspect, the preset pressure may be varied by varying the resistance of the relative movement of the housing 2228 to the probe tip pressure by incorporating a resilient element such as a spring between the structure of the housing 2228 and the support structure of the solenoid assembly 2220. In another aspect, the present pressure may be varied by varying the distance of relative movement needed to complete the electrical circuit to the power supply of the solenoid assembly 2220.

b. Electrical Stimulator Function

In an aspect, the facial stimulator instrument 106 is configured to develop and deliver electrical stimulation comprising a series of electrical pulses to the facial tissues of a patient through the probe tip-mounted electrodes 2218A and 2218B, providing an electrostimulation therapy to the facial tissues. Control signals received from the computing device 102 by the facial stimulator instrument 106 via an electrical cable 2236 or other signal communication method control one or more characteristics of the electrical stimulation. Non-limiting examples of characteristics of the electrical stimulation include the frequency of production of the electrical pulses, waveforms of the electrical pulses, the current or voltage of the electrical pulses, and the duration of the series of electrical pulses.

The electrical stimulation falls within known ranges typically used for this type of therapy. For example, the frequency of production of the electrical pulses may be varied between about 0.1 Hz and about 150 Hz. Non-limiting examples of suitable waveforms for electrical pulses used in the electrical stimulation include high voltage mono-phasic, high voltage bi-phasic, Russian symmetrical bi-phasic, square wave mono-phasic, square wave bi-phasic, and any combination thereof. In another aspect, the galvanic response of the facial tissue being treated may be monitored via the electrodes 2218A and 2218B and processed by modules of the facial treatment application 120 to calculate any change in the galvanic response of the facial tissue resulting from the treatment. The calculated change in galvanic response of the facial tissue being treated may be used to determine if, and how, the electrical stimulation of the treatment may be changed. The galvanic response may be monitored continuously during the treatment, measured over a discrete pre-treatment period, and/or measured over a discrete post-treatment period.

The electrical stimulation administered to the facial tissues by the facial stimulator instrument 106 is produced using a high frequency oscillator 2224 and a power amplifier 2226 electrically connected to the electrodes 2218A and 2218B. When pressed against the skin of the patient, the electrical current is transferred from the electrode 2218 to the patient's facial tissues. In one embodiment, the delivery of the electrical stimulation is synchronized with the delivery of the force impulses by one or more modules of the facial treatment application 120. The peak amplitude of the electrical stimulation may be limited by the patient's comfort level during treatment. The lower the peak amplitude of the electrical pulses, the more tolerant the patient is to the electrical stimulation transmitted by the electrode 2218.

In one aspect, the application of electrical stimulation to a facial tissue involves pressing a pair of electrodes 2218A and 2218B attached to the probe tips 2216 against the skin of the patient, and causing a pulse of electrical current to flow from one electrode 2218A, through a facial tissue, and back to the other electrode 2218B. In another aspect, the application of electrical stimulation involves pressing a single electrode 2218 to the skin of a patient and causing a pulse of electrical current to flow from the electrode 2218 to an electrode patch or other electrical conductor also attached to the skin of the patient. In this aspect, the electrode patch or other electrical conductor may be adhered or otherwise attached to the skin of the patient in a location near the facial landmark at which the electrode is pressed.

VIII. Acoustic Oscillator (RF Generator Modulated by Acoustic (Audio) Modulator)

Referring again to FIG. 1, the facial tissue treatments of a patient 110 may be implemented using an acoustic oscillator 108. The acoustic oscillator 108 may be configured to deliver a series of acoustic pulses to the facial tissues of a patient. The operation of the acoustic oscillator is typically controlled by a GUI or other graphic display generated by the facial treatment application 120.

Figure 26:
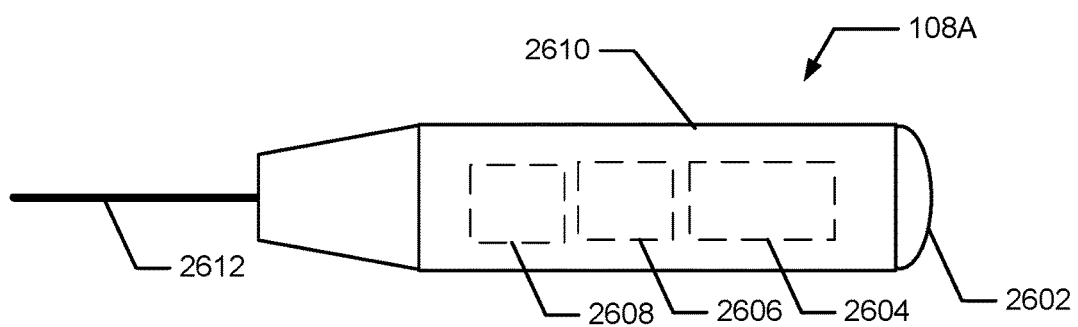
FIG. 26 is a cross-sectional side view of an acoustic oscillator.

An embodiment of an acoustic oscillator 108A is illustrated in FIG. 26. The acoustic coupler may include a transducer 2602 electrically connected to a band-pass filter and coupler 2604. An electrical oscillator 2608 and amplifier 2606 may supply the oscillating electrical signal used to drive the transducer 2602 at the desired frequency and amplitude. An electrical cable 2612 electrically connected to the computing device 102 supplies power to the acoustic oscillator. In addition, the electrical cable 2612 carries signals encoding data between the acoustic oscillator and the facial treatment application 120 resident on the computing device 102. A housing 2610 may contain the band-pass filter and coupler 2604, the electrical oscillator 2608 and the amplifier 2606. In addition, the transducer 2602 may be mounted to one end of the housing 2610, In an aspect, the acoustic oscillator 108 receives signals from the computing device 102 that control the production and delivery of acoustic pulses in accordance with a treatment protocol selected and specified using the modules of the facial treatment application 120 as described herein previously. The acoustic oscillator 120 may receive instrument control settings generated by the facial treatment application 120A including, but not limited to, the acoustic wave type, acoustic wave frequency, and acoustic wave amplitude within an acoustic pulse, the frequency of production of acoustic pulses, the duration of the series of acoustic pulses, and any other relevant instrument control settings.

In one aspect, the acoustic oscillator 108 may generate RF pulses having a frequency ranging between about 500 kHz and about 1.5 MHz. In another aspect, the acoustic oscillator 108 may generate acoustic pulses having a frequency of about 800 kHz. The form of the generated RF pulse may be any known RF waveform including, but not limited to, a sinusoidal waveform.

In another aspect, the pulse generation rate of the acoustic pulses may range between about 1 Hz and about 300 Hz. The amplitude or intensity of the acoustic pulses generated by the acoustic oscillator may correspond to sonic or ultrasonic oscillations in an additional aspect.

In yet another aspect, the system 100 may further include a pulse monitoring device (not shown) including, but not limited to: a pulse monitor mounted to the patient's arm, finger, chest, or other location; an EKG device; an echocardiography device; a blood pressure cuff or other blood pressure sensing device; and any other known pulse monitoring device. In this aspect, the pulse of the patient may be monitored by the system 100, and the application of acoustic pulses may be administered at a pre-determined time before, during, or after a heartbeat of a patient to enhance the effect of the acoustic pulses. In another additional aspect, an acoustically conductive gel such as a water-based gel compound may be applied to the patient's skin to enhance the transmission efficiency of the acoustic pulses to the facial tissues of the patient.

XI. Administering RF Energy to Tissue at Optimal RF Frequency and Optimal Pulse Frequency In one embodiment of the system 100 of FIG. 1, the system 100 includes any of the above-described features and further includes a pressure wave system or module that is part of the system 100 of FIG. 1 and is used with the acoustic oscillator 108. Specifically, the pressure wave module may be in addition to or in place of the facial stimulator instrument 106 and its supporting apparatus and algorithms. Such a pressure wave system or module 5010 is depicted diagrammatically in FIG. 29. In one embodiment, the pressure wave module 5010 and associated methods include the delivery of pressure waves (e.g., sound waves) 20 to a patient's skin tissue (e.g., skin tissue on the patient's face, neck, etc.) 25 in pulses that range in frequency of 1 Hz to 300 Hz for neurological stimulation. In other words, in one embodiment, a burst of pressure wave energy 20 is delivered to the patient's facial target tissue 25.

Figure 29:
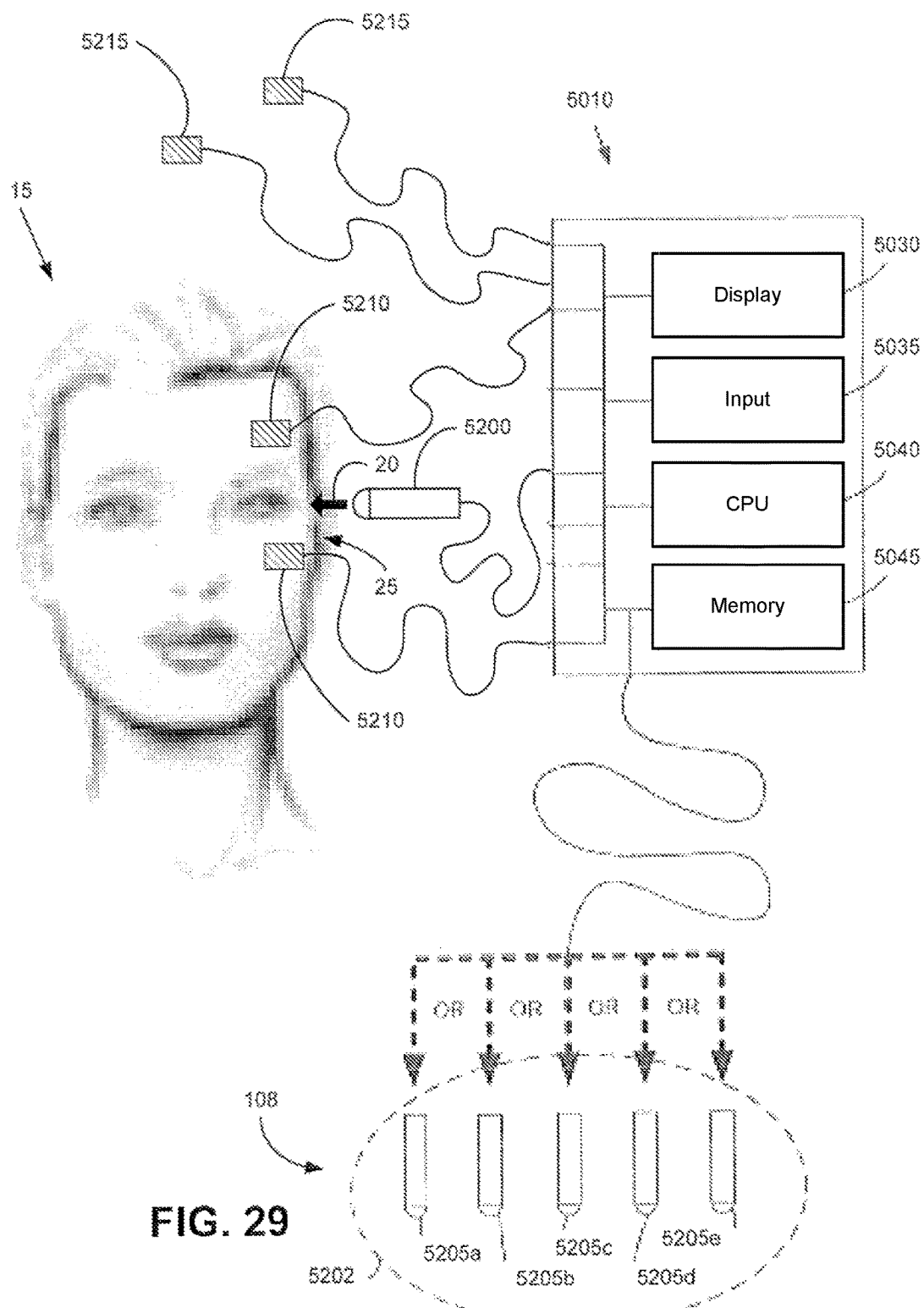
FIG. 29 is a schematic diagram of an alternative embodiment of the system being used on the patient.

As can be understood from FIG. 29, which is a schematic diagram of the system 5010 being used on the patient 15, the system includes a display 5030, an input 5035, a central processing unit (CPU) 5040, a memory 5045, and at least one pressure wave (RF energy) generator (e.g., sound wave generator) 108. The display may include a LCD or other type of screen for displaying information associated with the use of the system 5010 in treating a patient 15. For example, the display 5030 may display the patient's age, face, name, medical history, treatment durations, timing sequences, and protocols, and pressure wave shapes, frequencies, etc.

The input 5035 is in electrical communication with the display 5030 and may include a keyboard, touch screen, mouse, stylus, and/or other type of input mechanism. The input is configured to receive information associated with the treatment of the patient, such as patient age, skin tissue condition and location, desired treatment durations, timing sequences, and protocols, etc.

The CPU 5040 is in electrical communication with the display 5030, the input 5035, and memory 5045. The memory 5045 may include treatment parameters and protocols associated with the treatment of the patient such as, for example, pressure wave types, frequencies, magnitude, etc. for different type of patients, patient skin tissue, and skin tissue conditions.

The pressure wave generating device 108 is in electrical communication with the CPU 5040 and is configured to deliver a pressure wave (e.g., sound wave) to a tissue 25 of the patient 15, such as, for example, the face, neck or other cosmetically treated skin regions of the patient. The pressure wave generating device 108 may be in the form of a handheld wand, as shown, or may be equipped with a strap or other arrangement to allow the pressure wave generating device 108 to be strapped to the patient 15. The pressure wave generating device 108 may be capable of generating a wide range of pressure energy (e.g., sound energy) 20, including ultrapressure (e.g., ultrasound), and short waves through long waves. In one embodiment, the pressure energy 20 generated by the pressure wave generating device 108 is a long wave pressure wave.

Typically, a conductive gel is applied to the patient's skin tissue 25 to aid in the transmission of the pressure wave to the patient's skin and the underlying tissues and muscle. The pressure wave generating device 108 is configured to deliver a pressure wave having a frequency between 500 kHz and 1.5 MHz. In a preferred embodiment, the pressure wave generating device 108 delivers an 800 kHz pressure wave to the patient 15. Preferably, the pressure wave has sinusoidal waveform, although other waveforms and wave profiles may also be generated.

In various embodiments, the pressure wave generated by the pressure wave generating device 108 may be modulated to transmit the pressure wave throughout the patient's skin and the underlying tissues and muscle. For example, the pressure wave may be pulsed at a lower frequency. In one example, the pressure wave having a frequency between 500 kHz and 1.5 MHz may be pulsed at lower frequency between 1 Hz and to 300 Hz to transmit the energy of a pressure wave in frequencies known to evoke neurological potentials. The pulsing of the wave also reduces heat build up in the tissues and is intended to maximize the mechanical influence of the lower frequencies on the tissues and/or nerves.

Figure 35:
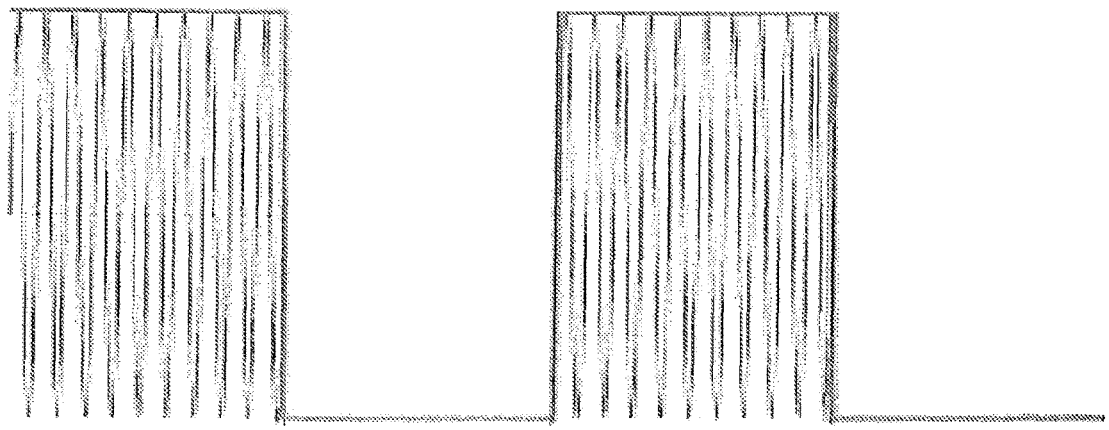
FIG. 35 is an example of a pulsed output signal similar to that depicted in FIG. 34.

The CPU 5040 causes the pressure wave-generating device 108 to generate a pressure wave of a desired frequency, magnitude, and duration to achieve neurological stimulation. For example, the pressure wave is achieved by introducing a pulsed pressure wave by pulsing an 800 MHz transmission wave in the frequency range of 1 Hz to 300 Hz in a sweep pattern so as to introduce all frequencies within the range within a programmable time period. The pressure wave may be generated continuously and modulated. FIG. 35 illustrates two types of patterns including amplitude modulation. Square waves or sinusoidal waves may be provided by the device.

Various embodiments of the system 5010 may contain more or less features according to the intended use and/or user of the system. For example, one embodiment of the system 5010 may be configured for home use by a patient. This embodiment of the system 5010 may not have extensive monitoring equipment. Conversely, another embodiment of the system 100 may be provided for clinical use. A clinical embodiment of the system 5010 may include all of the monitoring devices described herein, as well as other monitoring equipment or medical devices as desired by a medical professional. Regardless or whether the device is configured for home or clinical use, the system and method disclosed herein is advantageous in that it stimulates the nervous system and circulatory system, thereby improving the function and appearance of patient tissue typically the focus of health and beauty treatments, such as, for example, the skin and the underlying muscle and tissue of the face, neck, and etc.

In one embodiment, the system and method disclosed herein may include administering RF energy to patient tissue at a RF frequency determined to have the highest transmissibility in the tissue and at a pulse frequency determined to result in the highest electromyogram reading. As a result, the administration of the RF energy occurs at a RF frequency that will cause the RF energy to travel the greatest distance through the patient tissue, and the administration of the RF energy will be tailored to provide the most beneficial nerve stimulation.

As can be understood from FIG. 29, the system may also include an evaluation RF head 5200, a pressure wave generating device 108, a RF antenna(s) 5210, and an EMG sensor(s) 5215. The pressure wave generating device 108 may be in the form of a plurality 5202 of treatment RF heads 5205a-g. The evaluation RF head 5200 and RF antenna and/or and acoustic measuring device 5210 are capable of being placed in electrical communication with the CPU 5040.

Figure 30:
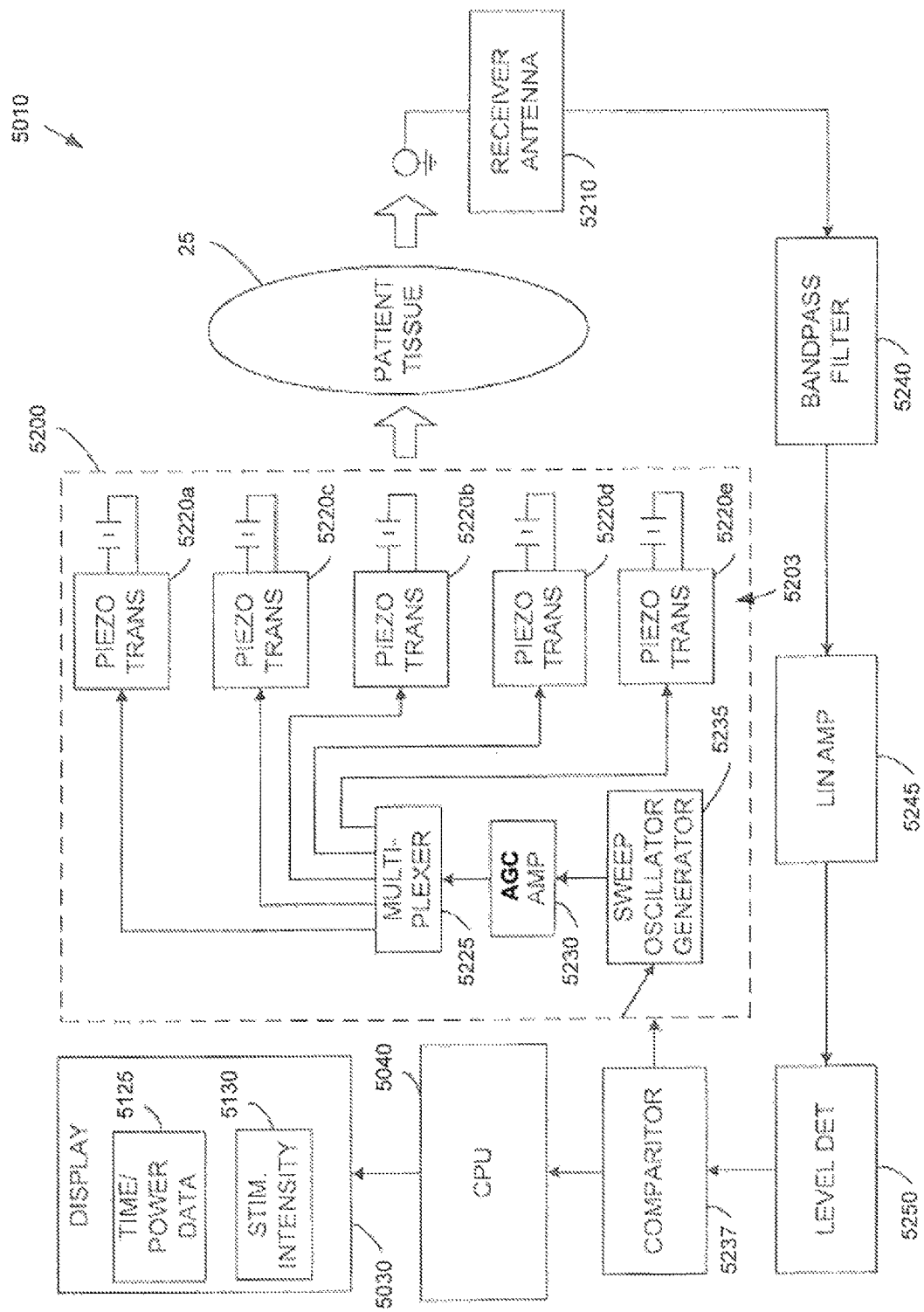
FIG. 30 is a schematic diagram of the system employing the evaluation RF head and the RF antenna for the embodiment of the system depicted in FIG. 29.

As illustrated in FIG. 30, which is a schematic diagram of the system 5010 employing the evaluation RF head 5200 and the RF antenna(s) 5210, the evaluation RF head 5200 includes an array 5203 of piezoelectric transducers 5220a-e electrically coupled to a multi-plexer or pulse control 5225 that is electrically coupled to an automatic gain control amplifier 5230 electrically coupled to a sweep oscillator generator 5235. The evaluation RF head 5200 is electrically coupled to a comparator 5237 that is electrically coupled to the CPU 5040 and display 5030.

Each piezoelectric transducer 5220a-e of the array 5203 is individually tuned to generate RF energy at a distinct frequency as compared to the other piezoelectric transducers of the array. The piezoelectric transducers 5220a-e forming the array 5203 of the evaluation RF head 5200 provide a range of distinct RF energy frequencies over a range of between approximately 500 KHz and approximately 1.5 MHz at steps of between approximately 50 KHz and approximately 200 KHz. For example, a first piezoelectric transducer 5220a may be tuned to 500 KHz, the second piezoelectric transducer 5220b may be tuned to 600 KHz, and so forth through the rest of the piezoelectric transducers such that the array 5203 is capable of providing RF energy at a frequency range of between approximately 500 KHz and 1.5 MHz with steps of 100 KHz, resulting in an array 5203 having 11 individually tuned piezoelectric transducers. Thus, the array 5203 is configured to generate RF energy over a range of frequencies not possible via a single piezoelectric transducer.

As can be understood from FIG. 30, the RF receiver antenna(s) 5210 is electrically coupled to a bandpass filter 5240 that is electrically coupled to a linear amplifier 5245 electrically coupled to a level detector 5250 electrically coupled to the comparator 5237. As indicated in FIGS. 29 and 30, the evaluation RF head 5200 is applied to patient tissue, and the RF receiver antenna(s) and or acoustic measuring device(s) 5210 is applied to another region of patient tissue at a different location spaced apart from the location wherein the head 5200 is being applied to the patient tissue. The RF receiver antenna(s) is configured to detect RF energy transmitted through the patient tissue from the evaluation RF head 5200. For example, as indicated in FIG. 29, where the tissue target location for the administration of the treatment is crow's feet wrinkles near the lateral edges of the patient's eyes, RF receiver antennas 5210 could be attached to the patient's skin on the forehead above the eyebrow and on the cheek below the eye.

When the evaluation RF head 5200 and RF receiver antenna(s) 5210 are applied to the patient tissue, the system 5010 is configured to cause the evaluation RF head 5200 to administer RF energy to the patient tissue over a range of RF frequencies by the sweep oscillator generator 5235 generating a series of frequencies in a step fashion across the range of frequencies of the array 5203 and the multi-plexer 5225 sending the appropriate stepped frequency to the appropriate piezoelectric transducer 5220a-5220e when said appropriate stepped frequency is generated by the oscillator generator 5235. As the array 5203 of the head 5200 sweeps through the various frequencies, the RF receiver antenna(s) 5210 senses the administered RF energy transmitted through the patient. The comparator 5237, in conjunction with the CPU 5040, identifies which RF frequency of the range of RF frequencies administered to the patient via the array 5203 of the head 5200 has the most transmissibility through the patient. The system 5010, via, for example, the display 5030, recommends a treatment RF head from the plurality 5202 of treatment RF heads 5205a-5205e that is capable of providing the identified RF frequency.

Each treatment RF head 5205a-5205e of the plurality 5202 treatment RF heads shown in FIG. 29 has a piezoelectric transducer tuned to a unique frequency different from those of the other heads 5205a-5205e. Thus, the plurality 5202 of treatment heads 5205a-5205e may be made up of a sufficient variety of treatment RF heads so as to cover a range of RF frequencies in a stepped fashion. For example, treatment RF head 5205a-5205e of the plurality 5202 is individually tuned to generate RF energy at a distinct frequency as compared to the other heads 5205a-5205e of the plurality 5202. The heads 5205a-5205e of the plurality 5202 provide a range of distinct RF energy frequencies over a range of between approximately 500 KHz and approximately 1.5 MHz at steps of between approximately 50 KHz and approximately 200 KHz. For example, the first treatment RF head 5205a may have a piezoelectric transducer tuned to 500 KHz, the second treatment RF head 5205b may have a piezoelectric transducer 5300 may be tuned to 600 KHz, and so forth through the rest of the treatment RF heads such that the plurality 5202 of treatment heads 5205a-5205e is capable of providing RF energy at a frequency range of between approximately 500 KHz and 1.5 MHz with steps of 100 KHz, resulting in plurality 5202 having 11 individually tuned treatment RF heads. Thus, a treatment RF head 5205a-5205e can be selected from the plurality 5202 to match the RF frequency identified via the array 5203 and comparator 5237 as discussed above with respect to FIG. 29.

Figure 31:
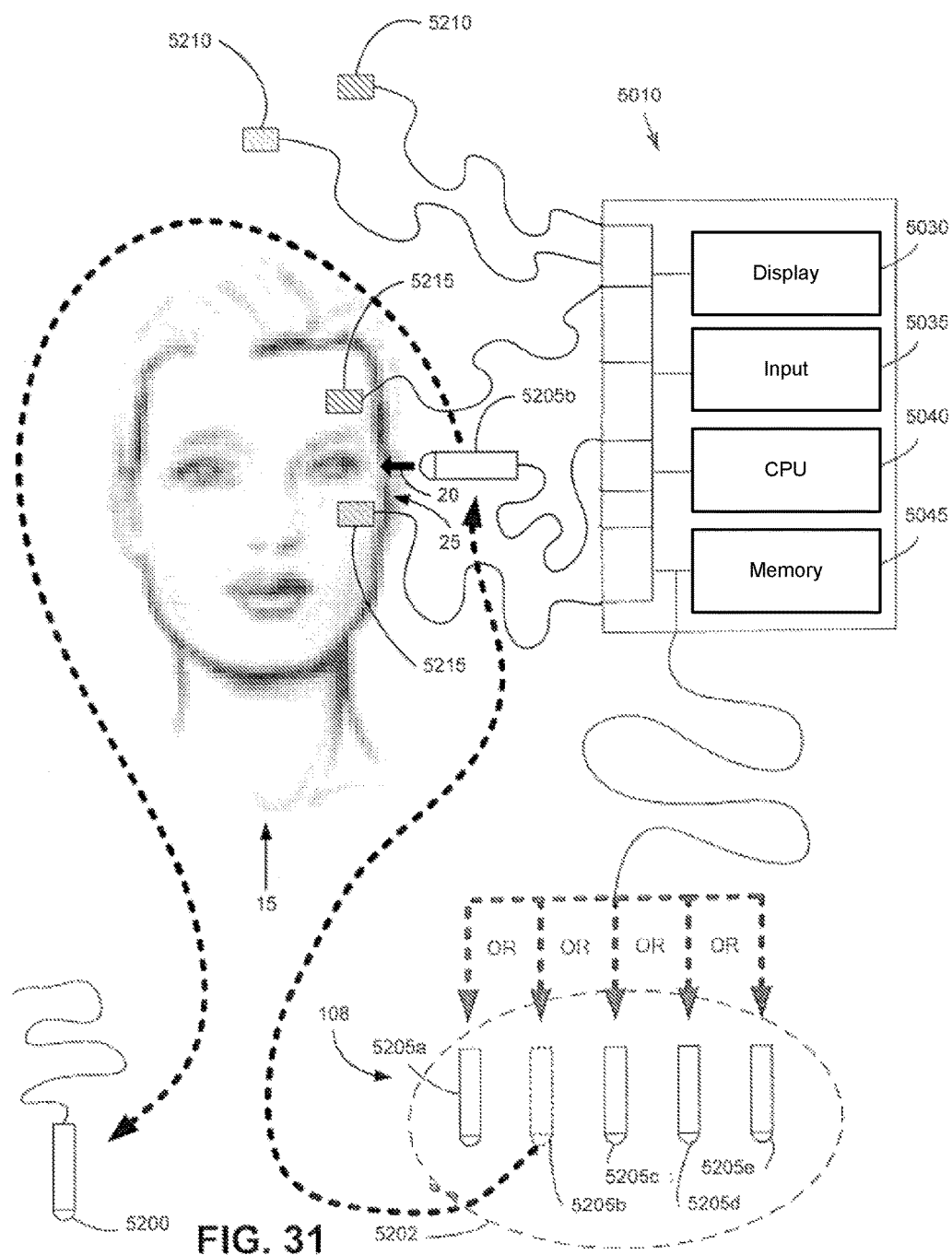
FIG. 31 is a schematic diagram of the system embodiment of FIG. 29, wherein the selected treatment RF head and EMG sensor are coupled to the system and being applied to the patient.

Once a treatment RF head 5205a-5205e is selected from the plurality 5202 that matches the identified RF frequency, the selected RF treatment head is electrically coupled to the system 5010, as illustrated in FIG. 31. For example, by using the array 5203 and comparator 5237 as described above with respect to FIG. 29, it is determined that a frequency of 600 KHz has the greatest transmissibility through the patient tissue 25 and, as a result, the system 5010 recommends from the plurality 5202 of heads the treatment RF head 5205b, which is tuned to operate at 600 KHz. As shown in FIG. 31, the treatment RF head 5205b is electrically coupled to the system 5010, and the EMG sensor(s) 5215 is electrically coupled to the system 5010. The treatment RF head 5205b and EMG sensor(s) 5215 are both applied to the patient tissue 25.

Figure 32:
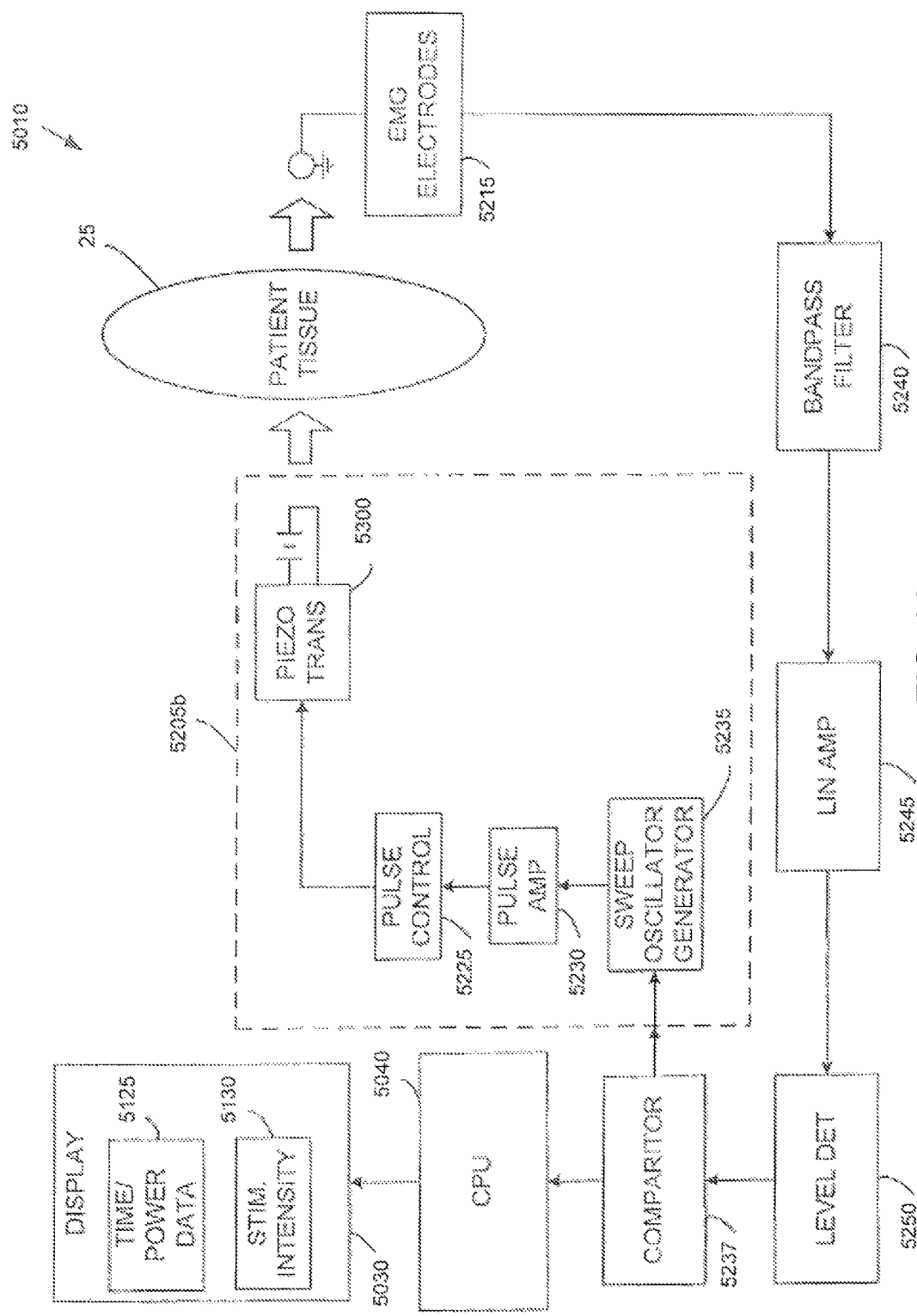
FIG. 32 is a schematic diagram of the system employing the selected treatment RF head and the EMG sensor for the embodiment of the system depicted in FIG. 29.

The system 5010 now appears as schematically depicted in FIG. 32. Specifically, the selected treatment RF head 5205b includes piezoelectric transducer 5300 electrically coupled to a pulse control 5225 that is electrically coupled to a pulse amplifier 5230 electrically coupled to a sweep oscillator generator 5235. The treatment RF head 205b is electrically coupled to a comparator 5237 that is electrically coupled to the CPU 5040 and display 5030 described above with respect to FIG. 29.

As can be understood from FIG. 32, the EMG sensor 5215, which has electrodes, is electrically coupled to a bandpass filter 5240 that is electrically coupled to a linear amplifier 5245 electrically coupled to a level detector 5250 electrically coupled to a comparator 5237. As indicated in FIGS. 31 and 32, the treatment RF head 5205b is applied to patient tissue 25, and the EMG sensor(s) 5215 is applied to patient tissue 25 at a different location spaced apart from the location wherein the head 5205b is being applied to the patient tissue. The EMG sensor(s) is configured to detect electromyogram in the patient tissue 25 from resulting from RF energy administered to the patient tissue via the treatment RF head 5205b. For example, as indicated in FIG. 31, where the tissue target location for the administration of the treatment is crow's feet wrinkles near the lateral edges of the patient's eyes, EMG sensors 5215 could be attached to the patient's skin on the forehead above the eyebrow and on the cheek below the eye.

When the treatment RF head 5205b and EMG sensor(s) 5215 are applied to the patient tissue, the system 5010 is configured to cause the treatment RF head 5205b to administer RF energy to the patient tissue at the identified RF frequency (which is 600 KHz in this example) over a range of pulse frequencies by the sweep oscillator generator 5235 and pulse control 5225 causing the administered 600 KHz RF energy to pulse at a series of frequencies in a step fashion across a range of pulse frequencies generated by the oscillator generator 5235. In one embodiment, the generator 5235 is configured to cause the treatment RF head 5205b to administer RF energy at the identified RF frequency (which is 600 KHz in this example) to the patient over a range of pulse frequencies between approximately 1 Hz and approximately 300 Hz at steps that are defined in the software via an algorithm that allows the user to determine the scan time, in one embodiment, between approximately 1 Hz and approximately 30 Hz. Optimum scan times are established for each tissue type and/or face, neck, etc. region in a database from empirical data. For example, a database contained in the memory of the system can be used to pre-select scan times based on the tissue or area of concern entered into the interface of the system, each tissue type or area of concern being correlated in the data base to specific scan times.

Figure 34:
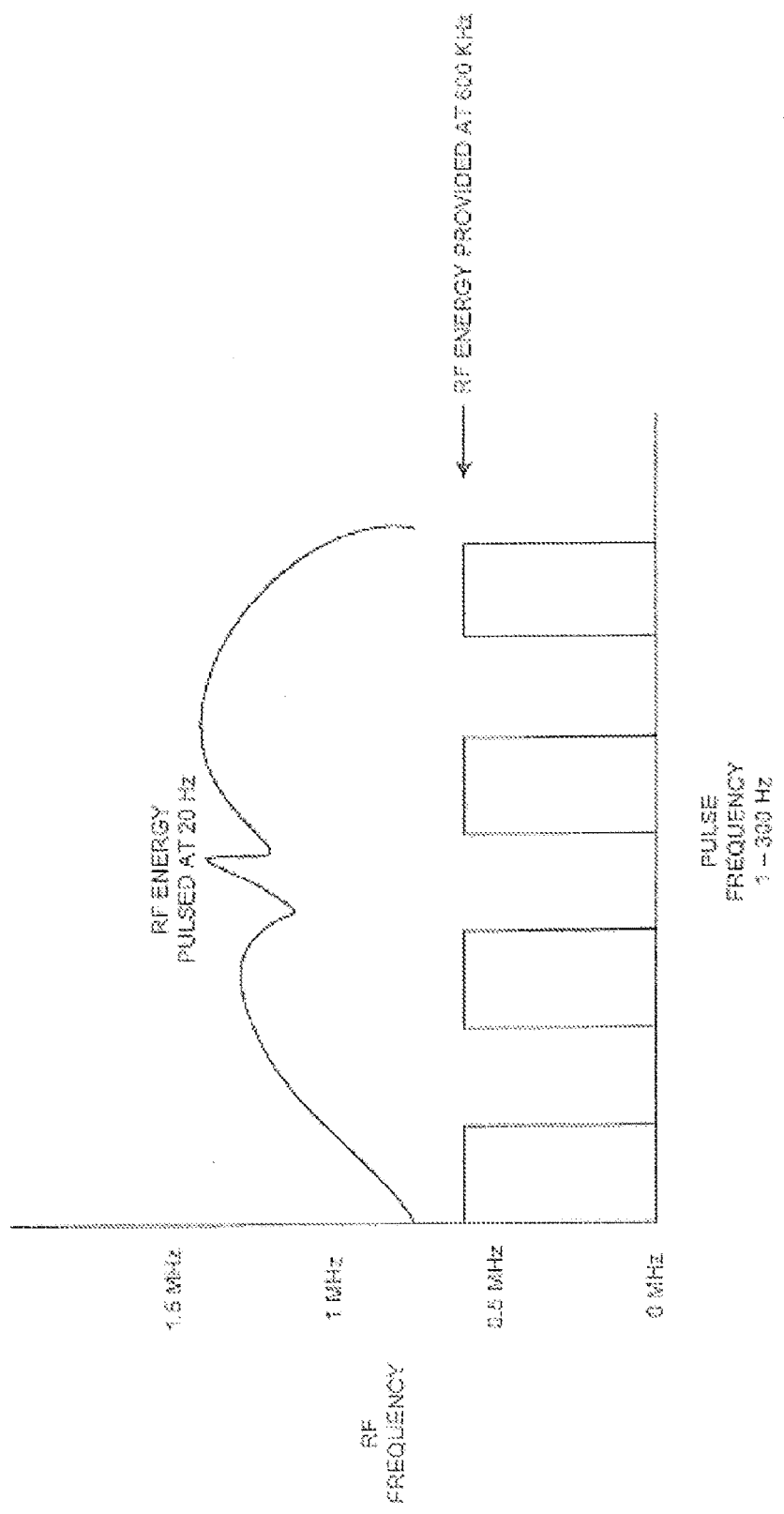
FIG. 34 is a graph of RF energy being administered at an example identified (optimum) RF frequency and pulsed at an example identified (optimum) pulse frequency.
Figure 36:
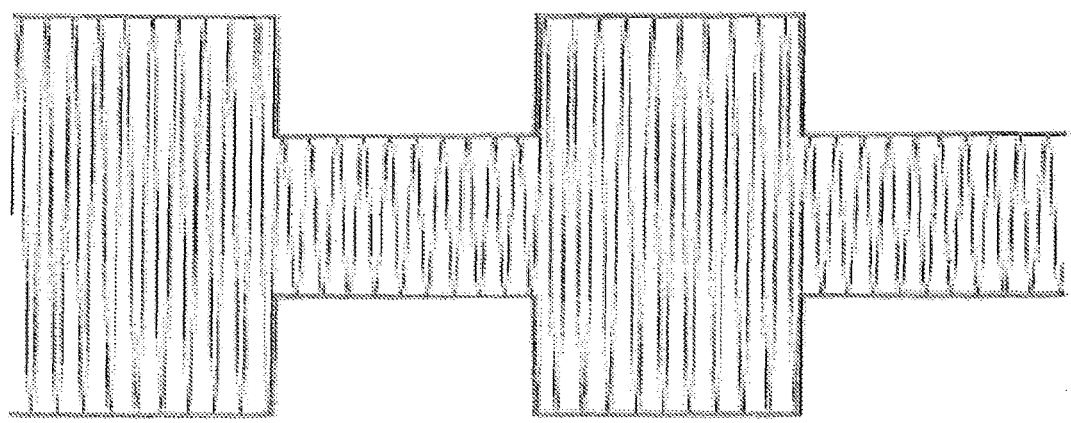
FIG. 36 is an example of a modulated output signal.

As the generator 5235 causes the head 5205*b* to sweep through the various frequencies, the EMG sensor(s) 5215 senses the resulting electromyogram in the patient. The comparitor 5237, in conjunction with the CPU 5040, identifies which pulse frequency of the range of pulse frequencies administered to the patient via the generator 5235 and head 5205*b* has the highest electromyogram reading in the patient. The system 5010, via, for example, the display 5030, recommends a treatment pulse frequency setting from the plurality of treatment pulse frequencies available to the treatment head 5205*b* via the generator 5235. For example, the EMG sensor and comparitor work together to determine a pulse frequency of 20 Hz resulted in the highest electromyogram readings in the patient. Accordingly, the system 5010 recommends using the treatment RF head 5205*b* to administer 600 KHz RF energy at a 20 Hz pulse frequency (i.e., the 600 KHz RF energy is pulsed at 20 Hz when being administered to the patient tissue). FIG. 34 illustrates a graph of RF energy being administered at the identified (optimum) RF frequency of 600 KHz and pulsed at the identified (optimum) pulse frequency of 20 Hz, as used in this example. FIG. 35 is an example of a pulsed output signal similar to that depicted in FIG. 34. FIG. 36 is an example of a modulated output signal. In some embodiments of the system, the RF energy can be administered at an identified (optimum) RF frequency (e.g., 600 Hz) and pulsed at the identified (optimum) pulse frequency (e.g., 20 Hz) such that the RF energy is pulsed similar to that depicted in FIG. 35. In some embodiments, the RF energy at the identified RF frequency may be modulated at the identified pulse frequency similar to that depicted in FIG. 36.

Figure 33:
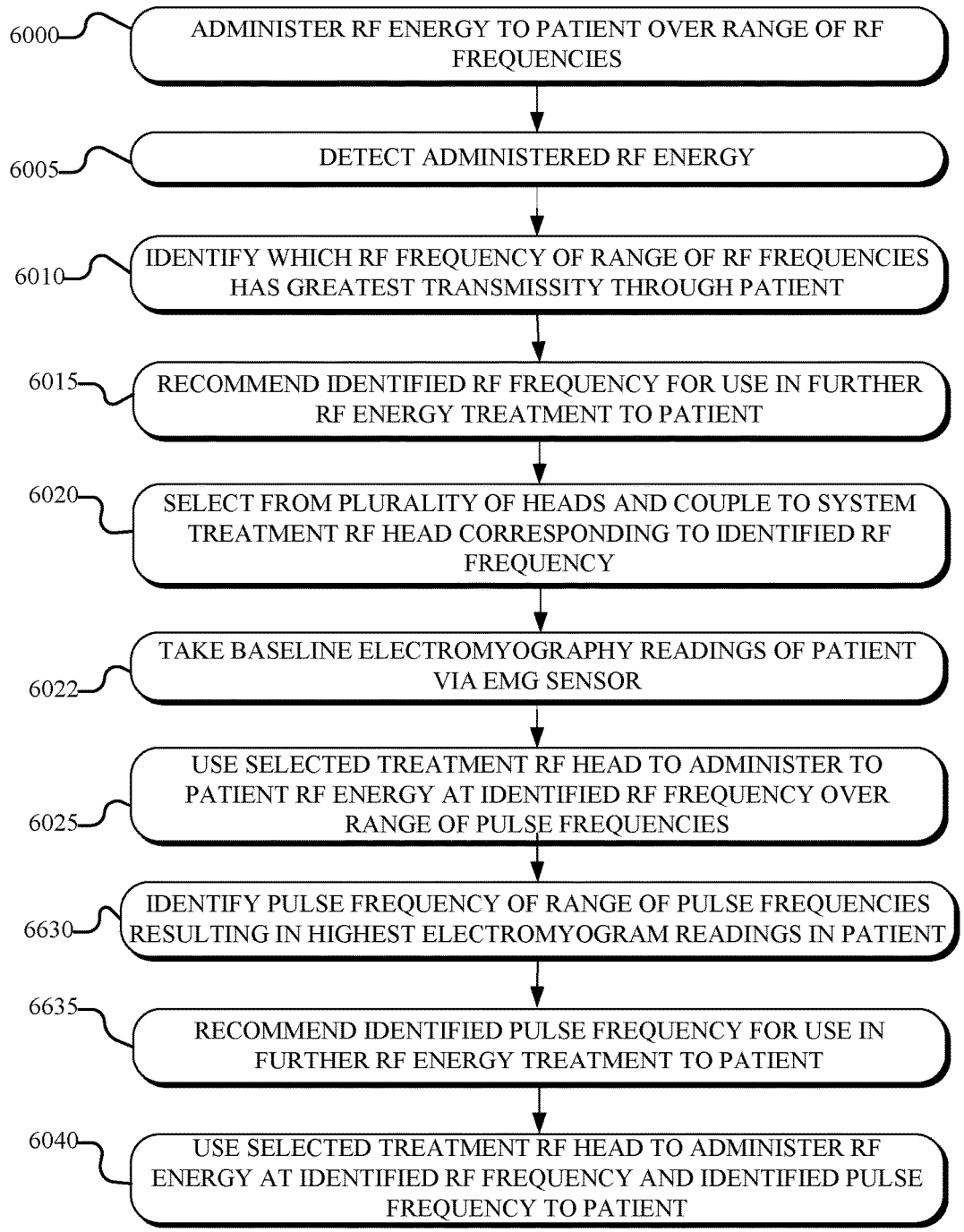
FIG. 33 is a flow chart illustrating an operational method associated with the system embodiment of FIG. 29.

As can be understood from the preceding discussion regarding FIGS. 29-32, a method is disclosed herein where RF energy is applied to the patient tissue at a more transmissible RF frequency and at a pulse frequency that results in the highest electromyogram readings. For example, as can be understood from FIG. 33, via the transducer array 5203 of the evaluation RF head 5200, RF energy is administered to the patient over a range of RF frequencies [block 6000]. Via the RF receiver antenna and/or acoustic measuring device(s) 5210, the administered RF energy is detected [block 6005]. The CPU 5040 and comparator 5237 identifying which RF frequency of the range of RF frequencies has the greatest transmissibility through the patient [block 6010]. The display 5030 recommends the identified RF frequency for use in further RF energy treatment to the patient [block 6015]. The applicable treatment RF head 5205*b* corresponding to the identified RF frequency is selected from the plurality 5202 of heads and coupled to the system 5010 [block 6020]. Baseline electromyography readings are taken of the patient via the EMG sensor(s) 5215 [block 6022] followed by using the selected treatment RF head 5205*b* to administer to the patient the RF energy at the identified RF frequency over a range of pulse frequencies [block 6025]. The EMG sensor(s) 5215, the comparator 5237 and CPU 5040 are used to identify the pulse frequency of the range of pulse frequencies resulting in the highest electromyogram readings in the patient [block 6030], and the display 5030 recommends the identified pulse frequency for use in further RF energy treatment to the patient [block 6035]. The selected treatment RF head 5205*b* is then used to administer the RF energy at the identified RF frequency and identified pulse frequency to the patient [block 6040].

While the system embodiment discussed above with respect to FIGS. 29-33 applies to patient tissue RF energy at an identified RF frequency and identified pulse frequency, in some embodiments, the system 5010 will apply an identified RF frequency over a range of stepped amplitudes instead of over a range of stepped pulse frequencies. Accordingly, once a specific stepped amplitude is identified as resulting in the highest EMG reading, the RF energy can be applied to the patient tissue at the identified RF frequency and identified amplitude.

By administering the RF energy to the patient tissue at an identified RF frequency and identified pulse frequency, the RF energy can be tailored to travel the greatest distance possible through the patient tissue at a pulse frequency that provides the greatest therapeutic result, as indicated by the EMG sensor readings, which give an instantaneous feedback of the therapeutic impact of the RF energy, such instantaneous feedback being less likely to be obtained via tissue temperature readings, tissue oxygenation readings, or other measurements. Over time and the course of treatment via the system 10, the patient tissue characteristics may change with respect to the RF frequency and/or the pulse frequency believed to be optimal for the therapeutic affect. Accordingly, the methodology outlined in FIG. 33 can be reapplied to identify a new optimal RF frequency, which will require the selection of a new treatment RF head from the plurality of such heads. Also, the new treatment RF head and above described methodology can be used to identify a new optimal pulse frequency. The system can then be used to administer the RF energy to the patient tissue at the new optimal RF and pulse frequencies.

Applying the pulsed RF energy to the patient tissue is advantageous in that it creates corresponding waves that travel through the patient tissue to release their energy at boundary layers such as, for example, facia, muscle, tendons or bone, etc. that are highly innervated. This release of mechanical energy at the boundary layers stimulates the nervous and vascular system, thereby providing a therapeutic benefit for tissues typically the focus of traditional health and beauty treatments. Pulsing the RF energy at the optimal RF frequency also reduces tissue heating as compared to continuously applied RF energy at the optimal RF frequency.

Figure 37:
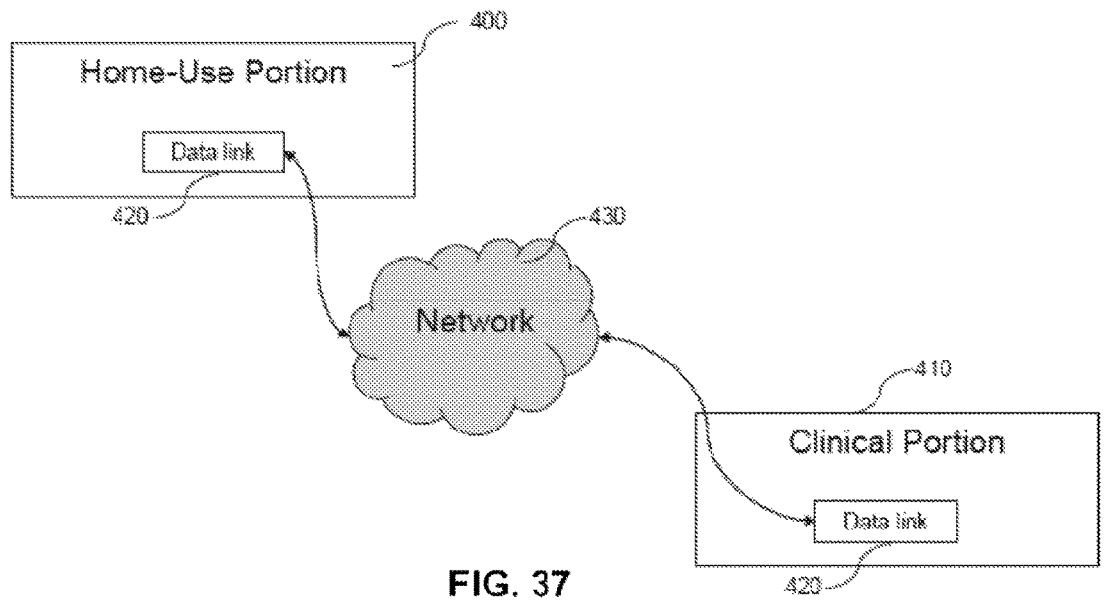
FIG. 37 is a schematic diagram of the system employing both the clinical and home-use portions connected by a network.
Figure 38:
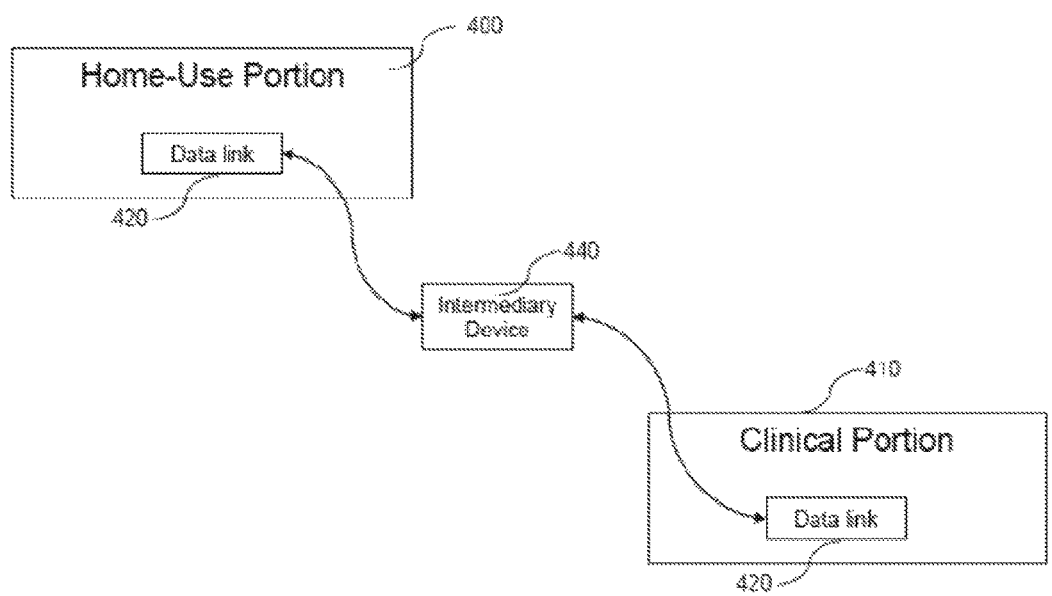
FIG. 38 is a schematic diagram of the system employing both the clinical and home-use portions connected by an intermediary device.

The embodiments of the system discussed above with respect to FIGS. 1-36 can also be employed as depicted in the diagrams of FIGS. 37 and 38, wherein the system may employ a portion for use by the physician at the clinic (i.e., a clinic portion) and a portion for use back at the patient home (i.e., a home-use portion). Specifically, the clinic portion is used by the physician at the clinic to diagnose the patient, formulate a treatment for the patient, treat the patient, and store treatment data associated with the actual treatment of the patient. The home-use portion is provided with the formulated treatment and, possibly, the stored treatment data and sent back to the patient home with the patient so treatment can be continued at the patient home without having to return to the clinic. For example, data and treatment information may be downloaded from the clinic portion into the home-use portion. In one embodiment, the clinic portion may be configured like any of the embodiments of the system discussed above, and the home-use portion may similarly configured but be in a more portable configuration, perhaps have fewer features as a result, and be capable of establishing a data link with the clinic portion.

As can be understood from FIGS. 37-38, in one embodiment, the home-use portion 400 and the clinic portion 410 may connect via the data link 420. The data 420 link may comprise a connection between the home-use portion 400 and the clinic portion 410 capable of uploading data relating to the operation and/or results of the treatment carried out on the home-use portion 400. The data link 420 may comprise any means for connecting the home-use portion 400 to the clinic portion 410 or a server, file storage system, or database that is readable by the clinic portion 410. For example, as indicated in FIG. 37, the data link may comprise a network connection 430 such as an Ethernet or Wi-Fi connection, a cellular connection, or any other network connection, and may connect to the clinic portion 410 either directly or through an intermediary such as over the Internet or any other network. The data link 420 may then upload operation and/or results data to the clinic portion for analysis.

In various embodiments, the data link 420 may comprise an I/O port capable of communicating with an intermediary device 440 that is in communication with the clinic portion 410. For example, as illustrated in FIG. 38 the intermediary device 440 may comprise a portable data storage device capable of being physically transported to the clinic portion 410 or connected to a device in electrical communication with the clinic portion 410. This may include a universal serial bus (USB) port connected to a USB drive, such as a conventional USB flash drive, external hard drive, or other USB enable storage device. The USB drive may be connected to the home-use portion 400 and may receive data related to the operation and/or results of treatments carried out on the home-use portion 400 from the data link 420. The USB drive may then be physically taken to the location of clinic portion 410 and the data uploaded via the data link 420 onto the clinic portion 410. In various other embodiments, the USB drive may be connected to a home computer or any other Internet-enabled device and the data may be uploaded to the clinic portion 410.

In various embodiments, the data link 420 may be configured to automatically send the operation and/or results data to the clinic portion. This may be done every time the home-use portion has completed treatment, at set time intervals, upon the request of the clinic portion, or according to the treatment results. For example, the data link may automatically upload the operations and/or results data at the end of every week. In another example, the data link may automatically upload the operations and/or results data when a result exceeds a threshold in some way. This may include one of many relevant comparisons. For example, besides tracking the user's treatment results, the home-use portion also may keep track of average results and standard deviation. If a user's results are unsatisfactory on average for a period of time, then modifications may be needed and the user's treatment and the data link may automatically send the operation and/or results data to the clinic portion regarding the poor results average. Similarly, if the user experiences outlier results that are outside of a set number of standard deviations from average, then the results may be uploaded. In the case of a non-network connected communications link, the user may be prompted by the home-use system to connect the intermediary device and either upload the data to the clinic portion or to take the intermediary device to their physician.

The foregoing merely illustrates the principles of the invention. Various modifications and alterations to the described embodiments will be apparent to those skilled in the art in view of the teachings herein. It will thus be appreciated that those skilled in the art will be able to devise numerous systems, arrangements and methods which, although not explicitly shown or described herein, embody the principles of the invention and are thus within the spirit and scope of the present invention. From the above description and drawings, it will be understood by those of ordinary skill in the art that the particular embodiments shown and described are for purposes of illustrations only and are not intended to limit the scope of the present invention. References to details of particular embodiments are not intended to limit the scope of the invention.

XII. Procedure for Administering Facial Treatment

In one embodiment, the system 100 is configured to apply therapy to the trigeminal nerve, certain connecting points of the facial muscles, and facial skin and muscles at certain facial landmarks and locations. While this therapy is described below as taking place in an order wherein the trigeminal nerve exit points are first measured and treated followed by the facial muscle connecting points and the facial skin and muscles, these measurements and therapies may occur in any order. Additionally, while this therapy is described below as taking place in order wherein the force impulse production procedure is first performed followed by the acoustic oscillator procedure, these therapies may occur in any order.

a. Force Impulse Production

Figure 39:
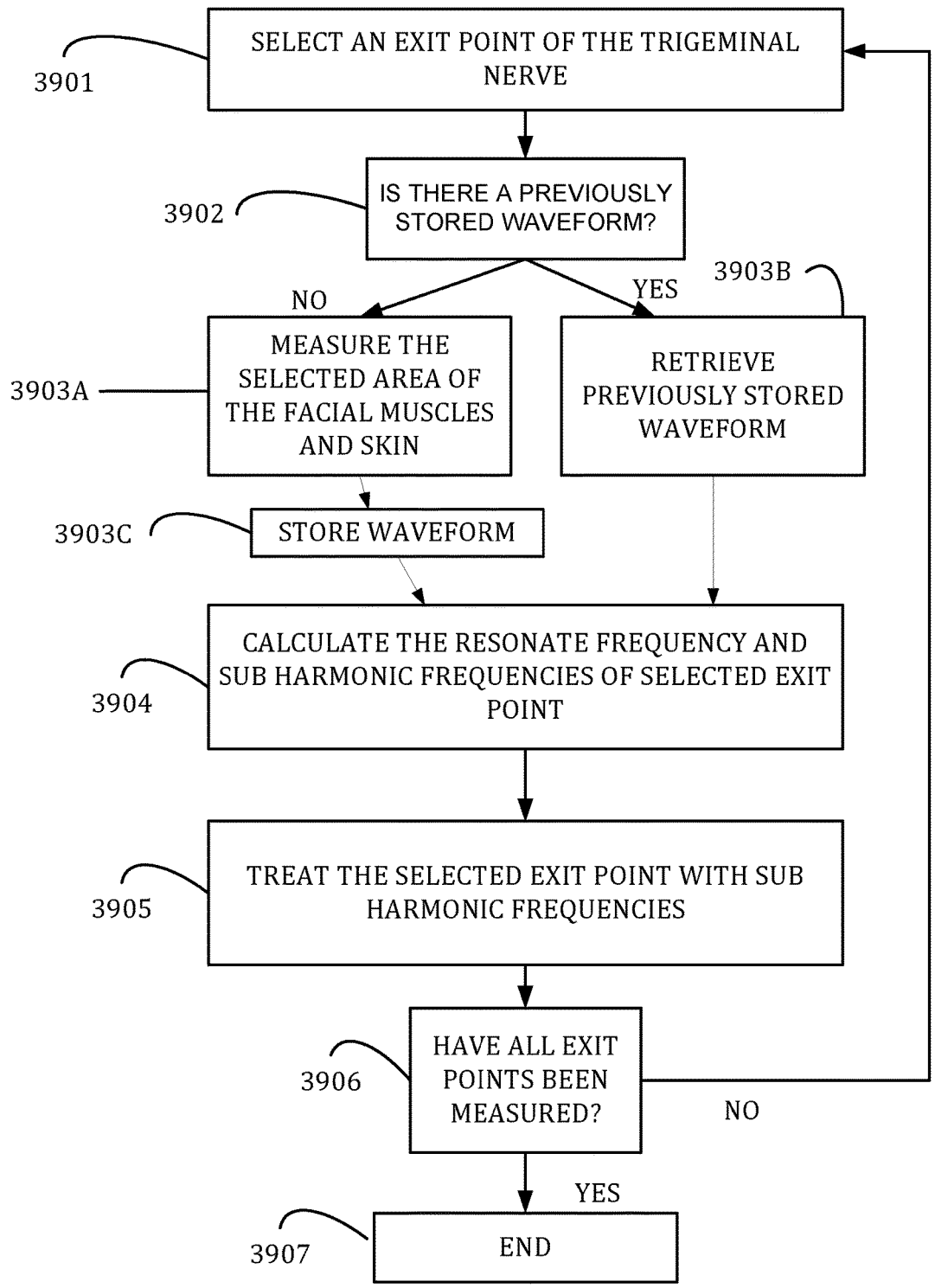
FIG. 39 is a flow chart illustrating a procedure for administering a facial treatment involving percussive therapy of a nerve delivered with a facial stimulator instrument.
Figure 42:
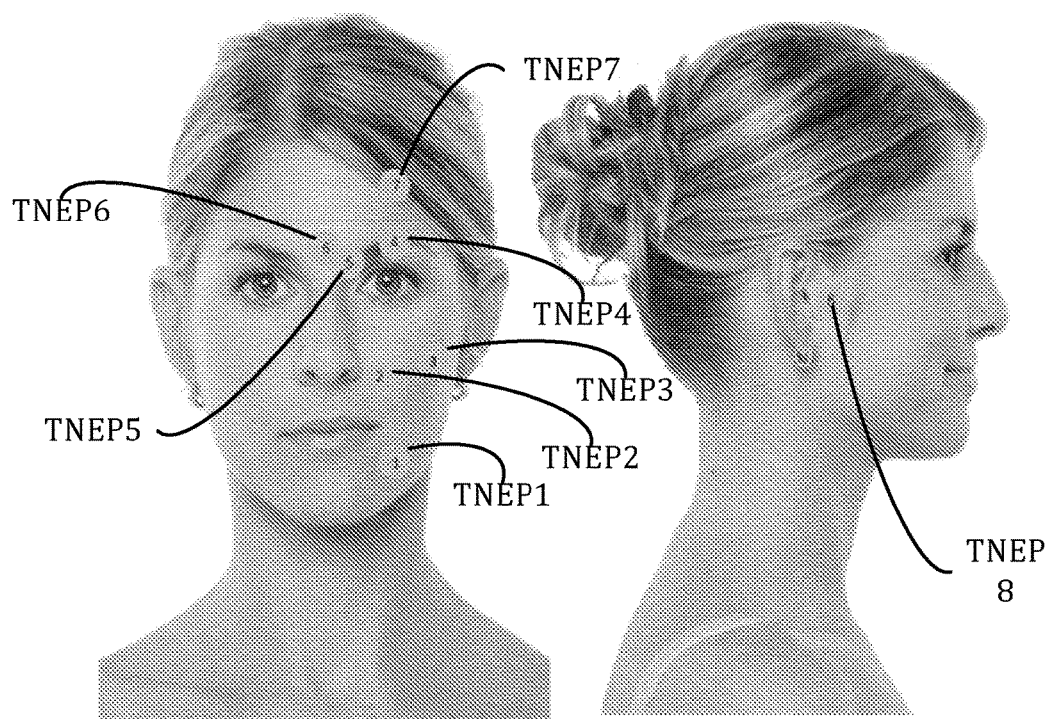
FIG. 42 depicts front and side view of a patient's face with the location of trigeminal nerve exit points depicted thereon.
Figure 43:
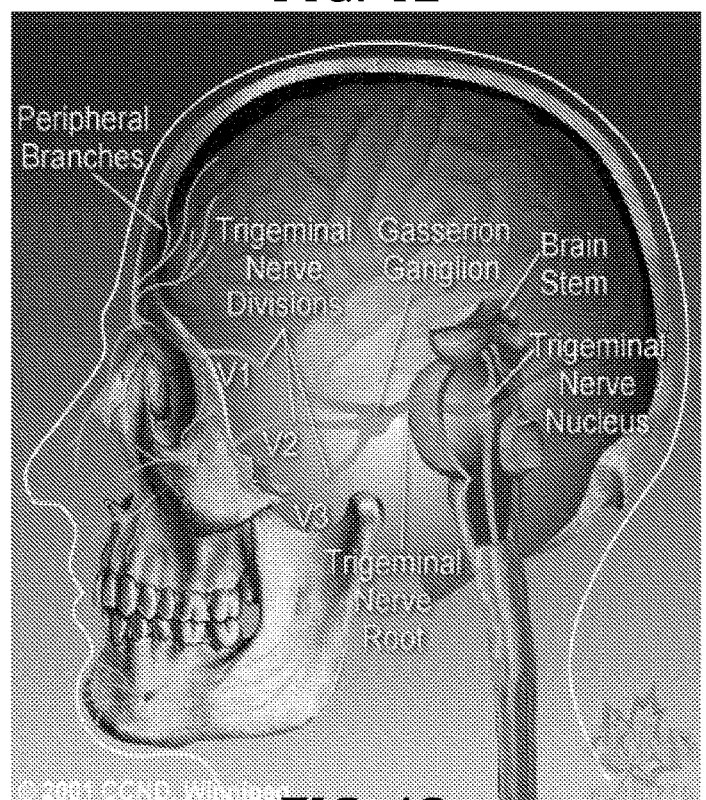
FIG. 43 depicts a side view of the patient's head with the anatomical routing of the trigeminal nerve.

As can be understood from the flow chart illustrated in FIG. 39, the trigeminal nerve exit points 4201-4208 depicted in FIG. 42, and the anatomical depiction of the trigeminal nerve illustrated in FIG. 43, in one embodiment, an exit point of the trigeminal nerve (e.g., 4201) is selected from several of such exit points (e.g., 4201-4208) [block 3901]. A practitioner can locate the nerve exit points (e.g., 4201), among other techniques, by palpitating the facial area adjacent the respective nerves. If a resultant waveform has not been previously measured and stored, the piezoelectric analysis/treatment head 2202 is then used to measure a resultant waveform from the selected exit point [block 3903A] of the trigeminal nerve by applying a percussive impact force onto the facial tissue immediately adjacent the trigeminal nerve and sensing the resultant waveform with the piezoelectric sensor 2206. The impact on the facial tissue produces a force impulse which travels through the piezoelectric sensor 2206 and causes the piezoelectric sensor 2206 to generate a waveform, which is stored [block 3903C] in the system 100. Alternatively, if the waveform has been previously measured and stored, the system 100 can retrieve the stored waveform [block 3903B]. From the resultant waveform, the system 100 calculates the resonate frequency and sub harmonic frequencies of the selected exit point [block 3904]. Additionally or alternatively, the system 100 can store resonate, fundamental, and other frequencies.

The piezoelectric analysis/treatment head 2202 can then be used to treat the selected exit point of the trigeminal nerve with the calculated sub harmonic frequencies [block 3905]. Specifically, in one embodiment, the treatment may be in one frequency range. Additionally or alternatively, the treatment may be a stepped frequency that steps through each sub harmonic within each range. Further, additionally or alternatively, the treatment may be a sweeping mode at programmable intervals. In one embodiment, one or more of the following sub harmonic frequency ranges are employed in the treatment of the exit point via the system 100: 0.1 to 3.99 Hz; 4 to 6.99 Hz; and 7 to 12 Hz. Once the treatment of the selected exit point (e.g., 4201) is complete, the system 100 asks if additional exit points exist that have yet to be treated [block 3906], and if the answer is "yes", then the system returns to the operation of block 3901 to start over at a new exit point (e.g., 4202) and repeat the process as outlined in blocks 3901 through 3907 until all exit points (e.g., 4201-4208) have been measured and treated. If the answer is "no", then the system 100 ends this part of the treatment methodology [block 3907].

Figure 40:
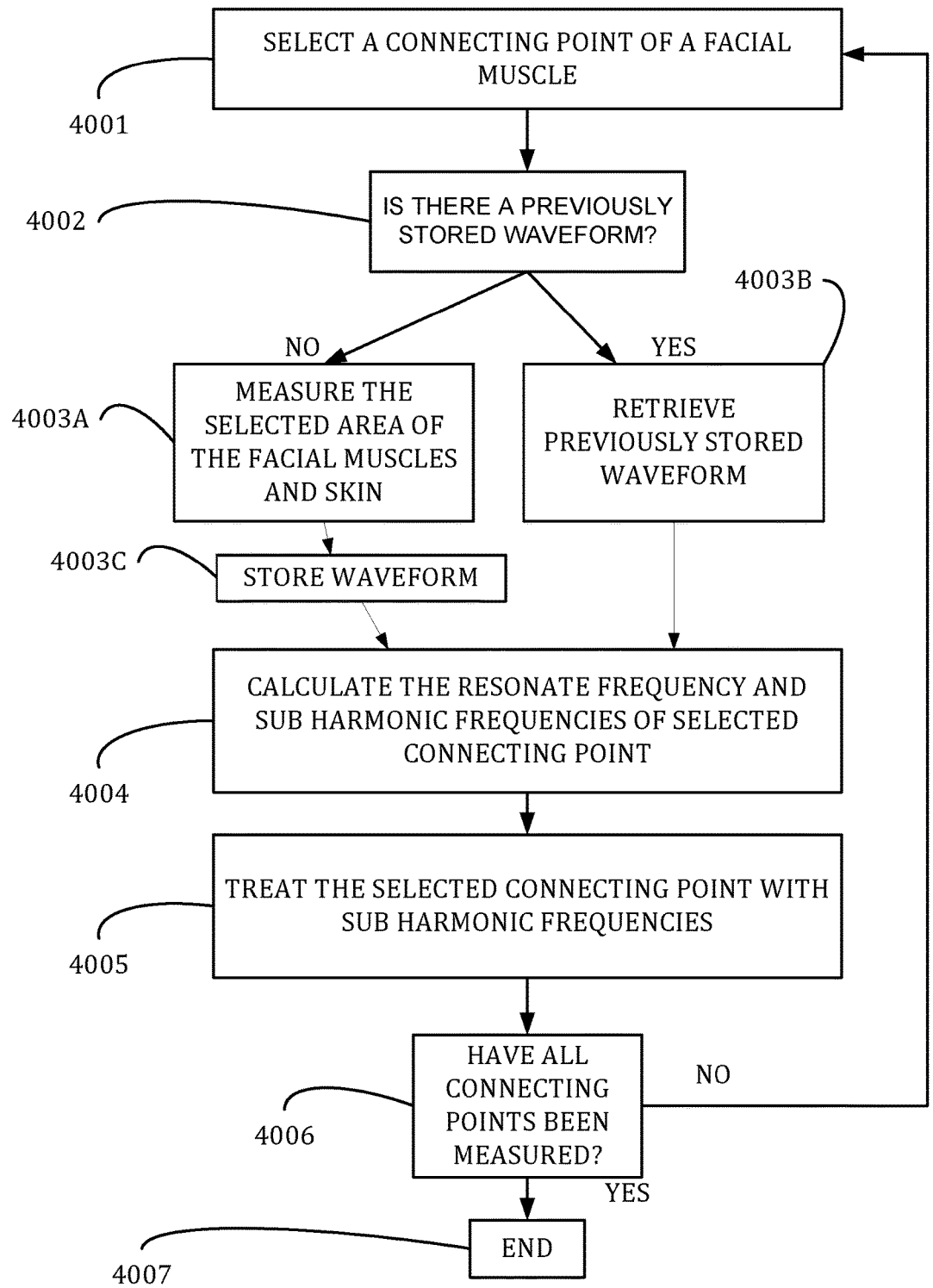
FIG. 40 is a flow chart illustrating a procedure for administering a facial treatment involving percussive therapy of a muscle delivered with a facial stimulator instrument.
Figure 44:
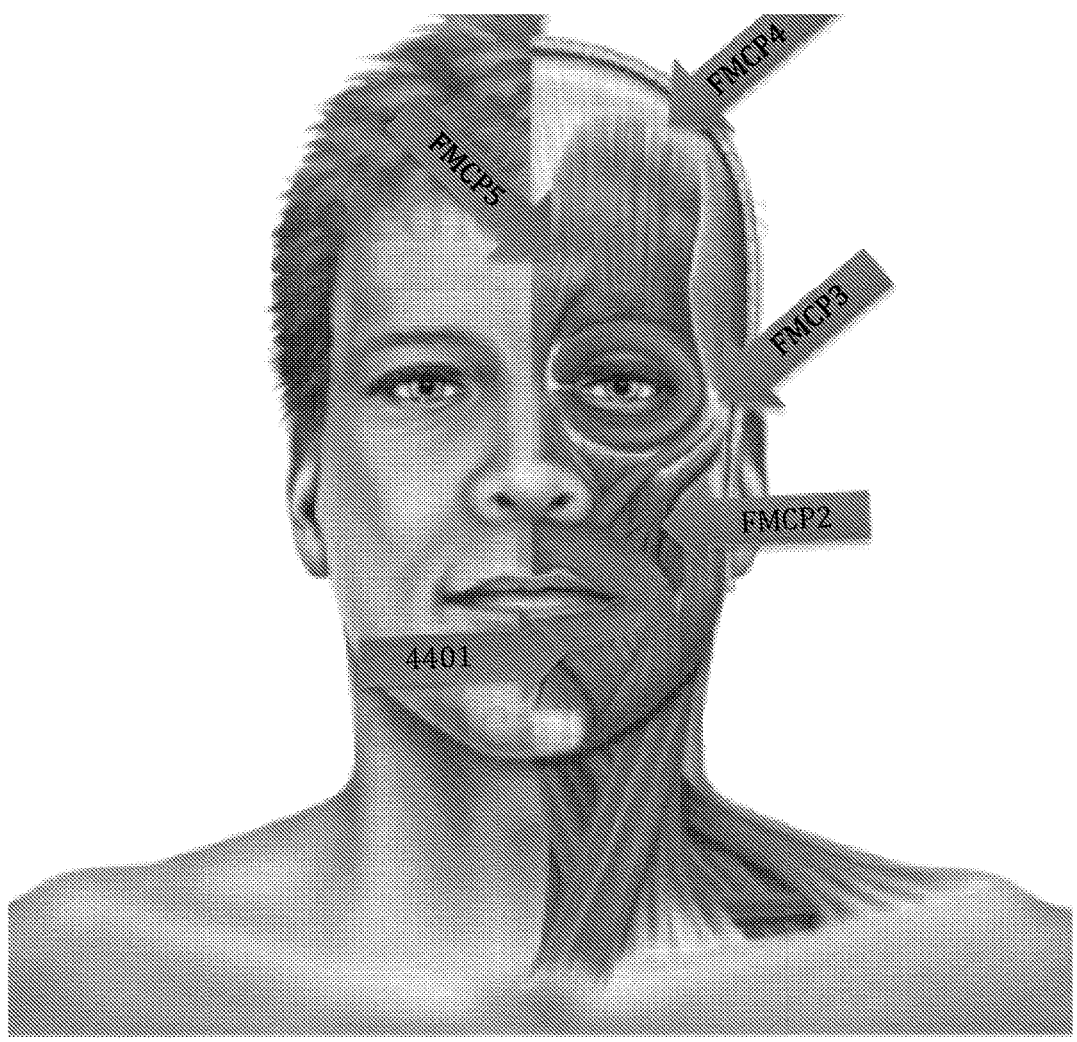
FIG. 44 depicts a front view of a patient's face with the location of facial muscle connection points depicted thereon.

In one embodiment, the system 100 is then used to apply therapy to certain connecting points of the facial muscles (e.g., 4401 through 44055). For example, as can be understood from the flow chart illustrated in FIG. 40 and the anatomical depiction of the facial muscle connecting points illustrated in FIG. 44, in one embodiment, a connecting point of a facial muscle (e.g., 4401) is selected from several of such connecting points (e.g., 4401 through 4405) [block 4001]. A practitioner can locate the muscle connecting points (e.g., 4401), among other techniques, by palpitating the facial area. If a resultant waveform has not been previously measured and stored, the piezoelectric analysis/treatment head 2202 is then used to measure a resultant waveform from the selected connecting point [block 4003A] of the facial muscle by applying a percussive impact force onto the facial tissue immediately adjacent the connecting point and sensing the resultant waveform with the piezoelectric sensor 2206. The impact on the facial tissue produces a force impulse which travels through the piezoelectric sensor 2206 and causes the piezoelectric sensor 2206 to generate a waveform, which is stored [block 4003C] in the system 100. Alternatively, if the waveform has been previously measured and stored, the system 100 can retrieve the stored waveform [block 4003B]. From the resultant waveform, the system 100 calculates the resonate frequency and sub harmonic frequencies of the selected connecting point [block 4004]. Additionally or alternatively, the system 100 can store resonate, fundamental, and other frequencies.

The piezoelectric analysis/treatment head 2202 can then be used to treat the selected connecting point of the facial muscle with the calculated sub harmonic frequencies [block 4005]. Specifically, in one embodiment, the treatment may be in one frequency range. Additionally or alternatively, the treatment may be a stepped frequency that steps through each sub harmonic within each range. Further, additionally or alternatively, the treatment may be a sweeping mode at programmable intervals. In one embodiment, one or more of the following sub harmonic frequency ranges are employed in the treatment of the connecting point via the system 100: 0.1 to 3.99 Hz; 4 to 6.99 Hz; and 7 to 12 Hz. Once the treatment of the selected connecting point (e.g., 4401) is complete, the system 100 asks if additional connecting points (e.g., 4402-4405) exist that have yet to be treated [block 4006], and if the answer is "yes", then the system 100 returns to the operation of block 4001 to start over at a new connecting point and repeat the process as outlined in blocks 4001 through 4007 until all connecting points have been measured and treated. If the answer is "no", then the system 100 ends this part of the treatment methodology [block 4007].

b. Acoustic Oscillator (RF Generator Modulated by Acoustic (Audio) Modulator)

In one embodiment, as discussed below with respect to the flow chart depicted in FIG. 41, the system 100 is then used to stimulate the skin and muscles of certain areas of the face. For example, the system 100 may be used to stimulate the face at certain areas such as the corner of the eyes, the corners of the mouth, the forehead, and the creases on either side of the nose and jawline. In one embodiment, screen prompts on the graphical user interface are initially provided on the display 112 of the system 100. These screen prompts can be followed in using an appropriate treatment RF head 5205a-5205e from the plurality 5202 of treatment RF heads shown in FIG. 29 and as per the procedure outlined in FIG. 33, to stimulate the certain skin and muscles areas. Examples of such treatment areas of the face are the corner of the eyes, the corners of the mouth, the forehead, and the creases on either side of the nose and jawline.

Figure 41:
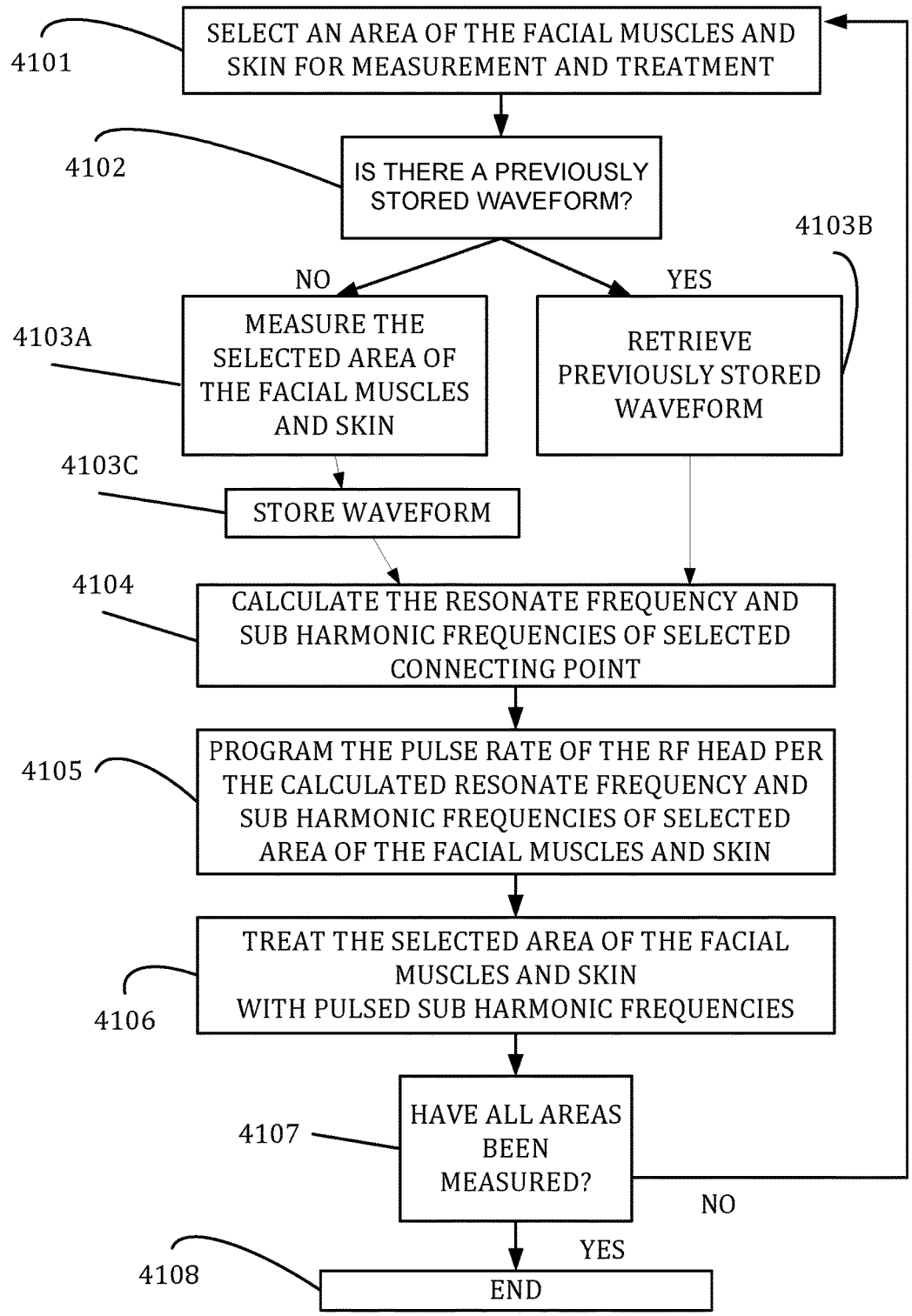
FIG. 41 is a flow chart illustrating a procedure for administering a facial treatment with an acoustic oscillator.

As illustrated in FIG. 41, a first area of the facial muscles and skin is selected for measurement and treatment from a group of such areas [block 4101]. The stored waveform from a previous therapy that utilized a piezoelectric treatment head 2202 can be retrieved [block 4103B] or a resultant waveform can be measured [block 4103A] as in the previous section through force impact production with a piezoelectric treatment head 2202. From the resultant waveform, either previously stored [block 4103B] or measured [block 4103A], the system 100 calculates the resonate frequency and sub harmonic frequencies of the first selected area of the facial muscles and skin [block 4004]. Additionally or alternatively, the system 100 can store resonate, fundamental, and other frequencies.

The calculated harmonic and sub harmonic frequencies are used to program the pulse rate of the treatment RF head 5205a-5205e [block 4105]. This pulse rate can be a fixed value of the measured frequency. Alternatively or additionally, the pulse rate can be a sub harmonic. Also, alternatively or additionally, the pulse rate can be a stepped frequency that switches between a base frequency and sub harmonics. Finally, alternatively or additionally, the pulse rate can be a sweeping mode that pulses between a harmonic and sub harmonic modes at programmable intervals.

The certain skin and muscle areas of the face may be treated by applying pulsed sub harmonic frequencies to selected areas of a patient in the range of: 0.1 to 3.99 Hz; 4 to 6.99 Hz; and 7 to 12 Hz [block 4106]. In one embodiment, the carrier frequency will be in the range of approximately 500 MHZ to approximately 1000 MHz. This treatment can be one frequency range. Alternatively or additionally, the treatment can be stepped frequency that steps through each sub harmonic within each range. Finally, alternatively or additionally, the treatment can be a sweeping mode at programmable intervals.

Once the treatment of the certain skin and muscle areas of the face is complete, the system 100 asks if additional certain skin and muscle areas of the face exist that have yet to be treated [block 4107], and if the answer is "yes", then the system 100 returns to the operation of block 4101 to start over at a new certain skin and muscle area of the face and repeat the process as outlined in blocks 4101 through 4106 until all certain skin and muscle areas of the face have been measured and treated. If the answer is "no", then the system 100 ends this part of the treatment methodology [block 4108].

In one embodiment, the piezoelectric head 2202 of the system 100 is used to measure and store frequency information about two distinct aspects of a patient's face, namely, the exit points of the trigeminal nerve and the facial muscle attachment points. This measured and stored frequency information is then used by the system in the treatment of the patient's face (e.g., the trigeminal nerve exit points and the facial muscle attachment points) via other treatment devices of the system 100 such as, for example, the RF head 5205a-5205e of the system.

In one embodiment, the piezoelectric head 2202 of system 100 is used to calculate base and sub harmonic frequencies for use in the RF head 5205a-5205e to program the pulse rate of the RF head 5205a-5205e. This pulse rate can be a fixed frequency of the true harmonic. Alternatively or additionally, the pulse rate can be a sub harmonic. Also, alternatively or additionally, the pulse rate can be a stepped frequency that switches between harmonic and sub harmonics. Finally, alternatively or additionally, the pulse rate can be a sweeping mode that pulses between harmonic and sub harmonic modes at programmable intervals.

In one embodiment, the RF head 5205a-5205e will have a pre-load function that will ensure that the RF head is in adequate contact with the skin before the power is turned on to promote proper usage of the system 5010.

What is claimed is:

1. A system for cosmetically treating tissue of a patient for at least one of improving skin appearance, reducing skin wrinkles, improving skin tone, or improving tissue function, the system comprising:
   a display configured to display information associated with the treatment of the tissue;
   an input in electrical communication with the display and including a key board and touch screen, the input configured to receive information associated with the treatment of the tissue;
   a central processing unit (CPU) in electrical communication with the input;
   a memory in electrical communication with the CPU and including treatment parameters associated with the treatment of the tissue;
   a first radio frequency (RF) head capable of being placed in electrical communication with the CPU and comprising an array of piezoelectric transducers, the array configured to generate RF over a range of frequencies not possible via a single piezoelectric transducer; and
   a RF receiver antenna capable of being placed in electrical communication with the CPU and configured to detect RF energy transmitted through the tissue from the first RF head;
   a plurality of second RF heads, each second RF head having a piezoelectric transducer tuned to a unique frequency and capable of being placed in electrical communication with the CPU; and
   an EMG sensor capable of being placed in electrical communication with the CPU and configured to detect electromyogram in the tissue;
   wherein, when the first RF head and RF receiver antenna are applied to the tissue, the system is configured to: a) cause the first RF head to administer RF energy to the tissue over a range of RF frequencies; b) cause the RF receiver antenna to sense the administered RF energy transmitted through the tissue; c) identify which RF frequency of the range of RF frequencies administered to the tissue has the most transmissibility through the tissue; and d) recommend a second RF head of the plurality of second RF heads that is capable of providing the identified RF frequency,
   wherein, when the recommended second RF head and EMG sensor are applied to the tissue, the system is configured to: a) cause the recommended second RF head to administer RF energy at the identified RF frequency to the tissue over a range of pulse frequencies; b) cause the EMG sensor to detect electromyogram in the tissue arising due to the RF energy administered to the tissue over the range of pulse frequencies; c) identify which pulse frequency of the range of pulse frequencies administered to the tissue causes the highest electromyogram readings in the tissue; and d) treat the tissue with the recommended second RF head at the identified RF frequency at the identified pulse frequency.

2. The system of claim 1, wherein the array is configured to generate RF over a range of between 500 KHz and 1.5 MHz.

3. The system of claim 2, wherein the array is configured to generate RF over a range of between 500 KHz and 1.5 MHz at steps of between 50 KHz and 200 KHz.

4. The system of claim 1, where the piezoelectric transducers of the array includes a first piezoelectric transducer, a second piezoelectric transducer, and a third piezoelectric transducer, wherein each of the first, second and third piezoelectric transducers generate RF at distinct frequencies from each other.

5. The system of claim 1, wherein the plurality of second RF heads includes individual second RF heads each tuned to a unique frequency from each other and each unique frequency is between 500 KHz and 1.5 MHz.

6. The system of claim 1, wherein, when the recommended second RF head is caused to administer RF energy at the identified RF frequency to the patient over a range of pulse frequencies, range of pulse frequencies is between 1 Hz and 300 Hz.

7. The system of claim 6, wherein the recommended second RF head is caused to administer RF energy at the identified RF frequency to the patient over the pulse frequency range of between 500 KHz and 1.5 MHz at steps programmatically controlled and optimized for tissue type via stored protocols.

8. The system of claim 1, further comprising an impulse head capable of being placed in electrical communication with the CPU and including a solenoid driven anvil configured to deliver mechanical impulse energy to the tissue, the impulse head further including a transducer sensor for detecting a wave generated in the tissue via the administration of the mechanical impulse energy to the tissue.

9. The system of claim 1, further comprising an electrode capable of being placed in electrical communication with the CPU and configured to administer electrical stimulation to the tissue and read electrical characteristics of the tissue in response to the electrical stimulation.

10. The system of claim 9, wherein the electrode is supported on the impulse head.

11. The system of claim 1, further comprising a camera capable of being placed in electrical communication with the CPU and configured to take images of the tissue, the system being configured to compare images of the tissue taken pre and post treatment via the system.

12. A method for cosmetically treating tissue of a patient for at least one of improving skin appearance, reducing skin wrinkles, improving skin tone, or improving tissue function, the method comprising:
   administering RF energy to the tissue over a range of RF frequencies;
   detecting the administered RF energy;
   identifying which RF frequency of the range of RF frequencies has the greatest transmissibility through the tissue;
   recommending the identified RF frequency for use in further RF energy treatment to the tissue; administering the RF energy at the identified RF frequency to the tissue over a range of pulse frequencies;
   identifying which pulse frequency of the range of pulse frequencies results in the highest electromyogram readings in the tissue;

recommending the identified pulse frequency for use in further RF energy treatment to the tissue; and administering the RF energy at the identified RF frequency and identified pulse frequency to the tissue.

13. The method of claim 12, wherein the administration of the RF energy to the tissue over the range of frequencies is accomplished via a RF head having an array of piezoelectric transducers each tuned to an individual unique frequency, the array being configured to generate RF over a range of between 500 KHz and 1.5 MHz.

14. The method of claim 12, wherein the administration of the RF energy to the tissue over the range of frequencies is over a range of between 500 KHz and 1.5 MHz at steps of between 50 KHz and 200 KHz.

15. The method of claim 12, wherein the recommending the identified RF frequency for use in further RF energy treatment to the tissue includes identifying a specific RF head from a plurality of RF heads that is configured to provide the recommended RF frequency.

16. The method of claim 12, wherein the administering the RF energy at the identified RF frequency to the tissue over a range of pulse frequencies occurs over a pulse frequencies ranging between 1 Hz and 300 Hz programmatically controlled and optimized for tissue type via stored protocols.

17. The method of claim 12, wherein the administering the RF energy at the identified RF frequency to the patient over a range of pulse frequencies occurs over a pulse frequencies ranging between 1 Hz and 30 Hz.

* * * * *